(12) United States Patent
Miller

(10) Patent No.: US 9,534,223 B2
(45) Date of Patent: *Jan. 3, 2017

(54) METHOD OF REDUCING BIOFILMS

(75) Inventor: Stefan Miller, Regensburg (DE)

(73) Assignee: LYSANDO AG, Triesenberg (LI)

( * ) Notice: Subject to any disclaimer, the term of this patent is extended or adjusted under 35 U.S.C. 154(b) by 301 days.

This patent is subject to a terminal disclaimer.

(21) Appl. No.: 13/643,900

(22) PCT Filed: Apr. 27, 2011

(86) PCT No.: PCT/EP2011/056657
§ 371 (c)(1),
(2), (4) Date: Nov. 1, 2012

(87) PCT Pub. No.: WO2011/134998
PCT Pub. Date: Nov. 3, 2011

(65) Prior Publication Data
US 2013/0052182 A1   Feb. 28, 2013

(30) Foreign Application Priority Data

Apr. 27, 2010   (EP) .................................... 10161170

(51) Int. Cl.
| C12N 9/14 | (2006.01) |
| --- | --- |
| A61K 38/16 | (2006.01) |
| C12N 15/62 | (2006.01) |
| C12N 9/36 | (2006.01) |
| C12N 9/52 | (2006.01) |

(52) U.S. Cl.
CPC ............. *C12N 15/62* (2013.01); *C12N 9/2462* (2013.01); *C12N 9/52* (2013.01)

(58) Field of Classification Search
None
See application file for complete search history.

(56) References Cited

FOREIGN PATENT DOCUMENTS

| JP | 2010-502735 | 1/2010 |
| --- | --- | --- |
| WO | WO 2008/030988 | 3/2008 |
| WO | WO 2010/023207 | 3/2010 |
| WO | WO 2010/112848 | 10/2010 |

OTHER PUBLICATIONS

Arima, et al., "Bactericidal action of lysozymes attached with various sizes of hydrophobic peptides to the c-terminal using genetic modification," *FEBS Letters*, 415(1):114-118, 1997.

Cheng, et al., "Removal of group B streptococci colonizing the vagina and oropharynx of mice with a bacteriophage lytic enzyme," *Antimicob Agents Chemother.*, 49(1):111-7, 2005.

Donovan, et al., "Petidoglycan hydrolase fusions maintain their parental specificities," *Applied and Environmental Microbiology*, 72(4):2988-2990, 2006.

Kumar, et al., "Significance of microbial biofilms in food industry: a review," *International Journal of Food Microbiology*, 42(1-2):9-27, 1998.

Loeffler, et al., "Rapid killing of Streptococcus pneumonia with bacteriophage cell wall hydrolase," *Science*, 294(5549):2170-2, 2001.

Lopez, et al., "Enzymes for anti-infective therapy: phage lysins," *Drug Discovery Today: Therapeutic Strategies*, 1(4):469-474, 2004.

Nelson, et al., "Prevention and elimination of upper respiratory colonization of mice by group A streptococci by using a bacteriophage lytic enzyme," *PNAS*, 98(7):4107-12, 2001.

PCT International Preliminary Report on Patentability issued in International Application No. PCT/EP2011/056657, mailed Jun. 25, 2012.

PCT International Search Report and Written Opinion issued in Internatioi International Application No. PCT/EP2011/056657, mailed Aug. 8, 2011.

Rashel, et al., "Efficient elimination of multidrug-resistant Staphylococcus aureus by cloned lysine derived from bacteriophage phi MR11," *J Infect Dis.*, 196(8):1237-47, 2007.

Schuch, et al., "A bacteriolytic agent that detects and kills Bacillus anthracis," *Nature*, 418(6900):884-9, 2002.

Vollmer, et al., "Bacterial peptidoglycan (murein) hydrolases," *FEMS Microbiol Rev.*, 32(2):259-86, 2008.

*Primary Examiner* — Padma V Baskar

(74) *Attorney, Agent, or Firm* — Parker Highlander PLLC

(57) ABSTRACT

The present invention relates to methods of eliminating, reducing or preventing bacterial biofilms by means of a fusion protein comprising an endolysin, an autolysin or a bacteriocin to which a peptide with membrane or LPS disrupting activity is fused. Further, the present invention relates to fusion proteins for use as a medicament, in particular for the treatment or prevention of Gram-negative and/or Gram-positive bacterial infections associated with bacterial biofilm, as diagnostic means, disinfectant or as cosmetic substance. The present invention also relates to the removal or reduction or prevention of Gram-negative and/or Gram-positive bacterial contamination associated with bacterial biofilm of foodstuff, of food processing equipment, of food processing plants, of surfaces coming into contact with foodstuff, of medical devices, of surfaces in hospitals and surgeries. Furthermore, the present invention relates to the use of said fusion protein as a diagnostic means in medicinal, food or feed or environmental diagnostic associated with bacterial biofilm.

16 Claims, 17 Drawing Sheets

SEQUENCE LISTING

<160> NUMBER OF SEQ ID NOS: 142

<210> SEQ ID NO 1

<211> LENGTH: 260
<212> TYPE: PRT
<213> ORGANISM: unknown
<220> FEATURE:
<223> OTHER INFORMATION: phiKZgp144

<400> SEQUENCE: 1

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Ile Lys Ala Lys Thr Ser Ser
            115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
                180                 185                 190

Asp Thr Asp Leu Tyr Leu Ala His Phe Phe Gly Pro Gly Ala Ala Arg
            195                 200                 205

Arg Phe Leu Thr Thr Gly Gln Asn Glu Leu Ala Ala Thr His Phe Pro
    210                 215                 220

Lys Glu Ala Gln Ala Asn Pro Ser Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
        260

<210> SEQ ID NO 2
<211> LENGTH: 292
<212> TYPE: PRT
<213> ORGANISM: unknown
<220> FEATURE:
<223> OTHER INFORMATION: ELgp188

<400> SEQUENCE: 2

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
                20                  25                  30

Gly Thr Ser Ser Ser Thr Glu Thr Leu Leu Arg Gly Tyr Ala Glu Val
            35                  40                  45

Val Gly Lys Asn Thr Gly Gly Ile Gly Leu Pro Thr Thr Ser Asp Ala

```
                    50                  55                  60
Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                 85                  90                  95

Ser Gly Leu Asp Lys Ala Phe Glu Val Tyr Lys Glu Arg Tyr Arg Thr
                100                 105                 110

Pro Thr Tyr Asp Ile Ala Trp Ser Gly Lys Val Ser Pro Ala Phe Thr
                115                 120                 125

Ala Lys Val Lys Asp Trp Cys Gly Val His Val Pro Asn His Arg Ala
            130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
                180                 185                 190

Ile Arg Ser Met Asp Gln Leu Thr Gln Leu Asp Leu Val Phe Lys Tyr
                195                 200                 205

Phe Glu Met Trp Met Lys Arg Gly Lys Arg Tyr Thr Gln Leu Glu Asp
210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
                260                 265                 270

Thr Leu Tyr Thr Thr Tyr Tyr Lys Gly Leu Leu Pro Glu Asn Arg His
                275                 280                 285

Val Ile Ser Tyr
            290

<210> SEQ ID NO 3
<211> LENGTH: 181
<212> TYPE: PRT
<213> ORGANISM: unknown
<220> FEATURE:
<223> OTHER INFORMATION: Salmonella endolysin

<400> SEQUENCE: 3

Met Lys Pro Lys Asp Glu Ile Phe Asp Glu Ile Leu Gly Lys Glu Gly
 1               5                  10                  15

Gly Tyr Val Asn His Pro Asp Asp Lys Gly Gly Pro Thr Lys Trp Gly
                20                  25                  30

Ile Thr Glu Lys Val Ala Arg Ala His Gly Tyr Arg Gly Asp Met Arg
            35                  40                  45

Asn Leu Thr Arg Gly Gln Ala Leu Glu Ile Leu Glu Thr Asp Tyr Trp
        50                  55                  60

Tyr Gly Pro Arg Phe Asp Arg Val Ala Lys Ala Ser Pro Asp Val Ala
 65                  70                  75                  80

Ala Glu Leu Cys Asp Thr Gly Val Asn Met Gly Pro Ser Val Ala Ala
                85                  90                  95

Lys Met Leu Gln Arg Trp Leu Asn Val Phe Asn Gln Gly Gly Arg Leu
                100                 105                 110

Tyr Pro Asp Met Asp Thr Asp Gly Arg Ile Gly Pro Arg Thr Leu Asn
```

```
            115                 120                 125
Ala Leu Arg Val Tyr Leu Glu Lys Arg Gly Lys Asp Gly Glu Arg Val
        130                 135                 140

Leu Leu Val Ala Leu Asn Cys Thr Gln Gly Glu Arg Tyr Leu Glu Leu
145                 150                 155                 160

Ala Glu Lys Arg Glu Ala Asp Glu Ser Phe Val Tyr Gly Trp Met Lys
                165                 170                 175

Glu Arg Val Leu Ile
            180

<210> SEQ ID NO 4
<211> LENGTH: 163
<212> TYPE: PRT
<213> ORGANISM: unknown
<220> FEATURE:
<223> OTHER INFORMATION: Enterobacteria phage T4 endolysin

<400> SEQUENCE: 4

Met Asn Ile Phe Glu Met Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
            20                  25                  30

Leu Thr Lys Ser Pro Ser Leu Asn Ala Ala Lys Ser Glu Leu Asp Lys
        35                  40                  45

Ala Ile Gly Arg Asn Cys Asn Gly Val Ile Thr Lys Asp Glu Ala Glu
    50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95

Cys Ala Leu Ile Asn Met Val Phe Gln Met Gly Glu Thr Gly Val Ala
            100                 105                 110

Gly Phe Thr Asn Ser Leu Arg Met Leu Gln Gln Lys Arg Trp Asp Glu
        115                 120                 125

Ala Ala Val Asn Leu Ala Lys Ser Arg Trp Tyr Asn Gln Thr Pro Asn
    130                 135                 140

Arg Ala Lys Arg Val Ile Thr Thr Phe Arg Thr Gly Thr Trp Asp Ala
145                 150                 155                 160

Tyr Lys Asn

<210> SEQ ID NO 5
<211> LENGTH: 280
<212> TYPE: PRT
<213> ORGANISM: unknown
<220> FEATURE:
<223> OTHER INFORMATION: Acinetobacter baumanii endolysin

<400> SEQUENCE: 5

Met Glu Tyr Asp Met Ile Leu Lys Phe Gly Ser Lys Gly Asp Ala Val
1               5                   10                  15

Ala Thr Leu Gln Lys Gln Leu Ala Lys Met Gly Tyr Lys Gly Val Lys
            20                  25                  30

Asp Lys Pro Leu Ser Val Asp Gly His Phe Gly Glu Ser Thr Glu Phe
        35                  40                  45

Ala Val Ile Gln Leu Gln Arg Lys Phe Gly Leu Val Ala Asp Gly Lys
    50                  55                  60

Val Gly Asp Lys Thr Arg Gln Ala Leu Ala Gly Asp Ser Val Ser Lys
```

```
                65                  70                  75                  80
        Phe Leu Lys Asp Glu Asp Tyr Lys Lys Ala Ala Ile Arg Leu Lys Val
                            85                  90                  95

Pro Glu Leu Val Ile Arg Val Phe Gly Ala Val Glu Gly Leu Gly Val
                        100                 105                 110

Gly Phe Leu Pro Asn Gly Lys Ala Lys Ile Leu Phe Glu Arg His Arg
                    115                 120                 125

Met Tyr Phe Tyr Leu Cys Gln Ala Leu Gly Lys Thr Phe Ala Asn Ser
                130                 135                 140

Gln Val Lys Ile Thr Pro Asn Ile Val Asn Thr Leu Thr Gly Gly Tyr
        145                 150                 155                 160

Lys Gly Asp Ala Ala Glu Tyr Thr Arg Leu Ser Met Ala Ile Asn Ile
                            165                 170                 175

His Lys Glu Ser Ala Leu Met Ser Thr Ser Trp Gly Gln Phe Gln Ile
                        180                 185                 190

Met Gly Glu Asn Trp Lys Asp Leu Gly Tyr Ser Ser Val Gln Glu Phe
                    195                 200                 205

Val Asp Gln Gln Gln Leu Asn Glu Gly Asn Gln Leu Glu Ala Phe Ile
                210                 215                 220

Arg Phe Ile Glu Trp Lys Pro Gly Leu Leu Glu Ala Leu Arg Lys Gln
        225                 230                 235                 240

Asp Trp Asp Thr Val Phe Thr Leu Tyr Asn Gly Lys Asn Tyr Lys Lys
                            245                 250                 255

Leu Gly Tyr Gln Ala Lys Phe Gln Lys Glu Trp Asp His Leu Glu Pro
                        260                 265                 270

Ile Tyr Arg Glu Lys Thr Ala Ala
                    275                 280

<210> SEQ ID NO 6
<211> LENGTH: 152
<212> TYPE: PRT
<213> ORGANISM: unknown
<220> FEATURE:
<223> OTHER INFORMATION: E. coli K1F endolysin

<400> SEQUENCE: 6

Met Val Ser Lys Val Gln Phe Asn Pro Arg Ser Arg Thr Asp Ala Ile
        1               5                   10                  15

Phe Val His Cys Ser Ala Thr Lys Pro Glu Met Asp Ile Gly Val Glu
                            20                  25                  30

Thr Ile Arg Met Trp His Lys Gln Gln Ala Trp Leu Asp Val Gly Tyr
                        35                  40                  45

His Phe Ile Ile Lys Arg Asp Gly Thr Val Glu Glu Gly Arg Pro Val
                    50                  55                  60

Asn Val Val Gly Ser His Val Lys Asp Trp Asn Ser Arg Ser Val Gly
        65                  70                  75                  80

Val Cys Leu Val Gly Gly Ile Asn Ala Lys Gly Gln Phe Glu Ala Asn
                            85                  90                  95

Phe Thr Pro Ala Gln Met Asn Ser Leu Arg Asn Lys Leu Asp Asp Leu
                        100                 105                 110

Lys Val Met Tyr Pro Gln Ala Glu Ile Arg Ala His His Asp Val Ala
                    115                 120                 125

Pro Lys Ala Cys Pro Ser Phe Asp Leu Gln Arg Trp Leu Ser Thr Asn
        130                 135                 140

Glu Leu Val Thr Ser Asp Arg Gly
                            145                 150
```

```
145                 150

<210> SEQ ID NO 7
<211> LENGTH: 328
<212> TYPE: PRT
<213> ORGANISM: unknown
<220> FEATURE:
<223> OTHER INFORMATION: OBPgpLYS

<400> SEQUENCE: 7

Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
145                 150                 155                 160

Ile Asn Thr Pro Leu Arg Ile Ala His Phe Met Ala Gln Ile Leu His
                165                 170                 175

Glu Thr Ala Cys Phe Lys Tyr Thr Glu Glu Leu Ala Ser Gly Lys Ala
            180                 185                 190

Tyr Glu Gly Arg Ala Asp Leu Gly Asn Thr Arg Pro Gly Asp Gly Pro
        195                 200                 205

Leu Phe Lys Gly Arg Gly Leu Leu Gln Ile Thr Gly Arg Leu Asn Tyr
    210                 215                 220

Val Lys Cys Gln Val Tyr Leu Arg Glu Lys Leu Lys Asp Pro Thr Phe
225                 230                 235                 240

Asp Ile Thr Ser Ser Val Thr Cys Ala Gln Gln Leu Ser Glu Ser Pro
                245                 250                 255

Leu Leu Ala Ala Leu Ala Ser Gly Tyr Phe Trp Arg Phe Ile Lys Pro
            260                 265                 270

Lys Leu Asn Glu Thr Ala Asp Lys Asp Ile Tyr Trp Val Ser Val
        275                 280                 285

Tyr Val Asn Gly Tyr Ala Lys Gln Ala Asn Pro Tyr Tyr Pro Asn Arg
    290                 295                 300

Asp Lys Glu Pro Asn His Met Lys Glu Arg Val Gln Met Leu Ala Val
305                 310                 315                 320

Thr Lys Lys Ala Leu Gly Ile Val
                325

<210> SEQ ID NO 8
<211> LENGTH: 165
<212> TYPE: PRT
```

```
<213> ORGANISM: unknown
<220> FEATURE:
<223> OTHER INFORMATION: PSP3gp10

<400> SEQUENCE: 8

Met Pro Val Ile Asn Thr His Gln Asn Ile Ala Ala Phe Leu Asp Met
1               5                   10                  15

Leu Ala Tyr Ser Glu Gly Thr Ala Asn His Pro Leu Thr Lys Asn Arg
                20                  25                  30

Gly Tyr Asp Val Ile Val Thr Gly Phe Asp Gly Ser Pro Glu Ile Phe
            35                  40                  45

Thr Asp Tyr Ser Asp His Pro Phe Ala His Gly Arg Pro Pro Lys Val
        50                  55                  60

Phe Asn Arg Arg Gly Glu Lys Ser Thr Ala Ser Gly Arg Tyr Gln Gln
65                  70                  75                  80

Leu Tyr Ile Phe Trp Pro His Tyr Lys Lys Gln Leu Ala Leu Pro Asp
                85                  90                  95

Phe Ser Pro Leu Ser Gln Asp Lys Leu Ala Ile Gln Leu Ile Arg Glu
            100                 105                 110

Arg Gly Ala Ile Asp Asp Ile Arg Ala Gly Arg Ile Glu Arg Ala Val
        115                 120                 125

Ser Arg Cys Arg Asn Ile Trp Ala Ser Leu Pro Gly Ala Gly Tyr Gly
    130                 135                 140

Gln Arg Glu His Ser Leu Glu Lys Leu Val Thr Val Trp Arg Thr Ala
145                 150                 155                 160

Gly Gly Val Met Ala
                165

<210> SEQ ID NO 9
<211> LENGTH: 165
<212> TYPE: PRT
<213> ORGANISM: unknown
<220> FEATURE:
<223> OTHER INFORMATION: P2gp09

<400> SEQUENCE: 9

Met Pro Val Ile Asn Thr His Gln Asn Ile Ala Ala Phe Leu Asp Met
1               5                   10                  15

Leu Ala Val Ser Glu Gly Thr Ala Asn His Pro Leu Thr Lys Asn Arg
                20                  25                  30

Gly Tyr Asp Val Ile Val Thr Gly Leu Asp Gly Lys Pro Glu Ile Phe
            35                  40                  45

Thr Asp Tyr Ser Asp His Pro Phe Ala His Gly Arg Pro Ala Lys Val
        50                  55                  60

Phe Asn Arg Arg Gly Glu Lys Ser Thr Ala Ser Gly Arg Tyr Gln Gln
65                  70                  75                  80

Leu Tyr Leu Phe Trp Pro His Tyr Arg Lys Gln Leu Ala Leu Pro Asp
                85                  90                  95

Phe Ser Pro Leu Ser Gln Asp Arg Leu Ala Ile Gln Leu Ile Arg Glu
            100                 105                 110

Arg Gly Ala Leu Asp Asp Ile Arg Ala Gly Arg Ile Glu Arg Ala Ile
        115                 120                 125

Ser Arg Cys Arg Asn Ile Trp Ala Ser Leu Pro Gly Ala Gly Tyr Gly
    130                 135                 140

Gln Arg Glu His Ser Leu Glu Lys Leu Val Thr Val Trp Arg Thr Ala
145                 150                 155                 160
```

Gly Gly Val Pro Ala
            165

<210> SEQ ID NO 10
<211> LENGTH: 6
<212> TYPE: PRT
<213> ORGANISM: unknown
<220> FEATURE:
<223> OTHER INFORMATION: synthetic peptide

<400> SEQUENCE: 10

Lys Arg Lys Lys Arg Lys
1               5

<210> SEQ ID NO 11
<211> LENGTH: 9
<212> TYPE: PRT
<213> ORGANISM: unknown
<220> FEATURE:
<223> OTHER INFORMATION: synthetic peptide

<400> SEQUENCE: 11

Lys Arg Lys Lys Arg Lys Lys Arg Lys
1               5

<210> SEQ ID NO 12
<211> LENGTH: 9
<212> TYPE: PRT
<213> ORGANISM: unknown
<220> FEATURE:
<223> OTHER INFORMATION: synthetic peptide

<400> SEQUENCE: 12

Arg Arg Arg Arg Arg Arg Arg Arg Arg
1               5

<210> SEQ ID NO 13
<211> LENGTH: 8
<212> TYPE: PRT
<213> ORGANISM: unknown
<220> FEATURE:
<223> OTHER INFORMATION: synthetic peptide

<400> SEQUENCE: 13

Lys Lys Lys Lys Lys Lys Lys Lys
1               5

<210> SEQ ID NO 14
<211> LENGTH: 10
<212> TYPE: PRT
<213> ORGANISM: unknown
<220> FEATURE:
<223> OTHER INFORMATION: synthetic peptide

<400> SEQUENCE: 14

Lys Arg Lys Lys Arg Lys Lys Arg Lys Lys
1               5                   10

<210> SEQ ID NO 15
<211> LENGTH: 12
<212> TYPE: PRT
<213> ORGANISM: unknown
<220> FEATURE:
<223> OTHER INFORMATION: synthetic peptide

<400> SEQUENCE: 15

Lys Arg Lys Lys Arg Lys Lys Arg Lys Lys Arg Lys

```
1               5               10
```

<210> SEQ ID NO 16
<211> LENGTH: 14
<212> TYPE: PRT
<213> ORGANISM: unknown
<220> FEATURE:
<223> OTHER INFORMATION: synthetic peptide

<400> SEQUENCE: 16

```
Lys Arg Lys Lys Arg Lys Lys Arg Lys Lys Arg Lys Lys Arg
1               5                   10
```

<210> SEQ ID NO 17
<211> LENGTH: 16
<212> TYPE: PRT
<213> ORGANISM: unknown
<220> FEATURE:
<223> OTHER INFORMATION: synthetic peptide

<400> SEQUENCE: 17

```
Lys Lys Lys Lys Lys Lys Lys Lys Lys Lys Lys Lys Lys Lys Lys Lys
1               5                   10                  15
```

<210> SEQ ID NO 18
<211> LENGTH: 19
<212> TYPE: PRT
<213> ORGANISM: unknown
<220> FEATURE:
<223> OTHER INFORMATION: synthetic peptide

<400> SEQUENCE: 18

```
Lys Arg Lys Lys Arg Lys Lys Arg Lys Lys Arg Lys Lys Arg Lys Lys
1               5                   10                  15

Arg Lys Lys
```

<210> SEQ ID NO 19
<211> LENGTH: 19
<212> TYPE: PRT
<213> ORGANISM: unknown
<220> FEATURE:
<223> OTHER INFORMATION: synthetic peptide

<400> SEQUENCE: 19

```
Arg Arg Arg Arg Arg Arg Arg Arg Arg Arg Arg Arg Arg Arg Arg Arg
1               5                   10                  15

Arg Arg Arg
```

<210> SEQ ID NO 20
<211> LENGTH: 19
<212> TYPE: PRT
<213> ORGANISM: unknown
<220> FEATURE:
<223> OTHER INFORMATION: synthetic peptide

<400> SEQUENCE: 20

```
Lys Lys Lys Lys Lys Lys Lys Lys Lys Lys Lys Lys Lys Lys Lys Lys
1               5                   10                  15

Lys Lys Lys
```

<210> SEQ ID NO 21
<211> LENGTH: 20
<212> TYPE: PRT
<213> ORGANISM: unknown
<220> FEATURE:

<223> OTHER INFORMATION: synthetic peptide

<400> SEQUENCE: 21

Lys Arg Lys Lys Arg Lys Lys Arg Lys Arg Ser Lys Arg Lys Lys Arg
1               5                   10                  15

Lys Lys Arg Lys
            20

<210> SEQ ID NO 22
<211> LENGTH: 21
<212> TYPE: PRT
<213> ORGANISM: unknown
<220> FEATURE:
<223> OTHER INFORMATION: synthetic peptide

<400> SEQUENCE: 22

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 23
<211> LENGTH: 21
<212> TYPE: PRT
<213> ORGANISM: unknown
<220> FEATURE:
<223> OTHER INFORMATION: synthetic peptide

<400> SEQUENCE: 23

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 24
<211> LENGTH: 22
<212> TYPE: PRT
<213> ORGANISM: unknown
<220> FEATURE:
<223> OTHER INFORMATION: synthetic peptide

<400> SEQUENCE: 24

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 25
<211> LENGTH: 24
<212> TYPE: PRT
<213> ORGANISM: unknown
<220> FEATURE:
<223> OTHER INFORMATION: synthetic peptide

<400> SEQUENCE: 25

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 26
<211> LENGTH: 25
<212> TYPE: PRT
<213> ORGANISM: unknown

```
<220> FEATURE:
<223> OTHER INFORMATION: synthetic peptide

<400> SEQUENCE: 26

Lys Arg Lys Lys Arg Lys Lys Arg Lys Lys Arg Lys Lys Arg Lys Lys
1               5                   10                  15
Arg Lys Lys Arg Lys Lys Arg Lys Lys
            20                  25

<210> SEQ ID NO 27
<211> LENGTH: 31
<212> TYPE: PRT
<213> ORGANISM: unknown
<220> FEATURE:
<223> OTHER INFORMATION: synthetic peptide

<400> SEQUENCE: 27

Lys Arg Lys Lys Arg Lys Lys Arg Lys Arg Ser Lys Arg Lys Lys Arg
1               5                   10                  15
Lys Lys Arg Lys Arg Ser Lys Arg Lys Lys Arg Lys Lys Arg Lys
            20                  25                  30

<210> SEQ ID NO 28
<211> LENGTH: 38
<212> TYPE: PRT
<213> ORGANISM: unknown
<220> FEATURE:
<223> OTHER INFORMATION: synthetic peptide

<400> SEQUENCE: 28

Lys Arg Lys Lys Arg Lys Lys Arg Lys Arg Gly Ser Gly Ser Gly Lys
1               5                   10                  15
Arg Lys Lys Arg Lys Lys Arg Lys Gly Ser Gly Ser Gly Lys Arg Lys
            20                  25                  30
Lys Arg Lys Lys Arg Lys
        35

<210> SEQ ID NO 29
<211> LENGTH: 39
<212> TYPE: PRT
<213> ORGANISM: unknown
<220> FEATURE:
<223> OTHER INFORMATION: synthetic peptide

<400> SEQUENCE: 29

Lys Arg Lys Lys Arg Lys Lys Arg Lys Lys Arg Lys Lys Arg Lys Lys
1               5                   10                  15
Arg Lys Lys Arg Lys Lys Arg Lys Lys Arg Lys Lys Arg Lys Lys Arg
            20                  25                  30
Lys Lys Arg Lys Lys Arg Lys
        35

<210> SEQ ID NO 30
<211> LENGTH: 42
<212> TYPE: PRT
<213> ORGANISM: unknown
<220> FEATURE:
<223> OTHER INFORMATION: synthetic peptide

<400> SEQUENCE: 30

Lys Arg Lys Lys Arg Lys Lys Arg Lys Arg Ser Lys Arg Lys Lys Arg
1               5                   10                  15
Lys Lys Arg Lys Arg Ser Lys Arg Lys Lys Arg Lys Lys Arg Lys Arg
```

```
                    20                  25                  30
Ser Lys Arg Lys Lys Arg Lys Lys Arg Lys
        35                  40

<210> SEQ ID NO 31
<211> LENGTH: 4
<212> TYPE: PRT
<213> ORGANISM: unknown
<220> FEATURE:
<223> OTHER INFORMATION: synthetic peptide

<400> SEQUENCE: 31

Ala Met Ser Gly
1

<210> SEQ ID NO 32
<211> LENGTH: 5
<212> TYPE: PRT
<213> ORGANISM: unknown
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: wherein Xaa is any other amino acid residue
      than lysine, arginine and histidine

<400> SEQUENCE: 32

Lys Arg Xaa Lys Arg
1               5

<210> SEQ ID NO 33
<211> LENGTH: 5
<212> TYPE: PRT
<213> ORGANISM: unknown
<220> FEATURE:
<223> OTHER INFORMATION: synthetic peptide

<400> SEQUENCE: 33

Lys Arg Ser Lys Arg
1               5

<210> SEQ ID NO 34
<211> LENGTH: 5
<212> TYPE: PRT
<213> ORGANISM: unknown
<220> FEATURE:
<223> OTHER INFORMATION: synthetic peptide

<400> SEQUENCE: 34

Lys Arg Gly Ser Gly
1               5

<210> SEQ ID NO 35
<211> LENGTH: 271
<212> TYPE: PRT
<213> ORGANISM: unknown
<220> FEATURE:
<223> OTHER INFORMATION: POLY-gp144

<400> SEQUENCE: 35

Met Gly Ser Lys Arg Lys Lys Arg Lys Lys Arg Lys Lys Val Leu Arg
1               5                   10                  15

Lys Gly Asp Arg Gly Asp Glu Val Cys Gln Leu Gln Thr Leu Leu Asn
                20                  25                  30

Leu Cys Gly Tyr Asp Val Gly Lys Pro Asp Gly Ile Phe Gly Asn Asn
```

```
                35                  40                  45
Thr Phe Asn Gln Val Val Lys Phe Gln Lys Asp Asn Cys Leu Asp Ser
 50                  55                  60

Asp Gly Ile Val Gly Lys Asn Thr Trp Ala Glu Leu Phe Ser Lys Tyr
 65                  70                  75                  80

Ser Pro Pro Ile Pro Tyr Lys Thr Ile Pro Met Pro Thr Ala Asn Lys
                 85                  90                  95

Ser Arg Ala Ala Ala Thr Pro Val Met Asn Ala Val Glu Asn Ala Thr
                100                 105                 110

Gly Val Arg Ser Gln Leu Leu Leu Thr Phe Ala Ser Ile Glu Ser Ala
            115                 120                 125

Phe Asp Tyr Glu Ile Lys Ala Lys Thr Ser Ser Ala Thr Gly Trp Phe
130                 135                 140

Gln Phe Leu Thr Gly Thr Trp Lys Thr Met Ile Glu Asn Tyr Gly Met
145                 150                 155                 160

Lys Tyr Gly Val Leu Thr Asp Pro Thr Gly Ala Leu Arg Lys Asp Pro
                165                 170                 175

Arg Ile Ser Ala Leu Met Gly Ala Glu Leu Ile Lys Glu Asn Met Asn
                180                 185                 190

Ile Leu Arg Pro Val Leu Lys Arg Glu Pro Thr Asp Thr Asp Leu Tyr
            195                 200                 205

Leu Ala His Phe Phe Gly Pro Gly Ala Ala Arg Arg Phe Leu Thr Thr
210                 215                 220

Gly Gln Asn Glu Leu Ala Ala Thr His Phe Pro Lys Glu Ala Gln Ala
225                 230                 235                 240

Asn Pro Ser Ile Phe Tyr Asn Lys Asp Gly Ser Pro Lys Thr Ile Gln
                245                 250                 255

Glu Val Tyr Asn Leu Met Asp Gly Lys Val Ala Ala His Arg Lys
                260                 265                 270

<210> SEQ ID NO 36
<211> LENGTH: 282
<212> TYPE: PRT
<213> ORGANISM: unknown
<220> FEATURE:
<223> OTHER INFORMATION: (POLY)2-gp144

<400> SEQUENCE: 36

Met Gly Ser Lys Arg Lys Lys Arg Lys Lys Arg Lys Arg Ser Lys Arg
 1               5                  10                  15

Lys Lys Arg Lys Lys Arg Lys Lys Val Leu Arg Lys Gly Asp Arg Gly
                20                  25                  30

Asp Glu Val Cys Gln Leu Gln Thr Leu Leu Asn Leu Cys Gly Tyr Asp
                35                  40                  45

Val Gly Lys Pro Asp Gly Ile Phe Gly Asn Asn Thr Phe Asn Gln Val
 50                  55                  60

Val Lys Phe Gln Lys Asp Asn Cys Leu Asp Ser Asp Gly Ile Val Gly
 65                  70                  75                  80

Lys Asn Thr Trp Ala Glu Leu Phe Ser Lys Tyr Ser Pro Pro Ile Pro
                 85                  90                  95

Tyr Lys Thr Ile Pro Met Pro Thr Ala Asn Lys Ser Arg Ala Ala Ala
                100                 105                 110

Thr Pro Val Met Asn Ala Val Glu Asn Ala Thr Gly Val Arg Ser Gln
            115                 120                 125

Leu Leu Leu Thr Phe Ala Ser Ile Glu Ser Ala Phe Asp Tyr Glu Ile
```

```
        130                 135                 140
Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
        195                 200                 205

Leu Lys Arg Glu Pro Thr Asp Thr Asp Leu Tyr Leu Ala His Phe Phe
    210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
            260                 265                 270

Met Asp Gly Lys Val Ala Ala His Arg Lys
        275                 280

<210> SEQ ID NO 37
<211> LENGTH: 293
<212> TYPE: PRT
<213> ORGANISM: unknown
<220> FEATURE:
<223> OTHER INFORMATION: (POLY)3-gp144

<400> SEQUENCE: 37

Met Gly Ser Lys Arg Lys Lys Arg Lys Arg Ser Lys Arg
1               5                   10                  15

Lys Lys Arg Lys Lys Arg Lys Ser Lys Arg Lys Lys Lys
                20                  25                  30

Arg Lys Lys Val Leu Arg Lys Gly Asp Arg Gly Asp Glu Val Cys Gln
            35                  40                  45

Leu Gln Thr Leu Leu Asn Leu Cys Gly Tyr Asp Val Gly Lys Pro Asp
    50                  55                  60

Gly Ile Phe Gly Asn Asn Thr Phe Asn Gln Val Val Lys Phe Gln Lys
65                  70                  75                  80

Asp Asn Cys Leu Asp Ser Asp Gly Ile Val Gly Lys Asn Thr Trp Ala
                85                  90                  95

Glu Leu Phe Ser Lys Tyr Ser Pro Pro Ile Pro Tyr Lys Thr Ile Pro
            100                 105                 110

Met Pro Thr Ala Asn Lys Ser Arg Ala Ala Thr Pro Val Met Asn
        115                 120                 125

Ala Val Glu Asn Ala Thr Gly Val Arg Ser Gln Leu Leu Thr Phe
    130                 135                 140

Ala Ser Ile Glu Ser Ala Phe Asp Tyr Glu Ile Lys Ala Lys Thr Ser
145                 150                 155                 160

Ser Ala Thr Gly Trp Phe Gln Phe Leu Thr Gly Thr Trp Lys Thr Met
                165                 170                 175

Ile Glu Asn Tyr Gly Met Lys Tyr Gly Val Leu Thr Asp Pro Thr Gly
            180                 185                 190

Ala Leu Arg Lys Asp Pro Arg Ile Ser Ala Leu Met Gly Ala Glu Leu
        195                 200                 205

Ile Lys Glu Asn Met Asn Ile Leu Arg Pro Val Leu Lys Arg Glu Pro
```

```
                       210                 215                 220

Thr Asp Thr Asp Leu Tyr Leu Ala His Phe Phe Gly Pro Gly Ala Ala
225                 230                 235                 240

Arg Arg Phe Leu Thr Thr Gly Gln Asn Glu Leu Ala Ala Thr His Phe
                245                 250                 255

Pro Lys Glu Ala Gln Ala Asn Pro Ser Ile Phe Tyr Asn Lys Asp Gly
                260                 265                 270

Ser Pro Lys Thr Ile Gln Glu Val Tyr Asn Leu Met Asp Gly Lys Val
            275                 280                 285

Ala Ala His Arg Lys
        290

<210> SEQ ID NO 38
<211> LENGTH: 304
<212> TYPE: PRT
<213> ORGANISM: unknown
<220> FEATURE:
<223> OTHER INFORMATION: (POLY)4-gp144

<400> SEQUENCE: 38

Met Gly Ser Lys Arg Lys Lys Arg Lys Lys Arg Lys Arg Ser Lys Arg
1               5                   10                  15

Lys Lys Arg Lys Lys Arg Lys Arg Ser Lys Arg Lys Lys Arg Lys Lys
                20                  25                  30

Arg Lys Arg Ser Lys Arg Lys Lys Arg Lys Arg Lys Lys Val Leu
                35                  40                  45

Arg Lys Gly Asp Arg Gly Asp Glu Val Cys Gln Leu Gln Thr Leu Leu
            50                  55                  60

Asn Leu Cys Gly Tyr Asp Val Gly Lys Pro Asp Gly Ile Phe Gly Asn
65                  70                  75                  80

Asn Thr Phe Asn Gln Val Val Lys Phe Gln Lys Asp Asn Cys Leu Asp
                85                  90                  95

Ser Asp Gly Ile Val Gly Lys Asn Thr Trp Ala Glu Leu Phe Ser Lys
                100                 105                 110

Tyr Ser Pro Pro Ile Pro Tyr Lys Thr Ile Pro Met Pro Thr Ala Asn
                115                 120                 125

Lys Ser Arg Ala Ala Thr Pro Val Met Asn Ala Val Glu Asn Ala
            130                 135                 140

Thr Gly Val Arg Ser Gln Leu Leu Leu Thr Phe Ala Ser Ile Glu Ser
145                 150                 155                 160

Ala Phe Asp Tyr Glu Ile Lys Ala Lys Thr Ser Ser Ala Thr Gly Trp
                165                 170                 175

Phe Gln Phe Leu Thr Gly Thr Trp Lys Thr Met Ile Glu Asn Tyr Gly
                180                 185                 190

Met Lys Tyr Gly Val Leu Thr Asp Pro Thr Gly Ala Leu Arg Lys Asp
            195                 200                 205

Pro Arg Ile Ser Ala Leu Met Gly Ala Glu Leu Ile Lys Glu Asn Met
            210                 215                 220

Asn Ile Leu Arg Pro Val Leu Lys Arg Glu Pro Thr Asp Thr Asp Leu
225                 230                 235                 240

Tyr Leu Ala His Phe Phe Gly Pro Gly Ala Ala Arg Arg Phe Leu Thr
                245                 250                 255

Thr Gly Gln Asn Glu Leu Ala Ala Thr His Phe Pro Lys Glu Ala Gln
                260                 265                 270

Ala Asn Pro Ser Ile Phe Tyr Asn Lys Asp Gly Ser Pro Lys Thr Ile
```

```
            275                 280                 285
Gln Glu Val Tyr Asn Leu Met Asp Gly Lys Val Ala Ala His Arg Lys
    290                 295                 300

<210> SEQ ID NO 39
<211> LENGTH: 303
<212> TYPE: PRT
<213> ORGANISM: unknown
<220> FEATURE:
<223> OTHER INFORMATION: POLY-gp188

<400> SEQUENCE: 39

Met Gly Ser Lys Arg Lys Lys Arg Lys Lys Arg Lys Asn Phe Arg Thr
1               5                   10                  15

Lys Asn Gly Tyr Arg Asp Leu Gln Ala Leu Val Lys Glu Leu Gly Leu
            20                  25                  30

Tyr Thr Gly Gln Ile Asp Gly Val Trp Gly Lys Gly Thr Ser Ser Ser
        35                  40                  45

Thr Glu Thr Leu Leu Arg Gly Tyr Ala Glu Val Val Gly Lys Asn Thr
    50                  55                  60

Gly Gly Ile Gly Leu Pro Thr Thr Ser Asp Ala Ser Gly Tyr Asn Val
65                  70                  75                  80

Ile Thr Ala Leu Gln Arg Asn Leu Ala Phe Leu Gly Leu Tyr Ser Leu
                85                  90                  95

Thr Val Asp Gly Ile Trp Gly Asn Gly Thr Leu Ser Gly Leu Asp Lys
            100                 105                 110

Ala Phe Glu Val Tyr Lys Glu Arg Tyr Arg Thr Pro Thr Tyr Asp Ile
        115                 120                 125

Ala Trp Ser Gly Lys Val Ser Pro Ala Phe Thr Ala Lys Val Lys Asp
    130                 135                 140

Trp Cys Gly Val His Val Pro Asn His Arg Ala Pro His Trp Leu Met
145                 150                 155                 160

Ala Cys Met Ala Phe Glu Thr Gly Gln Thr Phe Ser Pro Ser Ile Lys
                165                 170                 175

Asn Ala Ala Gly Ser Glu Ala Tyr Gly Leu Ile Gln Phe Met Ser Pro
            180                 185                 190

Ala Ala Asn Asp Leu Asn Val Pro Leu Ser Val Ile Arg Ser Met Asp
        195                 200                 205

Gln Leu Thr Gln Leu Asp Leu Val Phe Lys Tyr Phe Glu Met Trp Met
    210                 215                 220

Lys Arg Gly Lys Arg Tyr Thr Gln Leu Glu Asp Phe Tyr Leu Thr Ile
225                 230                 235                 240

Phe His Pro Ala Ser Val Gly Lys Lys Ala Asp Glu Val Leu Phe Leu
                245                 250                 255

Gln Gly Ser Lys Ala Tyr Leu Gln Asn Lys Gly Phe Asp Val Asp Lys
            260                 265                 270

Asp Gly Lys Ile Thr Leu Gly Glu Ile Ser Ser Thr Leu Tyr Thr Thr
        275                 280                 285

Tyr Tyr Lys Gly Leu Leu Pro Glu Asn Arg His Val Ile Ser Tyr
    290                 295                 300

<210> SEQ ID NO 40
<211> LENGTH: 314
<212> TYPE: PRT
<213> ORGANISM: unknown
<220> FEATURE:
<223> OTHER INFORMATION: (POLY)2-gp188
```

```
<400> SEQUENCE: 40

Met Gly Ser Lys Arg Lys Lys Arg Lys Lys Arg Ser Lys Arg
1               5                   10                  15

Lys Lys Arg Lys Lys Arg Lys Asn Phe Arg Thr Lys Asn Gly Tyr Arg
            20                  25                  30

Asp Leu Gln Ala Leu Val Lys Glu Leu Gly Leu Tyr Thr Gly Gln Ile
                35                  40                  45

Asp Gly Val Trp Gly Lys Gly Thr Ser Ser Thr Glu Thr Leu Leu
        50                  55                  60

Arg Gly Tyr Ala Glu Val Val Gly Lys Asn Thr Gly Gly Ile Gly Leu
65                  70                  75                  80

Pro Thr Thr Ser Asp Ala Ser Gly Tyr Asn Val Ile Thr Ala Leu Gln
                    85                  90                  95

Arg Asn Leu Ala Phe Leu Gly Leu Tyr Ser Leu Thr Val Asp Gly Ile
                100                 105                 110

Trp Gly Asn Gly Thr Leu Ser Gly Leu Asp Lys Ala Phe Glu Val Tyr
            115                 120                 125

Lys Glu Arg Tyr Arg Thr Pro Thr Tyr Asp Ile Ala Trp Ser Gly Lys
130                 135                 140

Val Ser Pro Ala Phe Thr Ala Lys Val Lys Asp Trp Cys Gly Val His
145                 150                 155                 160

Val Pro Asn His Arg Ala Pro His Trp Leu Met Ala Cys Met Ala Phe
                    165                 170                 175

Glu Thr Gly Gln Thr Phe Ser Pro Ser Ile Lys Asn Ala Ala Gly Ser
                180                 185                 190

Glu Ala Tyr Gly Leu Ile Gln Phe Met Ser Pro Ala Ala Asn Asp Leu
            195                 200                 205

Asn Val Pro Leu Ser Val Ile Arg Ser Met Asp Gln Leu Thr Gln Leu
210                 215                 220

Asp Leu Val Phe Lys Tyr Phe Glu Met Trp Met Lys Arg Gly Lys Arg
225                 230                 235                 240

Tyr Thr Gln Leu Glu Asp Phe Tyr Leu Thr Ile Phe His Pro Ala Ser
                245                 250                 255

Val Gly Lys Lys Ala Asp Glu Val Leu Phe Leu Gln Gly Ser Lys Ala
            260                 265                 270

Tyr Leu Gln Asn Lys Gly Phe Asp Val Asp Lys Asp Gly Lys Ile Thr
        275                 280                 285

Leu Gly Glu Ile Ser Ser Thr Leu Tyr Thr Thr Tyr Tyr Lys Gly Leu
    290                 295                 300

Leu Pro Glu Asn Arg His Val Ile Ser Tyr
305                 310

<210> SEQ ID NO 41
<211> LENGTH: 325
<212> TYPE: PRT
<213> ORGANISM: unknown
<220> FEATURE:
<223> OTHER INFORMATION: (POLY)3-gp188

<400> SEQUENCE: 41

Met Gly Ser Lys Arg Lys Lys Arg Lys Lys Arg Lys Ser Lys Arg
1               5                   10                  15

Lys Lys Arg Lys Lys Arg Lys Arg Ser Lys Arg Lys Lys Arg Lys Lys
            20                  25                  30
```

```
Arg Lys Asn Phe Arg Thr Lys Asn Gly Tyr Arg Asp Leu Gln Ala Leu
             35                  40                  45
Val Lys Glu Leu Gly Leu Tyr Thr Gly Gln Ile Asp Gly Val Trp Gly
 50                  55                  60
Lys Gly Thr Ser Ser Thr Glu Thr Leu Leu Arg Gly Tyr Ala Glu
 65                  70                  75                  80
Val Val Gly Lys Asn Thr Gly Gly Ile Gly Leu Pro Thr Thr Ser Asp
                 85                  90                  95
Ala Ser Gly Tyr Asn Val Ile Thr Ala Leu Gln Arg Asn Leu Ala Phe
                100                 105                 110
Leu Gly Leu Tyr Ser Leu Thr Val Asp Gly Ile Trp Gly Asn Gly Thr
            115                 120                 125
Leu Ser Gly Leu Asp Lys Ala Phe Glu Val Tyr Lys Glu Arg Tyr Arg
130                 135                 140
Thr Pro Thr Tyr Asp Ile Ala Trp Ser Gly Lys Val Ser Pro Ala Phe
145                 150                 155                 160
Thr Ala Lys Val Lys Asp Trp Cys Gly Val His Val Pro Asn His Arg
                165                 170                 175
Ala Pro His Trp Leu Met Ala Cys Met Ala Phe Glu Thr Gly Gln Thr
            180                 185                 190
Phe Ser Pro Ser Ile Lys Asn Ala Ala Gly Ser Glu Ala Tyr Gly Leu
        195                 200                 205
Ile Gln Phe Met Ser Pro Ala Ala Asn Asp Leu Asn Val Pro Leu Ser
    210                 215                 220
Val Ile Arg Ser Met Asp Gln Leu Thr Gln Leu Asp Leu Val Phe Lys
225                 230                 235                 240
Tyr Phe Glu Met Trp Met Lys Arg Gly Lys Arg Tyr Thr Gln Leu Glu
                245                 250                 255
Asp Phe Tyr Leu Thr Ile Phe His Pro Ala Ser Val Gly Lys Lys Ala
            260                 265                 270
Asp Glu Val Leu Phe Leu Gln Gly Ser Lys Ala Tyr Leu Gln Asn Lys
        275                 280                 285
Gly Phe Asp Val Asp Lys Asp Gly Lys Ile Thr Leu Gly Glu Ile Ser
    290                 295                 300
Ser Thr Leu Tyr Thr Thr Tyr Tyr Lys Gly Leu Leu Pro Glu Asn Arg
305                 310                 315                 320
His Val Ile Ser Tyr
            325

<210> SEQ ID NO 42
<211> LENGTH: 336
<212> TYPE: PRT
<213> ORGANISM: unknown
<220> FEATURE:
<223> OTHER INFORMATION: (POLY)4-gp188

<400> SEQUENCE: 42

Met Gly Ser Lys Arg Lys Lys Arg Lys Lys Arg Lys Arg Ser Lys Arg
  1               5                  10                  15
Lys Lys Arg Lys Lys Arg Lys Arg Ser Lys Arg Lys Lys Arg Lys Lys
                 20                  25                  30
Arg Lys Arg Ser Lys Arg Lys Arg Lys Lys Arg Lys Asn Phe Arg
             35                  40                  45
Thr Lys Asn Gly Tyr Arg Asp Leu Gln Ala Leu Val Lys Glu Leu Gly
 50                  55                  60
```

Leu Tyr Thr Gly Gln Ile Asp Gly Val Trp Gly Lys Gly Thr Ser Ser
65                  70                  75                  80

Ser Thr Glu Thr Leu Leu Arg Gly Tyr Ala Glu Val Val Gly Lys Asn
                85                  90                  95

Thr Gly Gly Ile Gly Leu Pro Thr Thr Ser Asp Ala Ser Gly Tyr Asn
            100                 105                 110

Val Ile Thr Ala Leu Gln Arg Asn Leu Ala Phe Leu Gly Leu Tyr Ser
        115                 120                 125

Leu Thr Val Asp Gly Ile Trp Gly Asn Gly Thr Leu Ser Gly Leu Asp
    130                 135                 140

Lys Ala Phe Glu Val Tyr Lys Glu Arg Tyr Arg Thr Pro Thr Tyr Asp
145                 150                 155                 160

Ile Ala Trp Ser Gly Lys Val Ser Pro Ala Phe Thr Ala Lys Val Lys
                165                 170                 175

Asp Trp Cys Gly Val His Val Pro Asn His Arg Ala Pro His Trp Leu
            180                 185                 190

Met Ala Cys Met Ala Phe Glu Thr Gly Gln Thr Phe Ser Pro Ser Ile
        195                 200                 205

Lys Asn Ala Ala Gly Ser Glu Ala Tyr Gly Leu Ile Gln Phe Met Ser
    210                 215                 220

Pro Ala Ala Asn Asp Leu Asn Val Pro Leu Ser Val Ile Arg Ser Met
225                 230                 235                 240

Asp Gln Leu Thr Gln Leu Asp Leu Val Phe Lys Tyr Phe Glu Met Trp
                245                 250                 255

Met Lys Arg Gly Lys Arg Tyr Thr Gln Leu Glu Asp Phe Tyr Leu Thr
            260                 265                 270

Ile Phe His Pro Ala Ser Val Gly Lys Lys Ala Asp Glu Val Leu Phe
        275                 280                 285

Leu Gln Gly Ser Lys Ala Tyr Leu Gln Asn Lys Gly Phe Asp Val Asp
    290                 295                 300

Lys Asp Gly Lys Ile Thr Leu Gly Glu Ile Ser Ser Thr Leu Tyr Thr
305                 310                 315                 320

Thr Tyr Tyr Lys Gly Leu Leu Pro Glu Asn Arg His Val Ile Ser Tyr
                325                 330                 335

<210> SEQ ID NO 43
<211> LENGTH: 272
<212> TYPE: PRT
<213> ORGANISM: unknown
<220> FEATURE:
<223> OTHER INFORMATION: pKKZ144pET32b

<400> SEQUENCE: 43

Ala Met Gly Ser Lys Arg Lys Arg Lys Arg Lys Lys Val Leu
1               5                   10                  15

Arg Lys Gly Asp Arg Gly Asp Glu Val Cys Gln Leu Gln Thr Leu Leu
            20                  25                  30

Asn Leu Cys Gly Tyr Asp Val Gly Lys Pro Asp Gly Ile Phe Gly Asn
        35                  40                  45

Asn Thr Phe Asn Gln Val Val Lys Phe Gln Lys Asp Asn Cys Leu Asp
    50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

```
Lys Ser Arg Ala Ala Thr Pro Val Met Asn Ala Val Glu Asn Ala
                100                 105                 110

Thr Gly Val Arg Ser Gln Leu Leu Thr Phe Ala Ser Ile Glu Ser
            115                 120                 125

Ala Phe Asp Tyr Glu Ile Lys Ala Lys Thr Ser Ser Ala Thr Gly Trp
130                 135                 140

Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Lys Arg Glu Pro Thr Asp Thr Asp Leu
                195                 200                 205

Tyr Leu Ala His Phe Phe Gly Pro Gly Ala Ala Arg Arg Phe Leu Thr
            210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
                245                 250                 255

Gln Glu Val Tyr Asn Leu Met Asp Gly Lys Val Ala Ala His Arg Lys
            260                 265                 270

<210> SEQ ID NO 44
<211> LENGTH: 269
<212> TYPE: PRT
<213> ORGANISM: unknown
<220> FEATURE:
<223> OTHER INFORMATION: KRK_6_pET32b

<400> SEQUENCE: 44

Ala Met Gly Ser Lys Arg Lys Arg Lys Lys Val Leu Arg Lys Gly
1               5                   10                  15

Asp Arg Gly Asp Glu Val Cys Gln Leu Gln Thr Leu Leu Asn Leu Cys
                20                  25                  30

Gly Tyr Asp Val Gly Lys Pro Asp Gly Ile Phe Gly Asn Asn Thr Phe
            35                  40                  45

Asn Gln Val Val Lys Phe Gln Lys Asp Asn Cys Leu Asp Ser Asp Gly
50                  55                  60

Ile Val Gly Lys Asn Thr Trp Ala Glu Leu Phe Ser Lys Tyr Ser Pro
65                  70                  75                  80

Pro Ile Pro Tyr Lys Thr Ile Pro Met Pro Thr Ala Asn Lys Ser Arg
                85                  90                  95

Ala Ala Ala Thr Pro Val Met Asn Ala Val Glu Asn Ala Thr Gly Val
            100                 105                 110

Arg Ser Gln Leu Leu Thr Phe Ala Ser Ile Glu Ser Ala Phe Asp
        115                 120                 125

Tyr Glu Ile Lys Ala Lys Thr Ser Ser Ala Thr Gly Trp Phe Gln Phe
130                 135                 140

Leu Thr Gly Thr Trp Lys Thr Met Ile Glu Asn Tyr Gly Met Lys Tyr
145                 150                 155                 160

Gly Val Leu Thr Asp Pro Thr Gly Ala Leu Arg Lys Asp Pro Arg Ile
                165                 170                 175

Ser Ala Leu Met Gly Ala Glu Leu Ile Lys Glu Asn Met Asn Ile Leu
            180                 185                 190
```

Arg Pro Val Leu Lys Arg Glu Pro Thr Asp Thr Asp Leu Tyr Leu Ala
        195                 200                 205

His Phe Phe Gly Pro Gly Ala Arg Arg Phe Leu Thr Thr Gly Gln
    210                 215                 220

Asn Glu Leu Ala Ala Thr His Phe Pro Lys Glu Ala Gln Ala Asn Pro
225                 230                 235                 240

Ser Ile Phe Tyr Asn Lys Asp Gly Ser Pro Lys Thr Ile Gln Glu Val
                245                 250                 255

Tyr Asn Leu Met Asp Gly Lys Val Ala Ala His Arg Lys
            260                 265

<210> SEQ ID NO 45
<211> LENGTH: 275
<212> TYPE: PRT
<213> ORGANISM: unknown
<220> FEATURE:
<223> OTHER INFORMATION: KRK_12_pET32b

<400> SEQUENCE: 45

Ala Met Gly Ser Lys Arg Lys Arg Lys Arg Lys Arg Lys
1               5                   10                  15

Lys Val Leu Arg Lys Gly Asp Arg Gly Asp Glu Val Cys Gln Leu Gln
            20                  25                  30

Thr Leu Leu Asn Leu Cys Gly Tyr Asp Val Gly Lys Pro Asp Gly Ile
            35                  40                  45

Phe Gly Asn Asn Thr Phe Asn Gln Val Val Lys Phe Gln Lys Asp Asn
        50                  55                  60

Cys Leu Asp Ser Asp Gly Ile Val Gly Lys Asn Thr Trp Ala Glu Leu
65                  70                  75                  80

Phe Ser Lys Tyr Ser Pro Pro Ile Pro Tyr Lys Thr Ile Pro Met Pro
                85                  90                  95

Thr Ala Asn Lys Ser Arg Ala Ala Ala Thr Pro Val Met Asn Ala Val
            100                 105                 110

Glu Asn Ala Thr Gly Val Arg Ser Gln Leu Leu Thr Phe Ala Ser
            115                 120                 125

Ile Glu Ser Ala Phe Asp Tyr Glu Ile Lys Ala Lys Thr Ser Ser Ala
        130                 135                 140

Thr Gly Trp Phe Gln Phe Leu Thr Gly Thr Trp Lys Thr Met Ile Glu
145                 150                 155                 160

Asn Tyr Gly Met Lys Tyr Gly Val Leu Thr Asp Pro Thr Gly Ala Leu
                165                 170                 175

Arg Lys Asp Pro Arg Ile Ser Ala Leu Met Gly Ala Glu Leu Ile Lys
            180                 185                 190

Glu Asn Met Asn Ile Leu Arg Pro Val Leu Lys Arg Glu Pro Thr Asp
        195                 200                 205

Thr Asp Leu Tyr Leu Ala His Phe Phe Gly Pro Gly Ala Ala Arg Arg
210                 215                 220

Phe Leu Thr Thr Gly Gln Asn Glu Leu Ala Ala Thr His Phe Pro Lys
225                 230                 235                 240

Glu Ala Gln Ala Asn Pro Ser Ile Phe Tyr Asn Lys Asp Gly Ser Pro
                245                 250                 255

Lys Thr Ile Gln Glu Val Tyr Asn Leu Met Asp Gly Lys Val Ala Ala
            260                 265                 270

His Arg Lys
        275

```
<210> SEQ ID NO 46
<211> LENGTH: 277
<212> TYPE: PRT
<213> ORGANISM: unknown
<220> FEATURE:
<223> OTHER INFORMATION: KRK_14_pET32b

<400> SEQUENCE: 46

Ala Met Gly Ser Lys Arg Lys Arg Lys Lys Arg Lys Lys Arg Lys
1               5                   10                  15

Lys Arg Lys Val Leu Arg Lys Gly Asp Arg Gly Asp Glu Val Cys Gln
            20                  25                  30

Leu Gln Thr Leu Leu Asn Leu Cys Gly Tyr Asp Val Gly Lys Pro Asp
            35                  40                  45

Gly Ile Phe Gly Asn Asn Thr Phe Asn Gln Val Val Lys Phe Gln Lys
        50                  55                  60

Asp Asn Cys Leu Asp Ser Asp Gly Ile Val Gly Lys Asn Thr Trp Ala
65                  70                  75                  80

Glu Leu Phe Ser Lys Tyr Ser Pro Pro Ile Pro Tyr Lys Thr Ile Pro
                85                  90                  95

Met Pro Thr Ala Asn Lys Ser Arg Ala Ala Thr Pro Val Met Asn
            100                 105                 110

Ala Val Glu Asn Ala Thr Gly Val Arg Ser Gln Leu Leu Leu Thr Phe
            115                 120                 125

Ala Ser Ile Glu Ser Ala Phe Asp Tyr Glu Ile Lys Ala Lys Thr Ser
        130                 135                 140

Ser Ala Thr Gly Trp Phe Gln Phe Leu Thr Gly Thr Trp Lys Thr Met
145                 150                 155                 160

Ile Glu Asn Tyr Gly Met Lys Tyr Gly Val Leu Thr Asp Pro Thr Gly
                165                 170                 175

Ala Leu Arg Lys Asp Pro Arg Ile Ser Ala Leu Met Gly Ala Glu Leu
            180                 185                 190

Ile Lys Glu Asn Met Asn Ile Leu Arg Pro Val Leu Lys Arg Glu Pro
        195                 200                 205

Thr Asp Thr Asp Leu Tyr Leu Ala His Phe Phe Gly Pro Gly Ala Ala
    210                 215                 220

Arg Arg Phe Leu Thr Thr Gly Gln Asn Glu Leu Ala Ala Thr His Phe
225                 230                 235                 240

Pro Lys Glu Ala Gln Ala Asn Pro Ser Ile Phe Tyr Asn Lys Asp Gly
                245                 250                 255

Ser Pro Lys Thr Ile Gln Glu Val Tyr Asn Leu Met Asp Gly Lys Val
            260                 265                 270

Ala Ala His Arg Lys
        275

<210> SEQ ID NO 47
<211> LENGTH: 272
<212> TYPE: PRT
<213> ORGANISM: unknown
<220> FEATURE:
<223> OTHER INFORMATION: R9_pET32b

<400> SEQUENCE: 47

Ala Met Gly Ser Arg Arg Arg Arg Arg Arg Arg Arg Arg Lys Val Leu
1               5                   10                  15

Arg Lys Gly Asp Arg Gly Asp Glu Val Cys Gln Leu Gln Thr Leu Leu
            20                  25                  30
```

-continued

Asn Leu Cys Gly Tyr Asp Val Gly Lys Pro Asp Gly Ile Phe Gly Asn
            35                  40                  45

Asn Thr Phe Asn Gln Val Val Lys Phe Gln Lys Asp Asn Cys Leu Asp
        50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

Lys Ser Arg Ala Ala Ala Thr Pro Val Met Asn Ala Val Glu Asn Ala
            100                 105                 110

Thr Gly Val Arg Ser Gln Leu Leu Leu Thr Phe Ala Ser Ile Glu Ser
        115                 120                 125

Ala Phe Asp Tyr Glu Ile Lys Ala Lys Thr Ser Ser Ala Thr Gly Trp
    130                 135                 140

Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Lys Arg Glu Pro Thr Asp Thr Asp Leu
        195                 200                 205

Tyr Leu Ala His Phe Phe Gly Pro Gly Ala Ala Arg Arg Phe Leu Thr
    210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
                245                 250                 255

Gln Glu Val Tyr Asn Leu Met Asp Gly Lys Val Ala Ala His Arg Lys
            260                 265                 270

<210> SEQ ID NO 48
<211> LENGTH: 271
<212> TYPE: PRT
<213> ORGANISM: unknown
<220> FEATURE:
<223> OTHER INFORMATION: K8_pET32b

<400> SEQUENCE: 48

Ala Met Gly Ser Lys Lys Lys Lys Lys Lys Lys Val Leu Arg
1               5                   10                  15

Lys Gly Asp Arg Gly Asp Glu Val Cys Gln Leu Gln Thr Leu Leu Asn
            20                  25                  30

Leu Cys Gly Tyr Asp Val Gly Lys Pro Asp Gly Ile Phe Gly Asn Asn
        35                  40                  45

Thr Phe Asn Gln Val Val Lys Phe Gln Lys Asp Asn Cys Leu Asp Ser
    50                  55                  60

Asp Gly Ile Val Gly Lys Asn Thr Trp Ala Glu Leu Phe Ser Lys Tyr
65                  70                  75                  80

Ser Pro Pro Ile Pro Tyr Lys Thr Ile Pro Met Pro Thr Ala Asn Lys
                85                  90                  95

Ser Arg Ala Ala Ala Thr Pro Val Met Asn Ala Val Glu Asn Ala Thr
            100                 105                 110

Gly Val Arg Ser Gln Leu Leu Leu Thr Phe Ala Ser Ile Glu Ser Ala
        115                 120                 125

```
Phe Asp Tyr Glu Ile Lys Ala Lys Thr Ser Ser Ala Thr Gly Trp Phe
        130                 135                 140
Gln Phe Leu Thr Gly Thr Trp Lys Thr Met Ile Glu Asn Tyr Gly Met
145                 150                 155                 160
Lys Tyr Gly Val Leu Thr Asp Pro Thr Gly Ala Leu Arg Lys Asp Pro
                165                 170                 175
Arg Ile Ser Ala Leu Met Gly Ala Glu Leu Ile Lys Glu Asn Met Asn
            180                 185                 190
Ile Leu Arg Pro Val Leu Lys Arg Glu Pro Thr Asp Thr Asp Leu Tyr
        195                 200                 205
Leu Ala His Phe Phe Gly Pro Gly Ala Ala Arg Arg Phe Leu Thr Thr
    210                 215                 220
Gly Gln Asn Glu Leu Ala Ala Thr His Phe Pro Lys Glu Ala Gln Ala
225                 230                 235                 240
Asn Pro Ser Ile Phe Tyr Asn Lys Asp Gly Ser Pro Lys Thr Ile Gln
                245                 250                 255
Glu Val Tyr Asn Leu Met Asp Gly Lys Val Ala Ala His Arg Lys
            260                 265                 270

<210> SEQ ID NO 49
<211> LENGTH: 302
<212> TYPE: PRT
<213> ORGANISM: unknown
<220> FEATURE:
<223> OTHER INFORMATION: pK2KZ144_pET32b_mod3

<400> SEQUENCE: 49

Ala Met Gly Ser Lys Arg Lys Arg Lys Lys Arg Lys Arg Gly Ser
1               5                   10                  15
Gly Ser Gly Lys Arg Lys Lys Arg Lys Lys Arg Lys Arg Gly Ser Gly
            20                  25                  30
Ser Gly Lys Arg Lys Lys Arg Lys Lys Arg Lys Lys Val Leu Arg Lys
        35                  40                  45
Gly Asp Arg Gly Asp Glu Val Cys Gln Leu Gln Thr Leu Leu Asn Leu
    50                  55                  60
Cys Gly Tyr Asp Val Gly Lys Pro Asp Gly Ile Phe Gly Asn Asn Thr
65                  70                  75                  80
Phe Asn Gln Val Val Lys Phe Gln Lys Asp Asn Cys Leu Asp Ser Asp
                85                  90                  95
Gly Ile Val Gly Lys Asn Thr Trp Ala Glu Leu Phe Ser Lys Tyr Ser
            100                 105                 110
Pro Pro Ile Pro Tyr Lys Thr Ile Pro Met Pro Thr Ala Asn Lys Ser
        115                 120                 125
Arg Ala Ala Ala Thr Pro Val Met Asn Ala Val Glu Asn Ala Thr Gly
    130                 135                 140
Val Arg Ser Gln Leu Leu Leu Thr Phe Ala Ser Ile Glu Ser Ala Phe
145                 150                 155                 160
Asp Tyr Glu Ile Lys Ala Lys Thr Ser Ser Ala Thr Gly Trp Phe Gln
                165                 170                 175
Phe Leu Thr Gly Thr Trp Lys Thr Met Ile Glu Asn Tyr Gly Met Lys
            180                 185                 190
Tyr Gly Val Leu Thr Asp Pro Thr Gly Ala Leu Arg Lys Asp Pro Arg
        195                 200                 205
Ile Ser Ala Leu Met Gly Ala Glu Leu Ile Lys Glu Asn Met Asn Ile
    210                 215                 220
```

Leu Arg Pro Val Leu Lys Arg Glu Pro Thr Asp Thr Asp Leu Tyr Leu
225                 230                 235                 240

Ala His Phe Phe Gly Pro Gly Ala Ala Arg Arg Phe Leu Thr Thr Gly
            245                 250                 255

Gln Asn Glu Leu Ala Ala Thr His Phe Pro Lys Glu Ala Gln Ala Asn
        260                 265                 270

Pro Ser Ile Phe Tyr Asn Lys Asp Gly Ser Pro Lys Thr Ile Gln Glu
    275                 280                 285

Val Tyr Asn Leu Met Asp Gly Lys Val Ala Ala His Arg Lys
290                 295                 300

<210> SEQ ID NO 50
<211> LENGTH: 30
<212> TYPE: DNA
<213> ORGANISM: artificial sequence
<220> FEATURE:
<223> OTHER INFORMATION: primer PSP3gp10 forw r

<400> SEQUENCE: 50
atgggatccc cggtcattaa tactcaccag                                      30

<210> SEQ ID NO 51
<211> LENGTH: 22
<212> TYPE: DNA
<213> ORGANISM: artificial sequence
<220> FEATURE:
<223> OTHER INFORMATION: primer PSP3gp10 rev

<400> SEQUENCE: 51
tgccatcacc ccgccagccg tg                                              22

<210> SEQ ID NO 52
<211> LENGTH: 57
<212> TYPE: DNA
<213> ORGANISM: artificial sequence
<220> FEATURE:
<223> OTHER INFORMATION: primer PKPSP3gp10 forw

<400> SEQUENCE: 52
atgggatcca aacgcaagaa acgtaagaaa cgcaaaccgg tcattaatac tcaccag        57

<210> SEQ ID NO 53
<211> LENGTH: 176
<212> TYPE: PRT
<213> ORGANISM: unknown
<220> FEATURE:
<223> OTHER INFORMATION: PKPSP3gp10

<400> SEQUENCE: 53

Met Gly Ser Lys Arg Lys Lys Arg Lys Lys Arg Lys Pro Val Ile Asn
1               5                   10                  15

Thr His Gln Asn Ile Ala Ala Phe Leu Asp Met Leu Ala Tyr Ser Glu
            20                  25                  30

Gly Thr Ala Asn His Pro Leu Thr Lys Asn Arg Gly Tyr Asp Val Ile
        35                  40                  45

Val Thr Gly Phe Asp Gly Ser Pro Glu Ile Phe Thr Tyr Ser Asp
    50                  55                  60

His Pro Phe Ala His Gly Arg Pro Lys Val Phe Asn Arg Gly
65                  70                  75                  80

Glu Lys Ser Thr Ala Ser Gly Arg Tyr Gln Gln Leu Tyr Ile Phe Trp
            85                  90                  95

```
Pro His Tyr Lys Lys Gln Leu Ala Leu Pro Asp Phe Ser Pro Leu Ser
            100                 105                 110

Gln Asp Lys Leu Ala Ile Gln Leu Ile Arg Glu Arg Gly Ala Ile Asp
        115                 120                 125

Asp Ile Arg Ala Gly Arg Ile Glu Arg Ala Val Ser Arg Cys Arg Asn
    130                 135                 140

Ile Trp Ala Ser Leu Pro Gly Ala Gly Tyr Gly Gln Arg Glu His Ser
145                 150                 155                 160

Leu Glu Lys Leu Val Thr Val Trp Arg Thr Ala Gly Val Met Ala
                165                 170                 175

<210> SEQ ID NO 54
<211> LENGTH: 28
<212> TYPE: DNA
<213> ORGANISM: artificial sequence
<220> FEATURE:
<223> OTHER INFORMATION: primer SP2gp09 forw

<400> SEQUENCE: 54
atgggatccc cggtaattaa cacgcatc                                        28

<210> SEQ ID NO 55
<211> LENGTH: 25
<212> TYPE: DNA
<213> ORGANISM: artificial sequence
<220> FEATURE:
<223> OTHER INFORMATION: primer P2gp09 rev

<400> SEQUENCE: 55
agccggtacg ccgccagcgg tacgc                                           25

<210> SEQ ID NO 56
<211> LENGTH: 54
<212> TYPE: DNA
<213> ORGANISM: artificial sequence
<220> FEATURE:
<223> OTHER INFORMATION: primer PKP2gp09 forw

<400> SEQUENCE: 56
atgggatcca aacgcaagaa acgtaagaaa cgcaaaccgg taattaacac gcat           54

<210> SEQ ID NO 57
<211> LENGTH: 176
<212> TYPE: PRT
<213> ORGANISM: unknown
<220> FEATURE:
<223> OTHER INFORMATION: PKP2gp09

<400> SEQUENCE: 57

Met Gly Ser Lys Arg Lys Arg Lys Lys Arg Lys Pro Val Ile Asn
1               5                   10                  15

Thr His Gln Asn Ile Ala Ala Phe Leu Asp Met Leu Ala Val Ser Glu
            20                  25                  30

Gly Thr Ala Asn His Pro Leu Thr Lys Asn Arg Gly Tyr Asp Val Ile
        35                  40                  45

Val Thr Gly Leu Asp Gly Lys Pro Glu Ile Phe Thr Asp Tyr Ser Asp
    50                  55                  60

His Pro Phe Ala His Gly Arg Pro Ala Lys Val Phe Asn Arg Arg Gly
65                  70                  75                  80

Glu Lys Ser Thr Ala Ser Gly Arg Tyr Gln Gln Leu Tyr Leu Phe Trp
                85                  90                  95
```

Pro His Tyr Arg Lys Gln Leu Ala Leu Pro Asp Phe Ser Pro Leu Ser
            100                 105                 110

Gln Asp Arg Leu Ala Ile Gln Leu Ile Arg Glu Arg Gly Ala Leu Asp
        115                 120                 125

Asp Ile Arg Ala Gly Arg Ile Glu Arg Ala Ile Ser Arg Cys Arg Asn
130                 135                 140

Ile Trp Ala Ser Leu Pro Gly Ala Gly Tyr Gly Gln Arg Glu His Ser
145                 150                 155                 160

Leu Glu Lys Leu Val Thr Val Trp Arg Thr Ala Gly Val Pro Ala
                165                 170                 175

<210> SEQ ID NO 58
<211> LENGTH: 21
<212> TYPE: DNA
<213> ORGANISM: artificial sequence
<220> FEATURE:
<223> OTHER INFORMATION: primer OBPgpLYS forward

<400> SEQUENCE: 58
atgaaaaata gcgagaagaa t                                                21

<210> SEQ ID NO 59
<211> LENGTH: 24
<212> TYPE: DNA
<213> ORGANISM: artificial sequence
<220> FEATURE:
<223> OTHER INFORMATION: primer OBPgpLYS reverse

<400> SEQUENCE: 59
aactattccg agtgctttct ttgt                                             24

<210> SEQ ID NO 60
<211> LENGTH: 54
<212> TYPE: DNA
<213> ORGANISM: artificial sequence
<220> FEATURE:
<223> OTHER INFORMATION: primer PKOBPgpLYS forward

<400> SEQUENCE: 60
atgggatcca aacgcaagaa acgtaagaaa cgcaaaaaaa atagcgagaa gaat            54

<210> SEQ ID NO 61
<211> LENGTH: 339
<212> TYPE: PRT
<213> ORGANISM: unknown
<220> FEATURE:
<223> OTHER INFORMATION: PKOBPgpLYS

<400> SEQUENCE: 61

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Glu Lys Cys Arg
        35                  40                  45

Gly Ala Ile Ile Leu Met Leu Asn Lys Val Tyr Pro Asn Phe Ser Thr
    50                  55                  60

Asn Lys Leu Pro Ser Asn Thr Tyr Glu Ala Glu Ser Val Phe Thr Phe
65                  70                  75                  80

Leu Gln Thr Ala Leu Ala Gly Val Gly Leu Tyr Thr Ile Thr Ile Asp
            85                  90                  95

```
Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Asp Ile Tyr Trp Val Ser Val Tyr Val Asn Gly Tyr
290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala Leu
                325                 330                 335

Gly Ile Val

<210> SEQ ID NO 62
<211> LENGTH: 283
<212> TYPE: PRT
<213> ORGANISM: unknown
<220> FEATURE:
<223> OTHER INFORMATION: pK2KZ144pET32b

<400> SEQUENCE: 62

Ala Met Gly Ser Lys Arg Lys Lys Arg Lys Arg Lys Arg Ser Lys
1               5                   10                  15

Arg Lys Lys Arg Lys Lys Arg Lys Lys Val Leu Arg Lys Gly Asp Arg
                20                  25                  30

Gly Asp Glu Val Cys Gln Leu Gln Thr Leu Leu Asn Leu Cys Gly Tyr
            35                  40                  45

Asp Val Gly Lys Pro Asp Gly Ile Phe Gly Asn Asn Thr Phe Asn Gln
        50                  55                  60

Val Val Lys Phe Gln Lys Asp Asn Cys Leu Asp Ser Asp Gly Ile Val
65                  70                  75                  80

Gly Lys Asn Thr Trp Ala Glu Leu Phe Ser Lys Tyr Ser Pro Pro Ile
                85                  90                  95

Pro Tyr Lys Thr Ile Pro Met Pro Thr Ala Asn Lys Ser Arg Ala Ala
                100                 105                 110
```

```
Ala Thr Pro Val Met Asn Ala Val Glu Asn Ala Thr Gly Val Arg Ser
            115                 120                 125

Gln Leu Leu Leu Thr Phe Ala Ser Ile Glu Ser Ala Phe Asp Tyr Glu
        130                 135                 140

Ile Lys Ala Lys Thr Ser Ser Ala Thr Gly Trp Phe Gln Phe Leu Thr
145                 150                 155                 160

Gly Thr Trp Lys Thr Met Ile Glu Asn Tyr Gly Met Lys Tyr Gly Val
                165                 170                 175

Leu Thr Asp Pro Thr Gly Ala Leu Arg Lys Asp Pro Arg Ile Ser Ala
            180                 185                 190

Leu Met Gly Ala Glu Leu Ile Lys Glu Asn Met Asn Ile Leu Arg Pro
        195                 200                 205

Val Leu Lys Arg Glu Pro Thr Asp Thr Asp Leu Tyr Leu Ala His Phe
    210                 215                 220

Phe Gly Pro Gly Ala Ala Arg Arg Phe Leu Thr Thr Gly Gln Asn Glu
225                 230                 235                 240

Leu Ala Ala Thr His Phe Pro Lys Glu Ala Gln Ala Asn Pro Ser Ile
                245                 250                 255

Phe Tyr Asn Lys Asp Gly Ser Pro Lys Thr Ile Gln Glu Val Tyr Asn
            260                 265                 270

Leu Met Asp Gly Lys Val Ala Ala His Arg Lys
        275                 280

<210> SEQ ID NO 63
<211> LENGTH: 294
<212> TYPE: PRT
<213> ORGANISM: unknown
<220> FEATURE:
<223> OTHER INFORMATION: pK3KZ144pET32b

<400> SEQUENCE: 63

Ala Met Gly Ser Lys Arg Lys Arg Lys Lys Arg Lys Arg Ser Lys
1               5                   10                  15

Arg Lys Lys Arg Lys Lys Arg Lys Arg Ser Lys Arg Lys Lys Arg Lys
            20                  25                  30

Lys Arg Lys Lys Val Leu Arg Lys Gly Asp Arg Gly Asp Glu Val Cys
        35                  40                  45

Gln Leu Gln Thr Leu Leu Asn Leu Cys Gly Tyr Asp Val Gly Lys Pro
    50                  55                  60

Asp Gly Ile Phe Gly Asn Asn Thr Phe Asn Gln Val Val Lys Phe Gln
65                  70                  75                  80

Lys Asp Asn Cys Leu Asp Ser Asp Gly Ile Val Gly Lys Asn Thr Trp
                85                  90                  95

Ala Glu Leu Phe Ser Lys Tyr Ser Pro Pro Ile Pro Tyr Lys Thr Ile
            100                 105                 110

Pro Met Pro Thr Ala Asn Lys Ser Arg Ala Ala Ala Thr Pro Val Met
        115                 120                 125

Asn Ala Val Glu Asn Ala Thr Gly Val Arg Ser Gln Leu Leu Leu Thr
    130                 135                 140

Phe Ala Ser Ile Glu Ser Ala Phe Asp Tyr Glu Ile Lys Ala Lys Thr
145                 150                 155                 160

Ser Ser Ala Thr Gly Trp Phe Gln Phe Leu Thr Gly Thr Trp Lys Thr
                165                 170                 175

Met Ile Glu Asn Tyr Gly Met Lys Tyr Gly Val Leu Thr Asp Pro Thr
            180                 185                 190
```

Gly Ala Leu Arg Lys Asp Pro Arg Ile Ser Ala Leu Met Gly Ala Glu
            195                 200                 205

Leu Ile Lys Glu Asn Met Asn Ile Leu Arg Pro Val Leu Lys Arg Glu
210                 215                 220

Pro Thr Asp Thr Asp Leu Tyr Leu Ala His Phe Phe Gly Pro Gly Ala
225                 230                 235                 240

Ala Arg Arg Phe Leu Thr Thr Gly Gln Asn Glu Leu Ala Ala Thr His
                245                 250                 255

Phe Pro Lys Glu Ala Gln Ala Asn Pro Ser Ile Phe Tyr Asn Lys Asp
            260                 265                 270

Gly Ser Pro Lys Thr Ile Gln Glu Val Tyr Asn Leu Met Asp Gly Lys
            275                 280                 285

Val Ala Ala His Arg Lys
    290

<210> SEQ ID NO 64
<211> LENGTH: 305
<212> TYPE: PRT
<213> ORGANISM: unknown
<220> FEATURE:
<223> OTHER INFORMATION: pK4KZ144pET32b

<400> SEQUENCE: 64

Ala Met Gly Ser Lys Arg Lys Arg Lys Arg Lys Arg Ser Lys
1               5                   10                  15

Arg Lys Lys Arg Lys Lys Arg Lys Arg Ser Lys Arg Lys Lys Arg Lys
                20                  25                  30

Lys Arg Lys Arg Ser Lys Arg Lys Lys Arg Lys Lys Arg Lys Lys Val
            35                  40                  45

Leu Arg Lys Gly Asp Arg Gly Asp Glu Val Cys Gln Leu Gln Thr Leu
50                  55                  60

Leu Asn Leu Cys Gly Tyr Asp Val Gly Lys Pro Asp Gly Ile Phe Gly
65                  70                  75                  80

Asn Asn Thr Phe Asn Gln Val Val Lys Phe Gln Lys Asp Asn Cys Leu
                85                  90                  95

Asp Ser Asp Gly Ile Val Gly Lys Asn Thr Trp Ala Glu Leu Phe Ser
            100                 105                 110

Lys Tyr Ser Pro Pro Ile Pro Tyr Lys Thr Ile Pro Met Pro Thr Ala
        115                 120                 125

Asn Lys Ser Arg Ala Ala Ala Thr Pro Val Met Asn Ala Val Glu Asn
    130                 135                 140

Ala Thr Gly Val Arg Ser Gln Leu Leu Leu Thr Phe Ala Ser Ile Glu
145                 150                 155                 160

Ser Ala Phe Asp Tyr Glu Ile Lys Ala Lys Thr Ser Ser Ala Thr Gly
                165                 170                 175

Trp Phe Gln Phe Leu Thr Gly Thr Trp Lys Thr Met Ile Glu Asn Tyr
            180                 185                 190

Gly Met Lys Tyr Gly Val Leu Thr Asp Pro Thr Gly Ala Leu Arg Lys
        195                 200                 205

Asp Pro Arg Ile Ser Ala Leu Met Gly Ala Glu Leu Ile Lys Glu Asn
    210                 215                 220

Met Asn Ile Leu Arg Pro Val Leu Lys Arg Glu Pro Thr Asp Thr Asp
225                 230                 235                 240

Leu Tyr Leu Ala His Phe Phe Gly Pro Gly Ala Ala Arg Arg Phe Leu
                245                 250                 255

-continued

```
Thr Thr Gly Gln Asn Glu Leu Ala Ala Thr His Phe Pro Lys Glu Ala
            260                 265                 270

Gln Ala Asn Pro Ser Ile Phe Tyr Asn Lys Asp Gly Ser Pro Lys Thr
        275                 280                 285

Ile Gln Glu Val Tyr Asn Leu Met Asp Gly Lys Val Ala Ala His Arg
    290                 295                 300

Lys
305

<210> SEQ ID NO 65
<211> LENGTH: 18
<212> TYPE: PRT
<213> ORGANISM: artificial sequence
<220> FEATURE:
<223> OTHER INFORMATION: primer gp188 for

<400> SEQUENCE: 65

Ala Thr Gly Ala Ala Cys Thr Thr Cys Cys Gly Gly Ala Cys Gly Ala
1               5                   10                  15

Ala Gly

<210> SEQ ID NO 66
<211> LENGTH: 282
<212> TYPE: PRT
<213> ORGANISM: unknown
<220> FEATURE:
<223> OTHER INFORMATION: KRK_19_pET32b

<400> SEQUENCE: 66

Ala Met Gly Ser Lys Arg Lys Lys Arg Lys Lys Arg Lys Lys Arg Lys
1               5                   10                  15

Lys Arg Lys Lys Arg Lys Lys Lys Val Leu Arg Lys Gly Asp Arg Gly
            20                  25                  30

Asp Glu Val Cys Gln Leu Gln Thr Leu Leu Asn Leu Cys Gly Tyr Asp
        35                  40                  45

Val Gly Lys Pro Asp Gly Ile Phe Gly Asn Asn Thr Phe Asn Gln Val
    50                  55                  60

Val Lys Phe Gln Lys Asp Asn Cys Leu Asp Ser Asp Gly Ile Val Gly
65                  70                  75                  80

Lys Asn Thr Trp Ala Glu Leu Phe Ser Lys Tyr Ser Pro Pro Ile Pro
                85                  90                  95

Tyr Lys Thr Ile Pro Met Pro Thr Ala Asn Lys Ser Arg Ala Ala Ala
            100                 105                 110

Thr Pro Val Met Asn Ala Val Glu Asn Ala Thr Gly Val Arg Ser Gln
        115                 120                 125

Leu Leu Leu Thr Phe Ala Ser Ile Glu Ser Ala Phe Asp Tyr Glu Ile
    130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
        195                 200                 205

Leu Lys Arg Glu Pro Thr Asp Thr Asp Leu Tyr Leu Ala His Phe Phe
    210                 215                 220
```

```
Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
            245                 250                 255

Tyr Asn Lys Asp Gly Ser Pro Lys Thr Ile Gln Glu Val Tyr Asn Leu
        260                 265                 270

Met Asp Gly Lys Val Ala Ala His Arg Lys
        275                 280
```

<210> SEQ ID NO 67
<211> LENGTH: 284
<212> TYPE: PRT
<213> ORGANISM: unknown
<220> FEATURE:
<223> OTHER INFORMATION: KRK_21_pET32b

<400> SEQUENCE: 67

```
Ala Met Gly Ser Lys Arg Lys Lys Arg Lys Lys Arg Lys Lys Arg Lys
1               5                   10                  15

Lys Arg Lys Lys Arg Lys Lys Arg Lys Lys Val Leu Arg Lys Gly Asp
            20                  25                  30

Arg Gly Asp Glu Val Cys Gln Leu Gln Thr Leu Leu Asn Leu Cys Gly
        35                  40                  45

Tyr Asp Val Gly Lys Pro Asp Gly Ile Phe Gly Asn Asn Thr Phe Asn
50                  55                  60

Gln Val Val Lys Phe Gln Lys Asp Asn Cys Leu Asp Ser Asp Gly Ile
65                  70                  75                  80

Val Gly Lys Asn Thr Trp Ala Glu Leu Phe Ser Lys Tyr Ser Pro Pro
                85                  90                  95

Ile Pro Tyr Lys Thr Ile Pro Met Pro Thr Ala Asn Lys Ser Arg Ala
            100                 105                 110

Ala Ala Thr Pro Val Met Asn Ala Val Glu Asn Ala Thr Gly Val Arg
        115                 120                 125

Ser Gln Leu Leu Leu Thr Phe Ala Ser Ile Glu Ser Ala Phe Asp Tyr
130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
        195                 200                 205

Pro Val Leu Lys Arg Glu Pro Thr Asp Thr Asp Leu Tyr Leu Ala His
210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys
        275                 280
```

<210> SEQ ID NO 68
<211> LENGTH: 288

```
<212> TYPE: PRT
<213> ORGANISM: unknown
<220> FEATURE:
<223> OTHER INFORMATION: KRK_25_pET32b

<400> SEQUENCE: 68

Ala Met Gly Ser Lys Arg Lys Arg Lys Arg Lys Arg Lys Arg Lys
1               5                   10                  15

Lys Arg Lys Lys Arg Lys Lys Arg Lys Arg Lys Lys Lys Val Leu
            20                  25                  30

Arg Lys Gly Asp Arg Gly Asp Glu Val Cys Gln Leu Gln Thr Leu Leu
            35                  40                  45

Asn Leu Cys Gly Tyr Asp Val Gly Lys Pro Asp Gly Ile Phe Gly Asn
50                  55                  60

Asn Thr Phe Asn Gln Val Val Lys Phe Gln Lys Asp Asn Cys Leu Asp
65                  70                  75                  80

Ser Asp Gly Ile Val Gly Lys Asn Thr Trp Ala Glu Leu Phe Ser Lys
                85                  90                  95

Tyr Ser Pro Pro Ile Pro Tyr Lys Thr Ile Pro Met Pro Thr Ala Asn
                100                 105                 110

Lys Ser Arg Ala Ala Thr Pro Val Met Asn Ala Val Glu Asn Ala
            115                 120                 125

Thr Gly Val Arg Ser Gln Leu Leu Thr Phe Ala Ser Ile Glu Ser
130                 135                 140

Ala Phe Asp Tyr Glu Ile Lys Ala Lys Thr Ser Ser Ala Thr Gly Trp
145                 150                 155                 160

Phe Gln Phe Leu Thr Gly Thr Trp Lys Thr Met Ile Glu Asn Tyr Gly
                165                 170                 175

Met Lys Tyr Gly Val Leu Thr Asp Pro Thr Gly Ala Leu Arg Lys Asp
            180                 185                 190

Pro Arg Ile Ser Ala Leu Met Gly Ala Glu Leu Ile Lys Glu Asn Met
        195                 200                 205

Asn Ile Leu Arg Pro Val Leu Lys Arg Glu Pro Thr Asp Thr Asp Leu
210                 215                 220

Tyr Leu Ala His Phe Phe Gly Pro Gly Ala Ala Arg Arg Phe Leu Thr
225                 230                 235                 240

Thr Gly Gln Asn Glu Leu Ala Ala Thr His Phe Pro Lys Glu Ala Gln
                245                 250                 255

Ala Asn Pro Ser Ile Phe Tyr Asn Lys Asp Gly Ser Pro Lys Thr Ile
            260                 265                 270

Gln Glu Val Tyr Asn Leu Met Asp Gly Lys Val Ala Ala His Arg Lys
            275                 280                 285

<210> SEQ ID NO 69
<211> LENGTH: 302
<212> TYPE: PRT
<213> ORGANISM: unknown
<220> FEATURE:
<223> OTHER INFORMATION: KRK_39_pET32b

<400> SEQUENCE: 69

Ala Met Gly Ser Lys Arg Lys Arg Lys Arg Lys Arg Lys Arg Lys
1               5                   10                  15

Lys Arg Lys Lys Arg Lys Lys Arg Lys Arg Lys Lys Arg Lys Lys
            20                  25                  30

Arg Lys Lys Arg Lys Lys Arg Lys Lys Arg Lys Lys Val Leu Arg Lys
            35                  40                  45
```

```
Gly Asp Arg Gly Asp Glu Val Cys Gln Leu Gln Thr Leu Leu Asn Leu
    50                  55                  60

Cys Gly Tyr Asp Val Gly Lys Pro Asp Gly Ile Phe Gly Asn Asn Thr
 65                  70                  75                  80

Phe Asn Gln Val Val Lys Phe Gln Lys Asp Asn Cys Leu Asp Ser Asp
                85                  90                  95

Gly Ile Val Gly Lys Asn Thr Trp Ala Glu Leu Phe Ser Lys Tyr Ser
                100                 105                 110

Pro Pro Ile Pro Tyr Lys Thr Ile Pro Met Pro Thr Ala Asn Lys Ser
                115                 120                 125

Arg Ala Ala Thr Pro Val Met Asn Ala Val Glu Asn Ala Thr Gly
130                 135                 140

Val Arg Ser Gln Leu Leu Leu Thr Phe Ala Ser Ile Glu Ser Ala Phe
145                 150                 155                 160

Asp Tyr Glu Ile Lys Ala Lys Thr Ser Ser Ala Thr Gly Trp Phe Gln
                165                 170                 175

Phe Leu Thr Gly Thr Trp Lys Thr Met Ile Glu Asn Tyr Gly Met Lys
                180                 185                 190

Tyr Gly Val Leu Thr Asp Pro Thr Gly Ala Leu Arg Lys Asp Pro Arg
                195                 200                 205

Ile Ser Ala Leu Met Gly Ala Glu Leu Ile Lys Glu Asn Met Asn Ile
210                 215                 220

Leu Arg Pro Val Leu Lys Arg Glu Pro Thr Asp Thr Asp Leu Tyr Leu
225                 230                 235                 240

Ala His Phe Phe Gly Pro Gly Ala Ala Arg Arg Phe Leu Thr Thr Gly
                245                 250                 255

Gln Asn Glu Leu Ala Ala Thr His Phe Pro Lys Glu Ala Gln Ala Asn
                260                 265                 270

Pro Ser Ile Phe Tyr Asn Lys Asp Gly Ser Pro Lys Thr Ile Gln Glu
                275                 280                 285

Val Tyr Asn Leu Met Asp Gly Lys Val Ala Ala His Arg Lys
                290                 295                 300

<210> SEQ ID NO 70
<211> LENGTH: 282
<212> TYPE: PRT
<213> ORGANISM: unknown
<220> FEATURE:
<223> OTHER INFORMATION: K19_pET32b

<400> SEQUENCE: 70

Ala Met Gly Ser Lys Arg Lys Arg Lys Lys Arg Lys Lys Arg Lys
 1               5                  10                  15

Lys Arg Lys Lys Arg Lys Lys Lys Val Leu Arg Lys Gly Asp Arg Gly
                20                  25                  30

Asp Glu Val Cys Gln Leu Gln Thr Leu Leu Asn Leu Cys Gly Tyr Asp
                35                  40                  45

Val Gly Lys Pro Asp Gly Ile Phe Gly Asn Asn Thr Phe Asn Gln Val
 50                  55                  60

Val Lys Phe Gln Lys Asp Asn Cys Leu Asp Ser Asp Gly Ile Val Gly
 65                  70                  75                  80

Lys Asn Thr Trp Ala Glu Leu Phe Ser Lys Tyr Ser Pro Pro Ile Pro
                85                  90                  95

Tyr Lys Thr Ile Pro Met Pro Thr Ala Asn Lys Ser Arg Ala Ala Ala
                100                 105                 110
```

```
Thr Pro Val Met Asn Ala Val Glu Asn Ala Thr Gly Val Arg Ser Gln
            115                 120                 125
Leu Leu Leu Thr Phe Ala Ser Ile Glu Ser Ala Phe Asp Tyr Glu Ile
        130                 135                 140
Lys Ala Lys Thr Ser Ser Ala Thr Gly Trp Phe Gln Phe Leu Thr Gly
145                 150                 155                 160
Thr Trp Lys Thr Met Ile Glu Asn Tyr Gly Met Lys Tyr Gly Val Leu
                165                 170                 175
Thr Asp Pro Thr Gly Ala Leu Arg Lys Asp Pro Arg Ile Ser Ala Leu
            180                 185                 190
Met Gly Ala Glu Leu Ile Lys Glu Asn Met Asn Ile Leu Arg Pro Val
        195                 200                 205
Leu Lys Arg Glu Pro Thr Asp Thr Asp Leu Tyr Leu Ala His Phe Phe
210                 215                 220
Gly Pro Gly Ala Ala Arg Arg Phe Leu Thr Thr Gly Gln Asn Glu Leu
225                 230                 235                 240
Ala Ala Thr His Phe Pro Lys Glu Ala Gln Ala Asn Pro Ser Ile Phe
                245                 250                 255
Tyr Asn Lys Asp Gly Ser Pro Lys Thr Ile Gln Glu Val Tyr Asn Leu
            260                 265                 270
Met Asp Gly Lys Val Ala Ala His Arg Lys
                275                 280

<210> SEQ ID NO 71
<211> LENGTH: 279
<212> TYPE: PRT
<213> ORGANISM: unknown
<220> FEATURE:
<223> OTHER INFORMATION: K16_pET32b

<400> SEQUENCE: 71

Ala Met Gly Ser Lys Lys Lys Lys Lys Lys Lys Lys Lys Lys Lys Lys
1               5                   10                  15
Lys Lys Lys Lys Lys Val Leu Arg Lys Gly Asp Arg Gly Asp Glu Val
                20                  25                  30
Cys Gln Leu Gln Thr Leu Leu Asn Leu Cys Gly Tyr Asp Val Gly Lys
            35                  40                  45
Pro Asp Gly Ile Phe Gly Asn Asn Thr Phe Asn Gln Val Val Lys Phe
        50                  55                  60
Gln Lys Asp Asn Cys Leu Asp Ser Asp Gly Ile Val Gly Lys Asn Thr
65                  70                  75                  80
Trp Ala Glu Leu Phe Ser Lys Tyr Ser Pro Pro Ile Pro Tyr Lys Thr
                85                  90                  95
Ile Pro Met Pro Thr Ala Asn Lys Ser Arg Ala Ala Thr Pro Val
            100                 105                 110
Met Asn Ala Val Glu Asn Ala Thr Gly Val Arg Ser Gln Leu Leu Leu
        115                 120                 125
Thr Phe Ala Ser Ile Glu Ser Ala Phe Asp Tyr Glu Ile Lys Ala Lys
130                 135                 140
Thr Ser Ser Ala Thr Gly Trp Phe Gln Phe Leu Thr Gly Thr Trp Lys
145                 150                 155                 160
Thr Met Ile Glu Asn Tyr Gly Met Lys Tyr Gly Val Leu Thr Asp Pro
                165                 170                 175
Thr Gly Ala Leu Arg Lys Asp Pro Arg Ile Ser Ala Leu Met Gly Ala
            180                 185                 190
```

```
Glu Leu Ile Lys Glu Asn Met Asn Ile Leu Arg Pro Val Leu Lys Arg
        195                 200                 205

Glu Pro Thr Asp Thr Asp Leu Tyr Leu Ala His Phe Phe Gly Pro Gly
    210                 215                 220

Ala Ala Arg Arg Phe Leu Thr Thr Gly Gln Asn Glu Leu Ala Ala Thr
225                 230                 235                 240

His Phe Pro Lys Glu Ala Gln Ala Asn Pro Ser Ile Phe Tyr Asn Lys
                245                 250                 255

Asp Gly Ser Pro Lys Thr Ile Gln Glu Val Tyr Asn Leu Met Asp Gly
                260                 265                 270

Lys Val Ala Ala His Arg Lys
        275

<210> SEQ ID NO 72
<211> LENGTH: 294
<212> TYPE: PRT
<213> ORGANISM: unknown
<220> FEATURE:
<223> OTHER INFORMATION: pKKZ-144_K2_pET32b

<400> SEQUENCE: 72

Ala Met Gly Ser Lys Arg Lys Arg Lys Arg Lys Lys Val Leu
1               5                   10                  15

Arg Lys Gly Asp Arg Gly Asp Glu Val Cys Gln Leu Gln Thr Leu Leu
                20                  25                  30

Asn Leu Cys Gly Tyr Asp Val Gly Lys Pro Asp Gly Ile Phe Gly Asn
            35                  40                  45

Asn Thr Phe Asn Gln Val Val Lys Phe Gln Lys Asp Asn Cys Leu Asp
50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

Lys Ser Arg Ala Ala Ala Thr Pro Val Met Asn Ala Val Glu Asn Ala
            100                 105                 110

Thr Gly Val Arg Ser Gln Leu Leu Leu Thr Phe Ala Ser Ile Glu Ser
        115                 120                 125

Ala Phe Asp Tyr Glu Ile Lys Ala Lys Thr Ser Ser Ala Thr Gly Trp
    130                 135                 140

Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Lys Arg Glu Pro Thr Asp Thr Asp Leu
        195                 200                 205

Tyr Leu Ala His Phe Phe Gly Pro Gly Ala Ala Arg Arg Phe Leu Thr
    210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
                245                 250                 255

Gln Glu Val Tyr Asn Leu Met Asp Gly Lys Val Ala Ala His Arg Lys
            260                 265                 270
```

```
Leu Glu Lys Arg Lys Lys Arg Lys Arg Ser Lys Arg Lys
        275                 280                 285

Lys Arg Lys Lys Arg Lys
        290
```

<210> SEQ ID NO 73
<211> LENGTH: 285
<212> TYPE: PRT
<213> ORGANISM: unknown
<220> FEATURE:
<223> OTHER INFORMATION: pK2KZ144_pET32b_mod1

<400> SEQUENCE: 73

```
Ala Met Gly Ser Lys Arg Lys Lys Arg Lys Lys Arg Lys Arg Gly Ser
1               5                   10                  15

Gly Lys Arg Lys Lys Arg Lys Lys Arg Lys Lys Val Leu Arg Lys Gly
            20                  25                  30

Asp Arg Gly Asp Glu Val Cys Gln Leu Gln Thr Leu Leu Asn Leu Cys
        35                  40                  45

Gly Tyr Asp Val Gly Lys Pro Asp Gly Ile Phe Gly Asn Asn Thr Phe
    50                  55                  60

Asn Gln Val Val Lys Phe Gln Lys Asp Asn Cys Leu Asp Ser Asp Gly
65                  70                  75                  80

Ile Val Gly Lys Asn Thr Trp Ala Glu Leu Phe Ser Lys Tyr Ser Pro
                85                  90                  95

Pro Ile Pro Tyr Lys Thr Ile Pro Met Pro Thr Ala Asn Lys Ser Arg
            100                 105                 110

Ala Ala Ala Thr Pro Val Met Asn Ala Val Glu Asn Ala Thr Gly Val
        115                 120                 125

Arg Ser Gln Leu Leu Thr Phe Ala Ser Ile Glu Ser Ala Phe Asp
    130                 135                 140

Tyr Glu Ile Lys Ala Lys Thr Ser Ser Ala Thr Gly Trp Phe Gln Phe
145                 150                 155                 160

Leu Thr Gly Thr Trp Lys Thr Met Ile Glu Asn Tyr Gly Met Lys Tyr
                165                 170                 175

Gly Val Leu Thr Asp Pro Thr Gly Ala Leu Arg Lys Asp Pro Arg Ile
            180                 185                 190

Ser Ala Leu Met Gly Ala Glu Leu Ile Lys Glu Asn Met Asn Ile Leu
        195                 200                 205

Arg Pro Val Leu Lys Arg Glu Pro Thr Asp Thr Asp Leu Tyr Leu Ala
    210                 215                 220

His Phe Phe Gly Pro Gly Ala Ala Arg Arg Phe Leu Thr Thr Gly Gln
225                 230                 235                 240

Asn Glu Leu Ala Ala Thr His Phe Pro Lys Glu Ala Gln Ala Asn Pro
                245                 250                 255

Ser Ile Phe Tyr Asn Lys Asp Gly Ser Pro Lys Thr Ile Gln Glu Val
            260                 265                 270

Tyr Asn Leu Met Asp Gly Lys Val Ala Ala His Arg Lys
        275                 280                 285
```

<210> SEQ ID NO 74
<211> LENGTH: 287
<212> TYPE: PRT
<213> ORGANISM: unknown
<220> FEATURE:
<223> OTHER INFORMATION: pK2KZ144_pET32b_mod2

```
<400> SEQUENCE: 74

Ala Met Gly Ser Lys Arg Lys Arg Lys Arg Lys Arg Gly Ser
1               5                   10                  15

Gly Ser Gly Lys Arg Lys Arg Lys Arg Lys Lys Val Leu Arg
            20                  25                  30

Lys Gly Asp Arg Gly Asp Glu Val Cys Gln Leu Gln Thr Leu Leu Asn
        35                  40                  45

Leu Cys Gly Tyr Asp Val Gly Lys Pro Asp Gly Ile Phe Gly Asn Asn
    50                  55                  60

Thr Phe Asn Gln Val Val Lys Phe Gln Lys Asp Asn Cys Leu Asp Ser
65                  70                  75                  80

Asp Gly Ile Val Gly Lys Asn Thr Trp Ala Glu Leu Phe Ser Lys Tyr
                85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
        115                 120                 125

Gly Val Arg Ser Gln Leu Leu Leu Thr Phe Ala Ser Ile Glu Ser Ala
130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
        195                 200                 205

Ile Leu Arg Pro Val Leu Lys Arg Glu Pro Thr Asp Thr Asp Leu Tyr
210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala His Arg Lys
        275                 280                 285

<210> SEQ ID NO 75
<211> LENGTH: 292
<212> TYPE: PRT
<213> ORGANISM: unknown
<220> FEATURE:
<223> OTHER INFORMATION: smi01_KRK9

<400> SEQUENCE: 75

Ala Met Gly Ser Lys Arg Lys Arg Lys Arg Lys Glu Tyr Asp
1               5                   10                  15

Met Ile Leu Lys Phe Gly Ser Lys Gly Asp Ala Val Ala Thr Leu Gln
            20                  25                  30

Lys Gln Leu Ala Lys Met Gly Tyr Lys Gly Val Lys Asp Lys Pro Leu
        35                  40                  45

Ser Val Asp Gly His Phe Gly Glu Ser Thr Glu Phe Ala Val Ile Gln
    50                  55                  60

Leu Gln Arg Lys Phe Gly Leu Val Ala Asp Gly Lys Val Gly Asp Lys
```

```
                65                  70                  75                  80
Thr Arg Gln Ala Leu Ala Gly Asp Ser Val Ser Lys Phe Leu Lys Asp
                    85                  90                  95

Glu Asp Tyr Lys Lys Ala Ala Ile Arg Leu Lys Val Pro Glu Leu Val
                100                 105                 110

Ile Arg Val Phe Gly Ala Val Glu Gly Leu Gly Val Gly Phe Leu Pro
                115                 120                 125

Asn Gly Lys Ala Lys Ile Leu Phe Glu Arg His Arg Met Tyr Phe Tyr
            130                 135                 140

Leu Cys Gln Ala Leu Gly Lys Thr Phe Ala Asn Ser Gln Val Lys Ile
145                 150                 155                 160

Thr Pro Asn Ile Val Asn Thr Leu Thr Gly Gly Tyr Lys Gly Asp Ala
                    165                 170                 175

Ala Glu Tyr Thr Arg Leu Ser Met Ala Ile Asn Ile His Lys Glu Ser
                180                 185                 190

Ala Leu Met Ser Thr Ser Trp Gly Gln Phe Gln Ile Met Gly Glu Asn
                195                 200                 205

Trp Lys Asp Leu Gly Tyr Ser Ser Val Gln Glu Phe Val Asp Gln Gln
            210                 215                 220

Gln Leu Asn Glu Gly Asn Gln Leu Glu Ala Phe Ile Arg Phe Ile Glu
225                 230                 235                 240

Trp Lys Pro Gly Leu Leu Glu Ala Leu Arg Lys Gln Asp Trp Asp Thr
                    245                 250                 255

Val Phe Thr Leu Tyr Asn Gly Lys Asn Tyr Lys Lys Leu Gly Tyr Gln
                260                 265                 270

Ala Lys Phe Gln Lys Glu Trp Asp His Leu Glu Pro Ile Tyr Arg Glu
                275                 280                 285

Lys Thr Ala Ala
        290

<210> SEQ ID NO 76
<211> LENGTH: 176
<212> TYPE: PRT
<213> ORGANISM: unknown
<220> FEATURE:
<223> OTHER INFORMATION: smi02_KRK9

<400> SEQUENCE: 76

Ala Met Gly Ser Lys Arg Lys Arg Lys Lys Arg Lys Gly Asn Ile
1               5                   10                  15

Phe Glu Met Leu Arg Ile Asp Glu Gly Leu Arg Leu Lys Ile Tyr Lys
                20                  25                  30

Asp Thr Glu Gly Tyr Tyr Thr Ile Gly Ile Gly His Leu Leu Thr Lys
            35                  40                  45

Ser Pro Ser Leu Asn Ala Ala Lys Ser Glu Leu Asp Lys Ala Ile Gly
    50                  55                  60

Arg Asn Cys Asn Gly Val Ile Thr Lys Asp Glu Ala Glu Lys Leu Phe
65                  70                  75                  80

Asn Gln Asp Val Asp Ala Ala Val Arg Gly Ile Leu Arg Asn Ala Lys
                85                  90                  95

Leu Lys Pro Val Tyr Asp Ser Leu Asp Ala Val Arg Arg Cys Ala Leu
                100                 105                 110

Ile Asn Met Val Phe Gln Met Gly Glu Thr Gly Val Ala Gly Phe Thr
            115                 120                 125

Asn Ser Leu Arg Met Leu Gln Gln Lys Arg Trp Asp Glu Ala Ala Val
```

```
                130                 135                 140
Asn Leu Ala Lys Ser Arg Trp Tyr Asn Gln Thr Pro Asn Arg Ala Lys
145                 150                 155                 160

Arg Val Ile Thr Thr Phe Arg Thr Gly Thr Trp Asp Ala Tyr Lys Asn
                165                 170                 175

<210> SEQ ID NO 77
<211> LENGTH: 164
<212> TYPE: PRT
<213> ORGANISM: unknown
<220> FEATURE:
<223> OTHER INFORMATION: smi03_KRK9

<400> SEQUENCE: 77

Ala Met Gly Ser Lys Arg Lys Arg Lys Lys Arg Lys Val Ser Lys
1               5                   10                  15

Val Gln Phe Asn Pro Arg Ser Arg Thr Asp Ala Ile Phe Val His Cys
                20                  25                  30

Ser Ala Thr Lys Pro Glu Met Asp Ile Gly Val Glu Thr Ile Arg Met
                35                  40                  45

Trp His Lys Gln Gln Ala Trp Leu Asp Val Gly Tyr His Phe Ile Ile
        50                  55                  60

Lys Arg Asp Gly Thr Val Glu Glu Gly Arg Pro Val Asn Val Val Gly
65                  70                  75                  80

Ser His Val Lys Asp Trp Asn Ser Arg Ser Val Gly Val Cys Leu Val
                85                  90                  95

Gly Gly Ile Asn Ala Lys Gly Gln Phe Glu Ala Asn Phe Thr Pro Ala
                100                 105                 110

Gln Met Asn Ser Leu Arg Asn Lys Leu Asp Asp Leu Lys Val Met Tyr
            115                 120                 125

Pro Gln Ala Glu Ile Arg Ala His His Asp Val Ala Pro Lys Ala Cys
            130                 135                 140

Pro Ser Phe Asp Leu Gln Arg Trp Leu Ser Thr Asn Glu Leu Val Thr
145                 150                 155                 160

Ser Asp Arg Gly

<210> SEQ ID NO 78
<211> LENGTH: 194
<212> TYPE: PRT
<213> ORGANISM: unknown
<220> FEATURE:
<223> OTHER INFORMATION: smi04_KRK9

<400> SEQUENCE: 78

Ala Met Gly Ser Lys Arg Lys Arg Lys Lys Arg Lys Gly Lys Pro
1               5                   10                  15

Lys Asp Glu Ile Phe Asp Glu Ile Leu Gly Lys Glu Gly Tyr Val
                20                  25                  30

Asn His Pro Asp Asp Lys Gly Pro Thr Lys Trp Gly Ile Thr Glu
            35                  40                  45

Lys Val Ala Arg Ala His Gly Tyr Arg Gly Asp Met Arg Asn Leu Thr
        50                  55                  60

Arg Gly Gln Ala Leu Glu Ile Leu Glu Thr Asp Tyr Trp Tyr Gly Pro
65                  70                  75                  80

Arg Phe Asp Arg Val Ala Lys Ala Ser Pro Asp Val Ala Ala Glu Leu
                85                  90                  95

Cys Asp Thr Gly Val Asn Met Gly Pro Ser Val Ala Ala Lys Met Leu
```

```
                100             105             110
Gln Arg Trp Leu Asn Val Phe Asn Gln Gly Gly Arg Leu Tyr Pro Asp
        115                 120                 125

Met Asp Thr Asp Gly Arg Ile Gly Pro Arg Thr Leu Asn Ala Leu Arg
    130                 135                 140

Val Tyr Leu Glu Lys Arg Gly Lys Asp Gly Glu Arg Val Leu Leu Val
145                 150                 155                 160

Ala Leu Asn Cys Thr Gln Gly Glu Arg Tyr Leu Glu Leu Ala Glu Lys
                165                 170                 175

Arg Glu Ala Asp Glu Ser Phe Val Tyr Gly Trp Met Lys Glu Arg Val
            180                 185                 190

Leu Ile

<210> SEQ ID NO 79
<211> LENGTH: 52
<212> TYPE: DNA
<213> ORGANISM: artificial sequence
<220> FEATURE:
<223> OTHER INFORMATION: primer PKgp144 for

<400> SEQUENCE: 79
atgggatcca aacgcaagaa acgtaagaaa cgcaaaaaag tattacgcaa ag        52

<210> SEQ ID NO 80
<211> LENGTH: 51
<212> TYPE: DNA
<213> ORGANISM: artificial sequence
<220> FEATURE:
<223> OTHER INFORMATION: primer PKgp188 for

<400> SEQUENCE: 80
atgggatcca aacgcaagaa acgtaagaaa cgcaaaaact tccggacgaa g         51

<210> SEQ ID NO 81
<211> LENGTH: 18
<212> TYPE: DNA
<213> ORGANISM: artificial sequence
<220> FEATURE:
<223> OTHER INFORMATION: primer gp144 rev

<400> SEQUENCE: 81
ttttctatgt gctgcaac                                              18

<210> SEQ ID NO 82
<211> LENGTH: 19
<212> TYPE: DNA
<213> ORGANISM: artificial sequence
<220> FEATURE:
<223> OTHER INFORMATION: primer gp144 rev

<400> SEQUENCE: 82
atacgaaata acgtgacga                                             19

<210> SEQ ID NO 83
<211> LENGTH: 18
<212> TYPE: DNA
<213> ORGANISM: artificial sequence
<220> FEATURE:
<223> OTHER INFORMATION: primer gp144 for

<400> SEQUENCE: 83
atgaaagtat tacgcaaa                                              18
```

<210> SEQ ID NO 84
<211> LENGTH: 339
<212> TYPE: PRT
<213> ORGANISM: unknown
<220> FEATURE:
<223> OTHER INFORMATION: Cpl-1

<400> SEQUENCE: 84

```
Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Cys Leu Ser Ala
            35                  40                  45

Gln Val Glu Gln Ser Asn Pro Ile Gly Phe Tyr His Phe Ala Arg Phe
50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
    210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
        275                 280                 285

Asn Asn Trp Tyr Tyr Met Thr Asn Glu Arg Gly Asn Met Val Ser Asn
    290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala
```

<210> SEQ ID NO 85
<211> LENGTH: 341
<212> TYPE: PRT

<213> ORGANISM: unknown
<220> FEATURE:
<223> OTHER INFORMATION: Ply511

<400> SEQUENCE: 85

```
Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340
```

<210> SEQ ID NO 86
<211> LENGTH: 495
<212> TYPE: PRT
<213> ORGANISM: unknown
<220> FEATURE:
<223> OTHER INFORMATION: LysK

<400> SEQUENCE: 86

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Val Lys Asp Gly
    370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
```

```
                    405                 410                 415
Phe Val Asn Gly Asn Gln Pro Ile Val Thr Arg Ile Gly Ser Pro Phe
                420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
        450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495

<210> SEQ ID NO 87
<211> LENGTH: 245
<212> TYPE: PRT
<213> ORGANISM: unknown
<220> FEATURE:
<223> OTHER INFORMATION: Lysostaphin

<400> SEQUENCE: 87

Met Ala His Glu His Ser Ala Gln Trp Leu Asn Asn Tyr Lys Lys Gly
1               5                   10                  15

Tyr Gly Tyr Gly Pro Tyr Pro Leu Gly Ile Asn Gly Gly Met His Tyr
            20                  25                  30

Gly Val Asp Phe Phe Met Asn Ile Gly Thr Pro Val Lys Ala Ile Ser
        35                  40                  45

Ser Gly Lys Ile Val Glu Ala Gly Trp Ser Asn Tyr Gly Gly Gly Asn
    50                  55                  60

Gln Ile Gly Leu Ile Glu Asn Asp Gly Val His Arg Gln Trp Tyr Met
65                  70                  75                  80

His Leu Ser Lys Tyr Asn Val Lys Val Gly Asp Tyr Val Lys Ala Gly
                85                  90                  95

Gln Ile Ile Gly Trp Ser Gly Ser Thr Gly Tyr Ser Thr Ala Pro His
            100                 105                 110

Leu His Phe Gln Arg Met Val Asn Ser Phe Ser Asn Ser Thr Ala Gln
        115                 120                 125

Asp Pro Met Pro Phe Leu Lys Ser Ala Gly Tyr Gly Lys Ala Gly Gly
    130                 135                 140

Thr Val Thr Pro Thr Pro Asn Thr Gly Trp Lys Thr Asn Lys Tyr Gly
145                 150                 155                 160

Thr Leu Tyr Lys Ser Glu Ser Ala Ser Phe Thr Pro Asn Thr Asp Ile
                165                 170                 175

Ile Thr Arg Thr Thr Gly Pro Phe Arg Ser Met Pro Gln Ser Gly Val
            180                 185                 190

Leu Lys Ala Gly Gln Thr Ile His Tyr Asp Glu Val Met Lys Gln Asp
        195                 200                 205

Gly His Val Trp Val Gly Tyr Thr Gly Asn Ser Gly Gln Arg Ile Tyr
    210                 215                 220

Leu Pro Val Arg Thr Trp Asn Lys Ser Thr Asn Thr Leu Gly Val Leu
225                 230                 235                 240

Trp Gly Thr Ile Lys
                245

<210> SEQ ID NO 88
<211> LENGTH: 286
<212> TYPE: PRT
```

-continued

<213> ORGANISM: unknown
<220> FEATURE:
<223> OTHER INFORMATION: PA6-gp20

<400> SEQUENCE: 88

Met Val Arg Tyr Ile Pro Ala Ala His His Ser Ala Gly Ser Asn Asn
1               5                   10                  15

Pro Val Asn Arg Val Val Ile His Ala Thr Cys Pro Asp Val Gly Phe
            20                  25                  30

Pro Ser Ala Ser Arg Lys Gly Arg Ala Val Ser Thr Ala Asn Tyr Phe
        35                  40                  45

Ala Ser Pro Ser Gly Gly Ser Ala His Tyr Val Cys Asp Ile Gly
    50                  55                  60

Glu Thr Val Gln Cys Leu Ser Glu Ser Thr Ile Gly Trp His Ala Pro
65                  70                  75                  80

Pro Asn Pro His Ser Leu Gly Ile Glu Ile Cys Ala Asp Gly Gly Ser
                85                  90                  95

His Ala Ser Phe Arg Val Pro Gly His Ala Tyr Thr Arg Glu Gln Trp
            100                 105                 110

Leu Asp Pro Gln Val Trp Pro Ala Val Glu Arg Ala Ala Val Leu Cys
        115                 120                 125

Arg Arg Leu Cys Asp Lys Tyr Asn Val Pro Lys Arg Lys Leu Ser Ala
130                 135                 140

Ala Asp Leu Lys Ala Gly Arg Arg Gly Val Cys Gly His Val Asp Val
145                 150                 155                 160

Thr Asp Ala Trp His Gln Ser Asp His Asp Asp Pro Gly Pro Trp Phe
                165                 170                 175

Pro Trp Asp Lys Phe Met Ala Val Val Asn Gly Gly Ser Gly Asp Ser
            180                 185                 190

Gly Glu Leu Thr Val Ala Asp Val Lys Ala Leu His Asp Gln Ile Lys
        195                 200                 205

Gln Leu Ser Ala Gln Leu Thr Gly Ser Val Asn Lys Leu His His Asp
    210                 215                 220

Val Gly Val Val Gln Val Gln Asn Gly Asp Leu Gly Lys Arg Val Asp
225                 230                 235                 240

Ala Leu Ser Trp Val Lys Asn Pro Val Thr Gly Lys Leu Trp Arg Thr
                245                 250                 255

Lys Asp Ala Leu Trp Ser Val Trp Tyr Tyr Val Leu Glu Cys Arg Ser
            260                 265                 270

Arg Leu Asp Arg Leu Glu Ser Ala Val Asn Asp Leu Lys Lys
        275                 280                 285

<210> SEQ ID NO 89
<211> LENGTH: 177
<212> TYPE: PRT
<213> ORGANISM: unknown
<220> FEATURE:
<223> OTHER INFORMATION: STM0016

<400> SEQUENCE: 89

Met Asn Pro Ile Ile Asp Gly Ile Ile Ala Leu Glu Gly Gly Tyr Val
1               5                   10                  15

Phe Asn Pro Lys Asp Lys Gly Gly Ala Thr His Trp Gly Ile Thr Glu
            20                  25                  30

Ala Thr Ala Arg Ala His Gly Tyr Ala Gly Asp Met Arg Asp Leu Thr
        35                  40                  45

His Ala Glu Ala Tyr Ala Ile Leu Glu Glu Asp Tyr Trp Ile Lys Pro
 50                  55                  60

Gly Phe Asp Val Ile Ser Thr Leu Ser Trp Pro Val Ser Phe Glu Leu
 65                  70                  75                  80

Cys Asp Ala Ala Val Asn Ile Gly Ala Tyr His Pro Ser Ala Trp Leu
                 85                  90                  95

Gln Arg Trp Leu Asn Val Phe Asn His Glu Gly Lys Arg Tyr Pro Asp
            100                 105                 110

Ile His Val Asp Gly Asn Ile Gly Pro Arg Thr Leu Ala Ala Leu Glu
            115                 120                 125

His Tyr Leu Ala Trp Arg Gly Gln Glu Gly Glu Ala Val Leu Val Lys
130                 135                 140

Ala Leu Asn Cys Ser Gln Gly Thr Tyr Tyr Leu Asn Val Ala Glu Lys
145                 150                 155                 160

Asn His Asn Asn Glu Gln Phe Ile Tyr Gly Trp Ile Lys Asn Arg Val
                165                 170                 175

Thr

<210> SEQ ID NO 90
<211> LENGTH: 208
<212> TYPE: PRT
<213> ORGANISM: unknown
<220> FEATURE:
<223> OTHER INFORMATION: N4-gp61

<400> SEQUENCE: 90

Met Ala Ile Ser Lys Lys Val Gly Val Gly Val Ile Ala
 1               5                  10                  15

Ala Ile Ala Ala Val Phe Ala Val Glu Gly Gly Tyr Val Asn Asp
                 20                  25                  30

Pro Lys Asp Pro Gly Glu Thr Asn His Gly Val Thr Ile Gln Val
             35                  40                  45

Ala Gln Lys His Lys Gln Glu Leu Glu Ser Met Tyr Asn Trp Asp Gly
 50                  55                  60

Ser Met Lys Asn Leu Thr Gln Glu Met Ala Ser Ser Ile Tyr Tyr Asn
 65                  70                  75                  80

Asp Tyr Ile Leu Lys Pro Gly Phe Val Lys Phe Ala Asp Val Ser Pro
                 85                  90                  95

Ala Val Thr Glu Lys Leu Val Asp Ala Gly Val Asn Thr Gly Pro Ala
            100                 105                 110

Arg Pro Ser Arg Trp Leu Gln Glu Ser Leu Asn Ala Phe Ser Arg Asn
            115                 120                 125

Gly Lys Asp Tyr Pro Lys Ile Gln Val Asp Gly Lys Val Gly Ser Gly
            130                 135                 140

Thr Leu Ser Ala Tyr Lys Ser Leu Gln Asn Lys Arg Gly Lys Val Glu
145                 150                 155                 160

Ala Cys Lys Leu Ile Leu Lys Ser Leu Asp Gly Lys Gln Leu Asn Tyr
                165                 170                 175

Tyr Leu Ser Leu Asn Met Pro Glu Tyr Thr Thr Gly Trp Ile Ala Asn
            180                 185                 190

Arg Ile Gly Asn Val Pro Leu Glu Arg Cys Asn Glu Asp Ile Val Asn
            195                 200                 205

<210> SEQ ID NO 91
<211> LENGTH: 185
<212> TYPE: PRT

-continued

<213> ORGANISM: unknown
<220> FEATURE:
<223> OTHER INFORMATION: N4-gp61 trunc.

<400> SEQUENCE: 91

```
Met Val Glu Gly Gly Tyr Val Asn Asp Pro Lys Asp Pro Gly Glu
1               5                   10                  15

Thr Asn His Gly Val Thr Ile Gln Val Ala Gln Lys His Lys Gln Glu
            20                  25                  30

Leu Glu Ser Met Tyr Asn Trp Asp Gly Ser Met Lys Asn Leu Thr Gln
        35                  40                  45

Glu Met Ala Ser Ser Ile Tyr Tyr Asn Asp Tyr Ile Leu Lys Pro Gly
50                  55                  60

Phe Val Lys Phe Ala Asp Val Ser Pro Ala Val Thr Glu Lys Leu Val
65                  70                  75                  80

Asp Ala Gly Val Asn Thr Gly Pro Ala Arg Pro Ser Arg Trp Leu Gln
                85                  90                  95

Glu Ser Leu Asn Ala Phe Ser Arg Asn Gly Lys Asp Tyr Pro Lys Ile
            100                 105                 110

Gln Val Asp Gly Lys Val Gly Ser Gly Thr Leu Ser Ala Tyr Lys Ser
        115                 120                 125

Leu Gln Asn Lys Arg Gly Lys Val Glu Ala Cys Lys Leu Ile Leu Lys
130                 135                 140

Ser Leu Asp Gly Lys Gln Leu Asn Tyr Tyr Leu Ser Leu Asn Met Pro
145                 150                 155                 160

Glu Tyr Thr Thr Gly Trp Ile Ala Asn Arg Ile Gly Asn Val Pro Leu
                165                 170                 175

Glu Arg Cys Asn Glu Asp Ile Val Asn
            180                 185
```

<210> SEQ ID NO 92
<211> LENGTH: 486
<212> TYPE: PRT
<213> ORGANISM: unknown
<220> FEATURE:
<223> OTHER INFORMATION: Ply2638

<400> SEQUENCE: 92

```
Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
130                 135                 140
```

```
Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
            165                 170                 175

Val Lys Glu Leu Lys His Ile Tyr Ser Asn His Ile Lys Gly Asn Lys
        180                 185                 190

Ile Thr Ala Pro Lys Pro Ser Ile Gln Gly Val Val Ile His Asn Asp
    195                 200                 205

Tyr Gly Ser Met Thr Pro Ser Gln Tyr Leu Pro Trp Leu Tyr Ala Arg
210                 215                 220

Glu Asn Asn Gly Thr His Val Asn Gly Trp Ala Ser Val Tyr Ala Asn
225                 230                 235                 240

Arg Asn Glu Val Leu Trp Tyr His Pro Thr Asp Tyr Val Glu Trp His
                245                 250                 255

Cys Gly Asn Gln Trp Ala Asn Ala Asn Leu Ile Gly Phe Glu Val Cys
            260                 265                 270

Glu Ser Tyr Pro Gly Arg Ile Ser Asp Lys Leu Phe Leu Glu Asn Glu
        275                 280                 285

Glu Ala Thr Leu Lys Val Ala Ala Asp Val Met Lys Ser Tyr Gly Leu
    290                 295                 300

Pro Val Asn Arg Asn Thr Val Arg Leu His Asn Glu Phe Phe Gly Thr
305                 310                 315                 320

Ser Cys Pro His Arg Ser Trp Asp Leu His Val Gly Lys Gly Glu Pro
                325                 330                 335

Tyr Thr Thr Thr Asn Ile Asn Lys Met Lys Asp Tyr Phe Ile Lys Arg
            340                 345                 350

Ile Lys His Tyr Tyr Asp Gly Gly Lys Leu Glu Val Ser Lys Ala Ala
        355                 360                 365

Thr Ile Lys Gln Ser Asp Val Lys Gln Glu Val Lys Lys Gln Glu Ala
    370                 375                 380

Lys Gln Ile Val Lys Ala Thr Asp Trp Lys Gln Asn Lys Asp Gly Ile
385                 390                 395                 400

Trp Tyr Lys Ala Glu His Ala Ser Phe Thr Val Thr Ala Pro Glu Gly
                405                 410                 415

Ile Ile Thr Arg Tyr Lys Gly Pro Trp Thr Gly His Pro Gln Ala Gly
            420                 425                 430

Val Leu Gln Lys Gly Gln Thr Ile Lys Tyr Asp Glu Val Gln Lys Phe
        435                 440                 445

Asp Gly His Val Trp Val Ser Trp Glu Thr Phe Glu Gly Glu Thr Val
    450                 455                 460

Tyr Met Pro Val Arg Thr Trp Asp Ala Lys Thr Gly Lys Val Gly Lys
465                 470                 475                 480

Leu Trp Gly Glu Ile Lys
                485

<210> SEQ ID NO 93
<211> LENGTH: 37
<212> TYPE: PRT
<213> ORGANISM: unknown
<220> FEATURE:
<223> OTHER INFORMATION: LL-37

<400> SEQUENCE: 93

Leu Leu Gly Asp Phe Phe Arg Lys Ser Lys Glu Lys Ile Gly Lys Glu
1               5                   10                  15
```

```
Phe Lys Arg Ile Val Gln Arg Ile Lys Asp Phe Leu Arg Asn Leu Val
            20                  25                  30

Pro Arg Thr Glu Ser
        35

<210> SEQ ID NO 94
<211> LENGTH: 29
<212> TYPE: PRT
<213> ORGANISM: unknown
<220> FEATURE:
<223> OTHER INFORMATION: SMAP-29

<400> SEQUENCE: 94

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 95
<211> LENGTH: 13
<212> TYPE: PRT
<213> ORGANISM: unknown
<220> FEATURE:
<223> OTHER INFORMATION: Indolicidin

<400> SEQUENCE: 95

Ile Leu Pro Trp Lys Trp Pro Trp Trp Pro Trp Arg Arg
1               5                   10

<210> SEQ ID NO 96
<211> LENGTH: 18
<212> TYPE: PRT
<213> ORGANISM: unknown
<220> FEATURE:
<223> OTHER INFORMATION: Protegrin

<400> SEQUENCE: 96

Arg Gly Gly Arg Leu Cys Tyr Cys Arg Arg Arg Phe Cys Val Cys Val
1               5                   10                  15

Gly Arg

<210> SEQ ID NO 97
<211> LENGTH: 31
<212> TYPE: PRT
<213> ORGANISM: unknown
<220> FEATURE:
<223> OTHER INFORMATION: Cecropin P1

<400> SEQUENCE: 97

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 98
<211> LENGTH: 23
<212> TYPE: PRT
<213> ORGANISM: unknown
<220> FEATURE:
<223> OTHER INFORMATION: Magainin

<400> SEQUENCE: 98

Gly Ile Gly Lys Phe Leu His Ser Ala Lys Lys Phe Gly Lys Ala Phe
1               5                   10                  15
```

```
Val Gly Glu Ile Met Asn Ser
            20
```

<210> SEQ ID NO 99
<211> LENGTH: 25
<212> TYPE: PRT
<213> ORGANISM: unknown
<220> FEATURE:
<223> OTHER INFORMATION: Pleurocidin

<400> SEQUENCE: 99

```
Gly Trp Gly Ser Phe Phe Lys Lys Ala Ala His Val Gly Lys His Val
1               5                   10                  15

Gly Lys Ala Ala Leu Thr His Tyr Leu
            20                  25
```

<210> SEQ ID NO 100
<211> LENGTH: 36
<212> TYPE: PRT
<213> ORGANISM: unknown
<220> FEATURE:
<223> OTHER INFORMATION: Cecropin A (A. aegypti)

<400> SEQUENCE: 100

```
Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35
```

<210> SEQ ID NO 101
<211> LENGTH: 40
<212> TYPE: PRT
<213> ORGANISM: unknown
<220> FEATURE:
<223> OTHER INFORMATION: Cecropin A (D. melanogaster)

<400> SEQUENCE: 101

```
Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40
```

<210> SEQ ID NO 102
<211> LENGTH: 21
<212> TYPE: PRT
<213> ORGANISM: unknown
<220> FEATURE:
<223> OTHER INFORMATION: Buforin II

<400> SEQUENCE: 102

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 103
<211> LENGTH: 39
<212> TYPE: PRT
<213> ORGANISM: unknown
<220> FEATURE:

<223> OTHER INFORMATION: Sarcotoxin IA

<400> SEQUENCE: 103

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 104
<211> LENGTH: 17
<212> TYPE: PRT
<213> ORGANISM: unknown
<220> FEATURE:
<223> OTHER INFORMATION: Apidaecin

<400> SEQUENCE: 104

Ala Asn Arg Pro Val Tyr Ile Pro Pro Pro Arg Pro Pro His Pro Arg
1               5                   10                  15

Leu

<210> SEQ ID NO 105
<211> LENGTH: 24
<212> TYPE: PRT
<213> ORGANISM: unknown
<220> FEATURE:
<223> OTHER INFORMATION: Ascaphine 5

<400> SEQUENCE: 105

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 106
<211> LENGTH: 22
<212> TYPE: PRT
<213> ORGANISM: unknown
<220> FEATURE:
<223> OTHER INFORMATION: Nigrocine 2

<400> SEQUENCE: 106

Gly Leu Leu Ser Lys Val Leu Gly Val Gly Lys Lys Val Leu Cys Gly
1               5                   10                  15

Val Ser Gly Leu Val Cys
            20

<210> SEQ ID NO 107
<211> LENGTH: 24
<212> TYPE: PRT
<213> ORGANISM: unknown
<220> FEATURE:
<223> OTHER INFORMATION: Pseudin 1

<400> SEQUENCE: 107

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 108
<211> LENGTH: 18

```
<212> TYPE: PRT
<213> ORGANISM: unknown
<220> FEATURE:
<223> OTHER INFORMATION: Ranalexin

<400> SEQUENCE: 108

Phe Leu Gly Gly Leu Ile Val Pro Ala Met Ile Cys Ala Val Thr Lys
1               5                   10                  15

Lys Cys

<210> SEQ ID NO 109
<211> LENGTH: 26
<212> TYPE: PRT
<213> ORGANISM: unknown
<220> FEATURE:
<223> OTHER INFORMATION: Melittin

<400> SEQUENCE: 109

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 110
<211> LENGTH: 25
<212> TYPE: PRT
<213> ORGANISM: unknown
<220> FEATURE:
<223> OTHER INFORMATION: Lycotoxin 1

<400> SEQUENCE: 110

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 111
<211> LENGTH: 19
<212> TYPE: PRT
<213> ORGANISM: unknown
<220> FEATURE:
<223> OTHER INFORMATION: Parasin 1

<400> SEQUENCE: 111

Lys Gly Arg Gly Lys Gln Gly Gly Lys Val Arg Ala Lys Ala Lys Thr
1               5                   10                  15

Arg Ser Ser

<210> SEQ ID NO 112
<211> LENGTH: 39
<212> TYPE: PRT
<213> ORGANISM: unknown
<220> FEATURE:
<223> OTHER INFORMATION: Buforin I

<400> SEQUENCE: 112

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35
```

```
<210> SEQ ID NO 113
<211> LENGTH: 34
<212> TYPE: PRT
<213> ORGANISM: unknown
<220> FEATURE:
<223> OTHER INFORMATION: Dermaseptin 1

<400> SEQUENCE: 113

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 114
<211> LENGTH: 12
<212> TYPE: PRT
<213> ORGANISM: unknown
<220> FEATURE:
<223> OTHER INFORMATION: Bactenecin 1

<400> SEQUENCE: 114

Arg Leu Cys Arg Ile Val Val Ile Arg Val Cys Arg
1               5                   10

<210> SEQ ID NO 115
<211> LENGTH: 21
<212> TYPE: PRT
<213> ORGANISM: unknown
<220> FEATURE:
<223> OTHER INFORMATION: Thanatin

<400> SEQUENCE: 115

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 116
<211> LENGTH: 19
<212> TYPE: PRT
<213> ORGANISM: unknown
<220> FEATURE:
<223> OTHER INFORMATION: Brevinin 1T

<400> SEQUENCE: 116

Val Asn Pro Ile Ile Leu Gly Val Leu Pro Lys Val Cys Leu Ile Thr
1               5                   10                  15

Lys Lys Cys

<210> SEQ ID NO 117
<211> LENGTH: 26
<212> TYPE: PRT
<213> ORGANISM: unknown
<220> FEATURE:
<223> OTHER INFORMATION: Ranateurin 1

<400> SEQUENCE: 117

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 118
```

```
<211> LENGTH: 46
<212> TYPE: PRT
<213> ORGANISM: unknown
<220> FEATURE:
<223> OTHER INFORMATION: Esculentin 1

<400> SEQUENCE: 118

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys
        35                  40                  45

<210> SEQ ID NO 119
<211> LENGTH: 17
<212> TYPE: PRT
<213> ORGANISM: unknown
<220> FEATURE:
<223> OTHER INFORMATION: Tachyplesin

<400> SEQUENCE: 119

Arg Trp Cys Phe Arg Val Cys Tyr Arg Gly Ile Cys Tyr Arg Lys Cys
1               5                   10                  15

Arg

<210> SEQ ID NO 120
<211> LENGTH: 25
<212> TYPE: PRT
<213> ORGANISM: unknown
<220> FEATURE:
<223> OTHER INFORMATION: Androctonin

<400> SEQUENCE: 120

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 121
<211> LENGTH: 30
<212> TYPE: PRT
<213> ORGANISM: unknown
<220> FEATURE:
<223> OTHER INFORMATION: alpha-defensin

<400> SEQUENCE: 121

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 122
<211> LENGTH: 38
<212> TYPE: PRT
<213> ORGANISM: unknown
<220> FEATURE:
<223> OTHER INFORMATION: beta-defensin

<400> SEQUENCE: 122

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30
```

```
Lys Cys Cys Arg Lys Lys
        35

<210> SEQ ID NO 123
<211> LENGTH: 18
<212> TYPE: PRT
<213> ORGANISM: unknown
<220> FEATURE:
<223> OTHER INFORMATION: theta-defensin

<400> SEQUENCE: 123

Gly Phe Cys Arg Cys Leu Cys Arg Arg Gly Val Cys Arg Cys Ile Cys
1               5                   10                  15

Thr Arg

<210> SEQ ID NO 124
<211> LENGTH: 40
<212> TYPE: PRT
<213> ORGANISM: unknown
<220> FEATURE:
<223> OTHER INFORMATION: defensin (sapecin A)

<400> SEQUENCE: 124

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 125
<211> LENGTH: 46
<212> TYPE: PRT
<213> ORGANISM: unknown
<220> FEATURE:
<223> OTHER INFORMATION: Thionin (crambin)

<400> SEQUENCE: 125

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
        35                  40                  45

<210> SEQ ID NO 126
<211> LENGTH: 50
<212> TYPE: PRT
<213> ORGANISM: unknown
<220> FEATURE:
<223> OTHER INFORMATION: defensin from radish

<400> SEQUENCE: 126

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50
```

```
<210> SEQ ID NO 127
<211> LENGTH: 44
<212> TYPE: PRT
<213> ORGANISM: unknown
<220> FEATURE:
<223> OTHER INFORMATION: Drosomycin

<400> SEQUENCE: 127

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
                20                  25                  30

Cys Ser Pro Ser Leu Lys Cys Trp Cys Glu Gly Cys
            35                  40

<210> SEQ ID NO 128
<211> LENGTH: 25
<212> TYPE: PRT
<213> ORGANISM: unknown
<220> FEATURE:
<223> OTHER INFORMATION: Hepcidin

<400> SEQUENCE: 128

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 129
<211> LENGTH: 44
<212> TYPE: PRT
<213> ORGANISM: unknown
<220> FEATURE:
<223> OTHER INFORMATION: Bac 5

<400> SEQUENCE: 129

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Gly Arg Pro Phe Pro
            35                  40

<210> SEQ ID NO 130
<211> LENGTH: 39
<212> TYPE: PRT
<213> ORGANISM: unknown
<220> FEATURE:
<223> OTHER INFORMATION: PR-39

<400> SEQUENCE: 130

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
            35

<210> SEQ ID NO 131
<211> LENGTH: 20
<212> TYPE: PRT
<213> ORGANISM: unknown
<220> FEATURE:
```

<223> OTHER INFORMATION: Pyrrhocoricin

<400> SEQUENCE: 131

Val Asp Lys Gly Ser Tyr Leu Pro Arg Pro Thr Pro Pro Arg Pro Ile
1               5                   10                  15

Tyr Asn Arg Asn
            20

<210> SEQ ID NO 132
<211> LENGTH: 24
<212> TYPE: PRT
<213> ORGANISM: unknown
<220> FEATURE:
<223> OTHER INFORMATION: Histatin 5

<400> SEQUENCE: 132

Asp Ser His Ala Lys Arg His His Gly Tyr Lys Arg Lys Phe His Glu
1               5                   10                  15

Lys His His Ser His Arg Gly Tyr
            20

<210> SEQ ID NO 133
<211> LENGTH: 34
<212> TYPE: PRT
<213> ORGANISM: unknown
<220> FEATURE:
<223> OTHER INFORMATION: sushi 1

<400> SEQUENCE: 133

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 134
<211> LENGTH: 18
<212> TYPE: PRT
<213> ORGANISM: unknown
<220> FEATURE:
<223> OTHER INFORMATION: Walmagh 1

<400> SEQUENCE: 134

Gly Phe Phe Ile Pro Ala Val Ile Leu Pro Ser Ile Ala Phe Leu Ile
1               5                   10                  15

Val Pro

<210> SEQ ID NO 135
<211> LENGTH: 5
<212> TYPE: PRT
<213> ORGANISM: unknown
<220> FEATURE:
<223> OTHER INFORMATION: Pentapeptide

<400> SEQUENCE: 135

Phe Phe Val Ala Pro
1               5

<210> SEQ ID NO 136
<211> LENGTH: 13
<212> TYPE: PRT
<213> ORGANISM: unknown
<220> FEATURE:
<223> OTHER INFORMATION: alpha4-helix of T4-lysozyme

<400> SEQUENCE: 136

Pro Asn Arg Ala Lys Arg Val Ile Thr Thr Phe Arg Thr
1               5                   10

<210> SEQ ID NO 137
<211> LENGTH: 27
<212> TYPE: PRT
<213> ORGANISM: unknown
<220> FEATURE:
<223> OTHER INFORMATION: WLBU2-Variant

<400> SEQUENCE: 137

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 138
<211> LENGTH: 25
<212> TYPE: PRT
<213> ORGANISM: unknown
<220> FEATURE:
<223> OTHER INFORMATION: Walmagh2

<400> SEQUENCE: 138

Gly Lys Pro Gly Trp Leu Ile Lys Lys Ala Leu Val Phe Lys Lys Leu
1               5                   10                  15

Ile Arg Arg Pro Leu Lys Arg Leu Ala
            20                  25

<210> SEQ ID NO 139
<211> LENGTH: 291
<212> TYPE: PRT
<213> ORGANISM: unknown
<220> FEATURE:
<223> OTHER INFORMATION: SMAP29-KZ144

<400> SEQUENCE: 139

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Cys Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu

```
            165                 170                 175
Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
            195                 200                 205

Glu Asn Met Asn Ile Leu Arg Pro Val Leu Lys Arg Glu Pro Thr Asp
            210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
            245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
            275                 280                 285

His Arg Lys
    290

<210> SEQ ID NO 140
<211> LENGTH: 500
<212> TYPE: PRT
<213> ORGANISM: unknown
<220> FEATURE:
<223> OTHER INFORMATION: Ply2638-PK

<400> SEQUENCE: 140

Ala Met Gly Leu Thr Ala Ile Asp Tyr Leu Thr Lys Lys Gly Trp Lys
1               5                   10                  15

Ile Ser Ser Asp Pro Arg Thr Tyr Asp Gly Tyr Pro Lys Asn Tyr Gly
            20                  25                  30

Tyr Arg Asn Tyr His Glu Asn Gly Ile Asn Tyr Asp Glu Phe Cys Gly
            35                  40                  45

Gly Tyr His Arg Ala Phe Asp Val Tyr Ser Asn Glu Thr Asn Asp Val
    50                  55                  60

Pro Ala Val Thr Ser Gly Thr Val Ile Glu Ala Asn Asp Tyr Gly Asn
65                  70                  75                  80

Phe Gly Gly Thr Phe Val Ile Arg Asp Ala Asn Asp Asn Asp Trp Ile
            85                  90                  95

Tyr Gly His Leu Gln Arg Gly Ser Met Arg Phe Val Val Gly Asp Lys
            100                 105                 110

Val Asn Gln Gly Asp Ile Ile Gly Leu Gln Gly Asn Ser Asn Tyr Tyr
            115                 120                 125

Asp Asn Pro Met Ser Val His Leu His Leu Gln Leu Arg Pro Lys Asp
130                 135                 140

Ala Lys Lys Asp Glu Lys Ser Gln Val Cys Ser Gly Leu Ala Met Glu
145                 150                 155                 160

Lys Tyr Asp Ile Thr Asn Leu Asn Ala Lys Gln Asp Lys Ser Lys Asn
            165                 170                 175

Gly Ser Val Lys Glu Leu Lys His Ile Tyr Ser Asn His Ile Lys Gly
            180                 185                 190

Asn Lys Ile Thr Ala Pro Lys Pro Ser Ile Gln Gly Val Ile His
            195                 200                 205

Asn Asp Tyr Gly Ser Met Thr Pro Ser Gln Tyr Leu Pro Trp Leu Tyr
            210                 215                 220

Ala Arg Glu Asn Asn Gly Thr His Val Asn Gly Trp Ala Ser Val Tyr
```

```
            225                 230                 235                 240
Ala Asn Arg Asn Glu Val Leu Trp Tyr His Pro Thr Asp Tyr Val Glu
                    245                 250                 255

Trp His Cys Gly Asn Gln Trp Ala Asn Ala Asn Leu Ile Gly Phe Glu
                    260                 265                 270

Val Cys Glu Ser Tyr Pro Gly Arg Ile Ser Asp Lys Leu Phe Leu Glu
                    275                 280                 285

Asn Glu Glu Ala Thr Leu Lys Val Ala Ala Asp Val Met Lys Ser Tyr
                290                 295                 300

Gly Leu Pro Val Asn Arg Asn Thr Val Arg Leu His Asn Glu Phe Phe
305                 310                 315                 320

Gly Thr Ser Cys Pro His Arg Ser Trp Asp Leu His Val Gly Lys Gly
                    325                 330                 335

Glu Pro Tyr Thr Thr Thr Asn Ile Asn Lys Met Lys Asp Tyr Phe Ile
                    340                 345                 350

Lys Arg Ile Lys His Tyr Tyr Asp Gly Gly Lys Leu Glu Val Ser Lys
                    355                 360                 365

Ala Ala Thr Ile Lys Gln Ser Asp Val Lys Gln Val Lys Lys Gln
                370                 375                 380

Glu Ala Lys Gln Ile Val Lys Ala Thr Asp Trp Lys Gln Asn Lys Asp
385                 390                 395                 400

Gly Ile Trp Tyr Lys Ala Glu His Ala Ser Phe Thr Val Thr Ala Pro
                    405                 410                 415

Glu Gly Ile Ile Thr Arg Tyr Lys Gly Pro Trp Thr Gly His Pro Gln
                    420                 425                 430

Ala Gly Val Leu Gln Lys Gly Gln Thr Ile Lys Tyr Asp Glu Val Gln
                    435                 440                 445

Lys Phe Asp Gly His Val Trp Val Ser Trp Glu Thr Phe Glu Gly Glu
                    450                 455                 460

Thr Val Tyr Met Pro Val Arg Thr Trp Asp Ala Lys Thr Gly Lys Val
465                 470                 475                 480

Gly Lys Leu Trp Gly Glu Ile Lys Gly Ser Gly Lys Arg Lys Lys Arg
                    485                 490                 495

Lys Lys Arg Lys
                500

<210> SEQ ID NO 141
<211> LENGTH: 348
<212> TYPE: PRT
<213> ORGANISM: unknown
<220> FEATURE:
<223> OTHER INFORMATION: Pentapeptid-Ply 511

<400> SEQUENCE: 141

Met Phe Phe Val Ala Pro Gly Ser Val Lys Tyr Thr Val Glu Asn Lys
1                   5                   10                  15

Ile Ile Ala Gly Leu Pro Lys Gly Lys Leu Lys Gly Ala Asn Phe Val
                    20                  25                  30

Ile Ala His Glu Thr Ala Asn Ser Lys Ser Thr Ile Asp Asn Glu Val
                35                  40                  45

Ser Tyr Met Thr Arg Asn Trp Lys Asn Ala Phe Val Thr His Phe Val
            50                  55                  60

Gly Gly Gly Gly Arg Val Val Gln Val Ala Asn Val Asn Tyr Val Ser
65                  70                  75                  80

Trp Gly Ala Gly Gln Tyr Ala Asn Ser Tyr Ser Tyr Ala Gln Val Glu
```

```
                    85                  90                  95
Leu Cys Arg Thr Ser Asn Ala Thr Thr Phe Lys Lys Asp Tyr Glu Val
                100                 105                 110
Tyr Cys Gln Leu Leu Val Asp Leu Ala Lys Lys Ala Gly Ile Pro Ile
            115                 120                 125
Thr Leu Asp Ser Gly Ser Lys Thr Ser Asp Lys Gly Ile Lys Ser His
        130                 135                 140
Lys Trp Val Ala Asp Lys Leu Gly Gly Thr Thr His Gln Asp Pro Tyr
145                 150                 155                 160
Ala Tyr Leu Ser Ser Trp Gly Ile Ser Lys Ala Gln Phe Ala Ser Asp
                165                 170                 175
Leu Ala Lys Val Ser Gly Gly Asn Thr Gly Thr Ala Pro Ala Lys
                180                 185                 190
Pro Ser Thr Pro Ala Pro Lys Pro Ser Thr Pro Ser Thr Asn Leu Asp
            195                 200                 205
Lys Leu Gly Leu Val Asp Tyr Met Asn Ala Lys Met Asp Ser Ser
        210                 215                 220
Tyr Ser Asn Arg Asp Lys Leu Ala Lys Gln Tyr Gly Ile Ala Asn Tyr
225                 230                 235                 240
Ser Gly Thr Ala Ser Gln Asn Thr Thr Leu Leu Ser Lys Ile Lys Gly
                245                 250                 255
Gly Ala Pro Lys Pro Ser Thr Pro Ala Pro Lys Pro Ser Thr Ser Thr
            260                 265                 270
Ala Lys Lys Ile Tyr Phe Pro Pro Asn Lys Gly Asn Trp Ser Val Tyr
        275                 280                 285
Pro Thr Asn Lys Ala Pro Val Lys Ala Asn Ala Ile Gly Ala Ile Asn
        290                 295                 300
Pro Thr Lys Phe Gly Gly Leu Thr Tyr Thr Ile Gln Lys Asp Arg Gly
305                 310                 315                 320
Asn Gly Val Tyr Glu Ile Gln Thr Asp Gln Phe Gly Arg Val Gln Val
                325                 330                 335
Tyr Gly Ala Pro Ser Thr Gly Ala Val Ile Lys Lys
            340                 345

<210> SEQ ID NO 142
<211> LENGTH: 264
<212> TYPE: PRT
<213> ORGANISM: unknown
<220> FEATURE:
<223> OTHER INFORMATION: PK-Lysostaphin

<400> SEQUENCE: 142

Ala Met Gly Lys Arg Lys Lys Arg Lys Lys Arg Lys Gly Ser Ala His
1               5                   10                  15
Glu His Ser Ala Gln Trp Leu Asn Asn Tyr Lys Lys Gly Tyr Gly Tyr
                20                  25                  30
Gly Pro Tyr Pro Leu Gly Ile Asn Gly Gly Met His Tyr Gly Val Asp
            35                  40                  45
Phe Phe Met Asn Ile Gly Thr Pro Val Lys Ala Ile Ser Ser Gly Lys
        50                  55                  60
Ile Val Glu Ala Gly Trp Ser Asn Tyr Gly Gly Asn Gln Ile Gly
65                  70                  75                  80
Leu Ile Glu Asn Asp Gly Val His Arg Gln Trp Tyr Met His Leu Ser
                85                  90                  95
Lys Tyr Asn Val Lys Val Gly Asp Tyr Val Lys Ala Gly Gln Ile Ile
```

-continued

```
                100                 105                  110
Gly Trp Ser Gly Ser Thr Gly Tyr Ser Thr Ala Pro His Leu His Phe
            115                 120                 125

Gln Arg Met Val Asn Ser Phe Ser Asn Ser Thr Ala Gln Asp Pro Met
            130                 135                 140

Pro Phe Leu Lys Ser Ala Gly Tyr Gly Lys Ala Gly Gly Thr Val Thr
145             150                 155                     160

Pro Thr Pro Asn Thr Gly Trp Lys Thr Asn Lys Tyr Gly Thr Leu Tyr
            165                 170                 175

Lys Ser Glu Ser Ala Ser Phe Thr Pro Asn Thr Asp Ile Ile Thr Arg
            180                 185                 190

Thr Thr Gly Pro Phe Arg Ser Met Pro Gln Ser Gly Val Leu Lys Ala
            195                 200                 205

Gly Gln Thr Ile His Tyr Asp Glu Val Met Lys Gln Asp Gly His Val
            210                 215                 220

Trp Val Gly Tyr Thr Gly Asn Ser Gly Gln Arg Ile Tyr Leu Pro Val
225             230                 235                     240

Arg Thr Trp Asn Lys Ser Thr Asn Thr Leu Gly Val Leu Trp Gly Thr
            245                 250                 255

Ile Lys Leu Val Pro Arg Gly Ser
            260
```

METHOD OF REDUCING BIOFILMS

Figure 1:
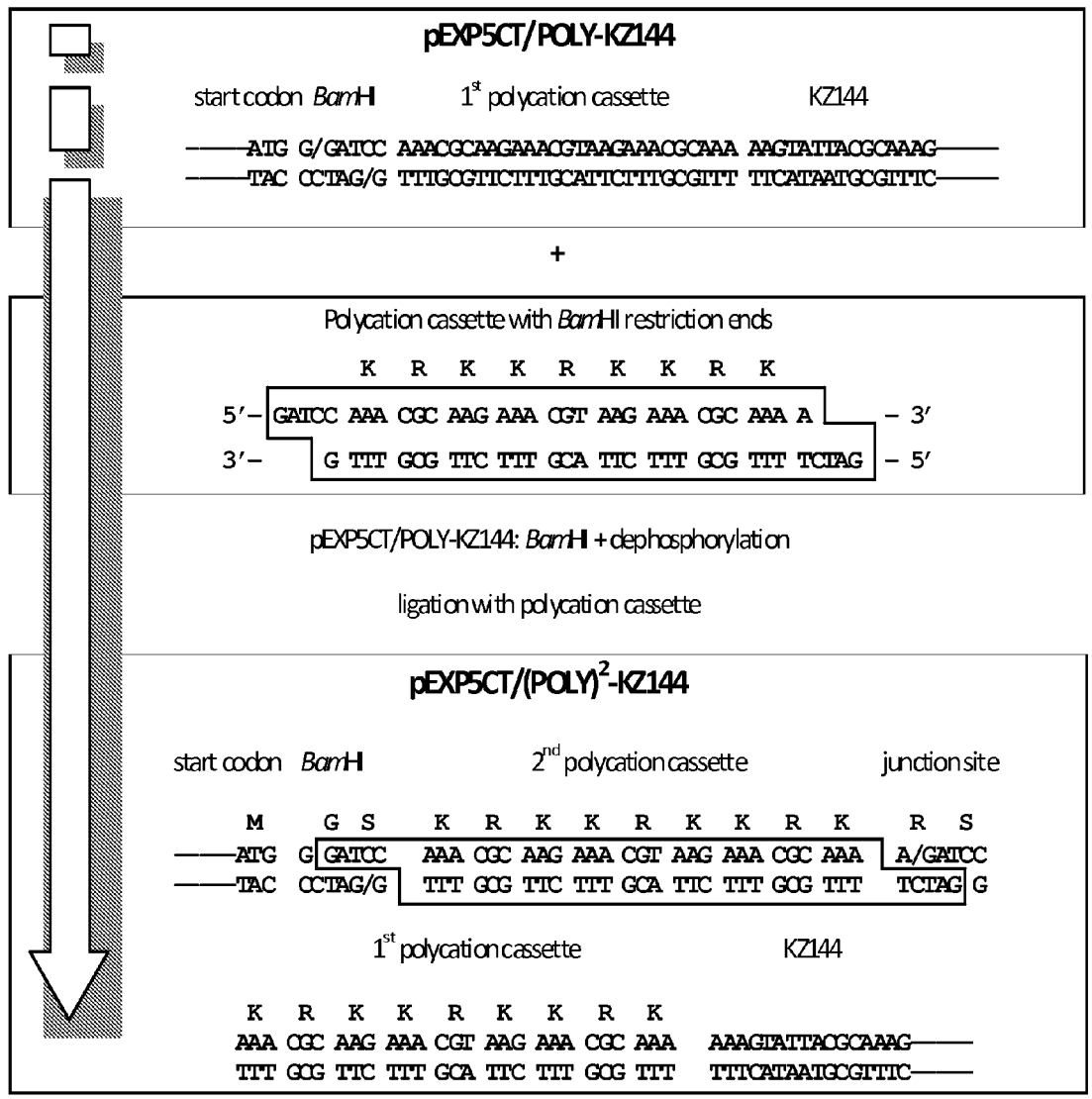

This application is a national phase application under 35 U.S.C. §371 of International Application No. PCT/EP2011/056657 filed 27 Apr. 2011, which claims priority to European Application No. 10 161 170.5 filed on 27 Apr. 2010. The entire text of each of the above-reference disclosures is specifically incorporated herein by reference without disclaimer.

The present invention relates to methods of eliminating, reducing or preventing bacterial biofilms by means of a fusion protein comprising an endolysin, an autolysin or a bacteriocin to which a peptide with membrane or LPS disrupting activity is fused. Further, the present invention relates to fusion proteins for use as a medicament, in particular for the treatment or prevention of Gram-negative and/or Gram-positive bacterial infections associated with bacterial biofilm, as diagnostic means, disinfectant or as cosmetic substance. The present invention also relates to the removal or reduction or prevention of Gram-negative and/or Gram-positive bacterial contamination associated with bacterial biofilm of foodstuff, of food processing equipment, of food processing plants, of surfaces coming into contact with foodstuff, of medical devices, of surfaces in hospitals and surgeries. Furthermore, the present invention relates to the use of said fusion protein as a diagnostic means in medicinal, food or feed or environmental diagnostic associated with bacterial biofilm.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β-(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage C1 endolysin towards group A streptococci (Nelson et al., 2001). Since then many publications have established endolysins as an attractive and complementary alternative to control bacterial infections, particularly by Gram-positive bacteria.

Subsequently different endolysins against other Gram-positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Therefore, the cation-binding sites are essential for the integrity of the outer membrane (Vaara, 1992). Polycationic agents such as poly-L-lysine polymers (of at least 20 residues) increase the outer membrane permeability by displacement of these stabilizing divalent cations. In addition, they exert a so-called 'self-promoted uptake' mechanism (Hancock and Wong, 1984). Due to their bulkiness, they disrupt the normal barrier function of the outer membrane and create transient cracks, promoting their own uptake (Vaara and Vaara, 1983). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

In contrast to Gram-negative bacteria, Gram-positive bacteria do not possess an outer membrane. The cytoplasmic membrane is surrounded by an up to 25 nm thick layer of peptidoglycan (which is only up to 5 nm for Gram-negative bacteria) which forms the cell wall. Main purpose of the cell wall of Gram-positives is to maintain bacterial shape and to counteract the internal bacterial cell pressure. Peptidoglycan, or murein, is a polymer consisting of sugars and amino acids. The sugar component consists of alternating residues of β-(1,4) linked N-acetylglucosamine and N-acetylmuramic acid residues compose the sugar components. A peptide chain of three to five amino acids is attached to the N-acetylmuramic acid. The peptide chain can be cross-linked to the peptide chain of another strand forming a 3D mesh-like layer. The peptide chain may contain D- and L-amino acid residues and the composition may vary for different bacteria.

Most Gram-negative bacteria, as well as many Gram-positive bacteria develop a bacterial biofilm. Biofilm is defined as an aggregate or association of microorganisms, which adhere to a surface. The adherent bacteria are often surrounded and protected by an extracellular polymer substance which is produced by the Gram-negative and Gram-positive bacteria. Due to the biofilm the bacteria are much more resistant to antimicrobial substances like antibiotics, disinfectants and cell wall degrading enzymes. In addition, the treatment of biofilms is currently not feasible because the extracellular polymer substance protects itself against degradation by antimicrobial substances, disinfectants or biofilm degrading substances.

Thus, there is a need for methods of eliminating, reducing or preventing bacterial biofilms.

This object is solved by the subject matter defined in the claims.

The following figures illustrate the present invention.

FIG. 1 is a schematic overview showing plasmid construction for recombinant production of (POLY)"-gp144 ((POLY)"-KZ144). Previously, pEXP5CT/POLY-gp144 (pEXPSCT/POLY-KZ144) was constructed by a tail PCR (with the BamHI restriction site and first polycation cassette in the 5' tail primer). The plasmid was linearized with BamHI, dephosphorylated and ligated with a cassette containing overhanging BamHI ends. This cassette originates from the hybridization of two complementary oligonucleotides and encodes 9 positively charged residues. One additional positive arginine residue is created at the junction site between the first and second cassette, together with a serine. Longer pEXP5CT/(POLY)''-gp144 (pEXP5CT/(POLY)''-KZ144) variants were constructed similarly by repeated cycles.

Figure 2:
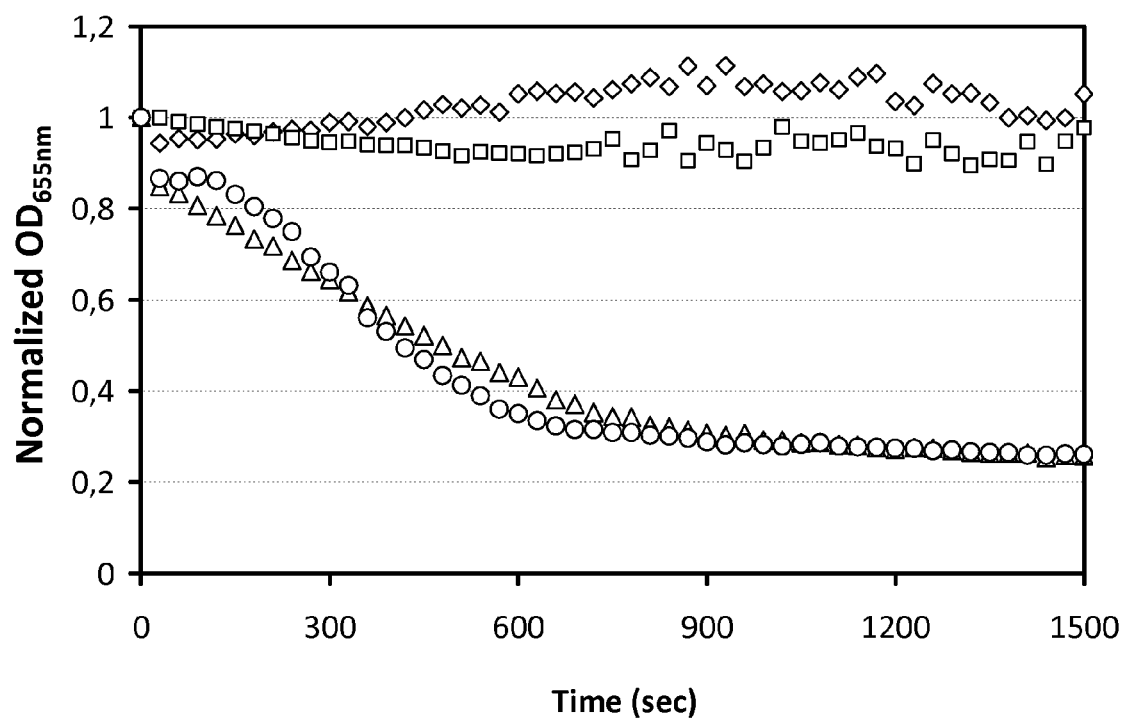

FIG. 2 shows the expression and secretion of POLY-gp144 by *Pichia pastoris*. An amount of 30 µl supernatant of a *P. pastoris* X33 expression culture [after 1 day (square), 3 days (triangle) and 4 days (circle)] is added to 270 µl chloroform-permeabilized *P. aeruginosa* PAO1p cells. The buffer conditions were the optimal enzymatic conditions of POLY-gp144 ($KH_2PO_4/K_2HPO_4$) I=120 mM pH 6.2). Subsequently, the optical density was spectrophotometrically recorded. A drop in optical density indicates the secretion of a muralytic enzyme by *P. pastoris*. As a negative control, *P. pastoris* X33 without expression plasmid is included (diamond).

Figure 3:
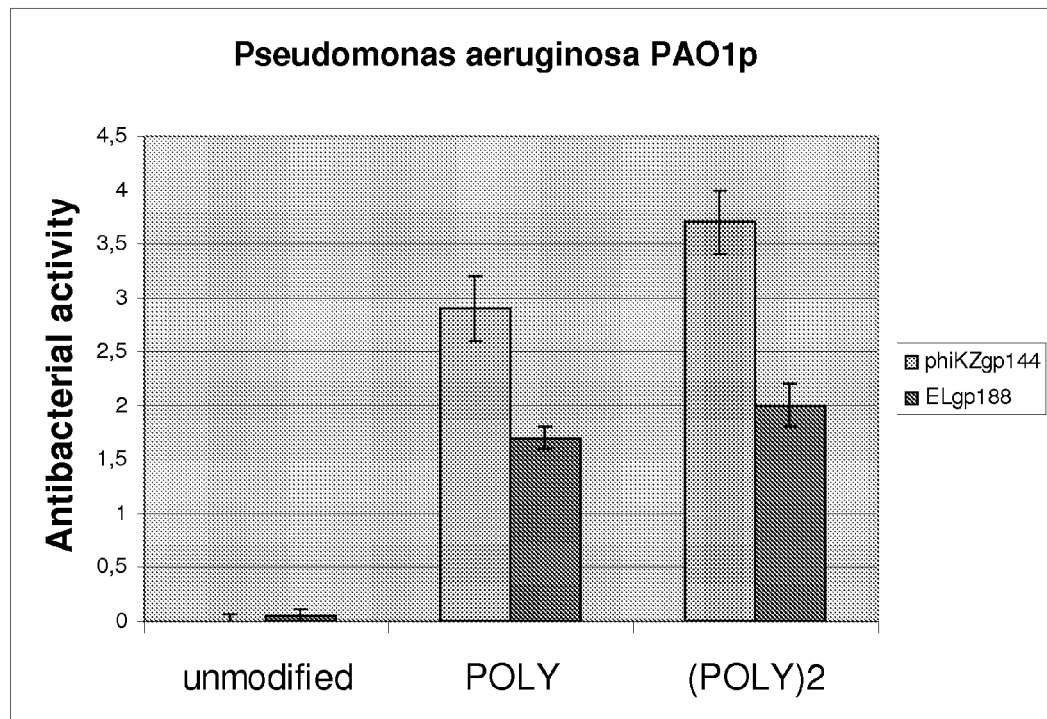

FIG. 3 shows in a graphical representation the antibacterial activity of the unmodified phiKZgp144 and ELgp188 endolysins, of the modified endolysin variants POLY-gp144 and POLY-gp188 comprising a peptide comprising 9 positively charged amino acid residues and of the modified variants (POLY)$^2$-gp144 and (POLY)$^2$-gp188 comprising a peptide comprising 18 positively charged amino acid residues on *Pseudomonas aeruginosa* PAO1p cells. The error bars render the standard deviations of the mean.

Figure 4:
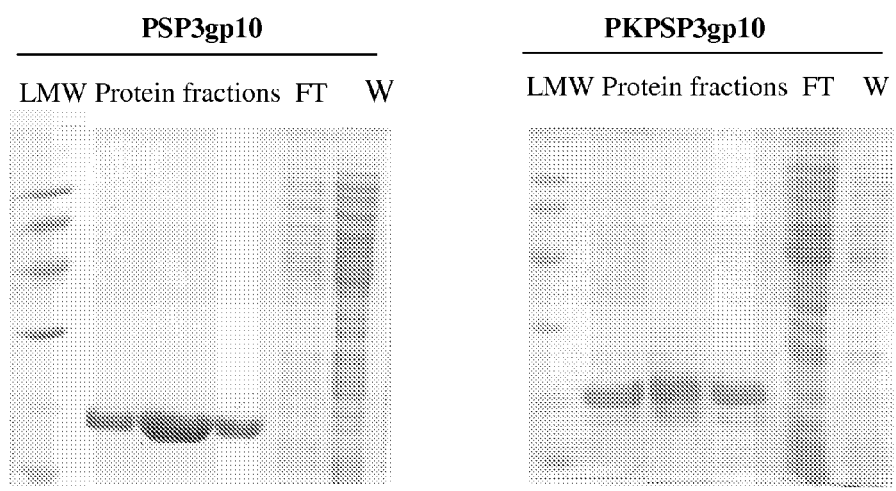

FIG. 4 shows a picture of a Coomassie-stained SDS-PAGE showing the results of the expression and purification of the unmodified endolysin PSP3gp10 and its modified endolysin variant PKPSP3gp10. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant proteins (>90%).

Figure 5:
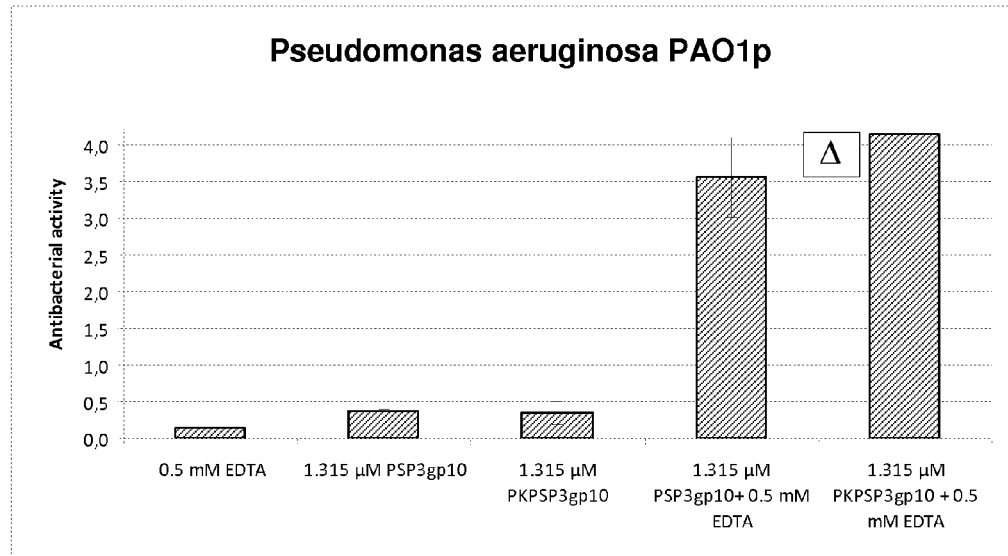
Figure 5:
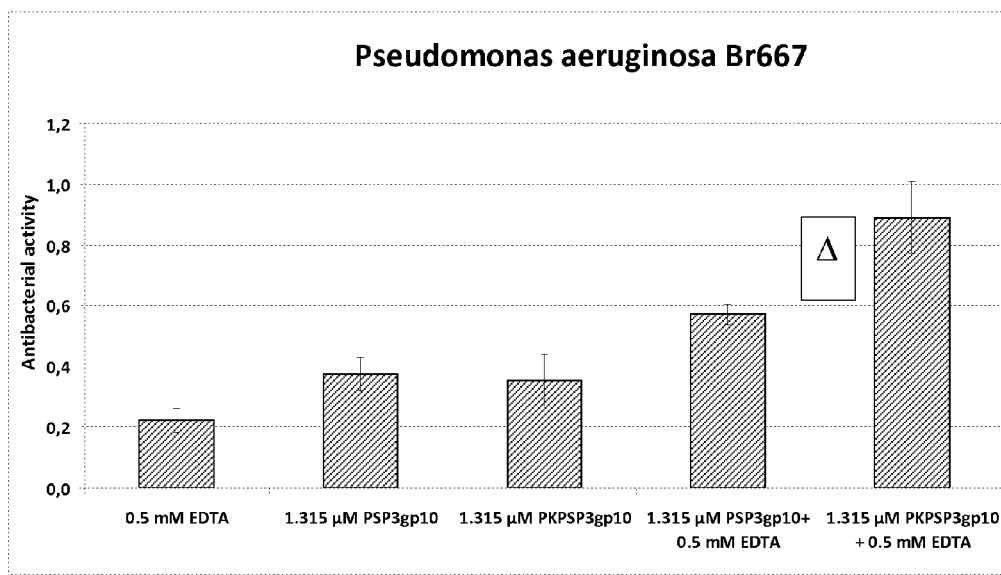
Figure 5:
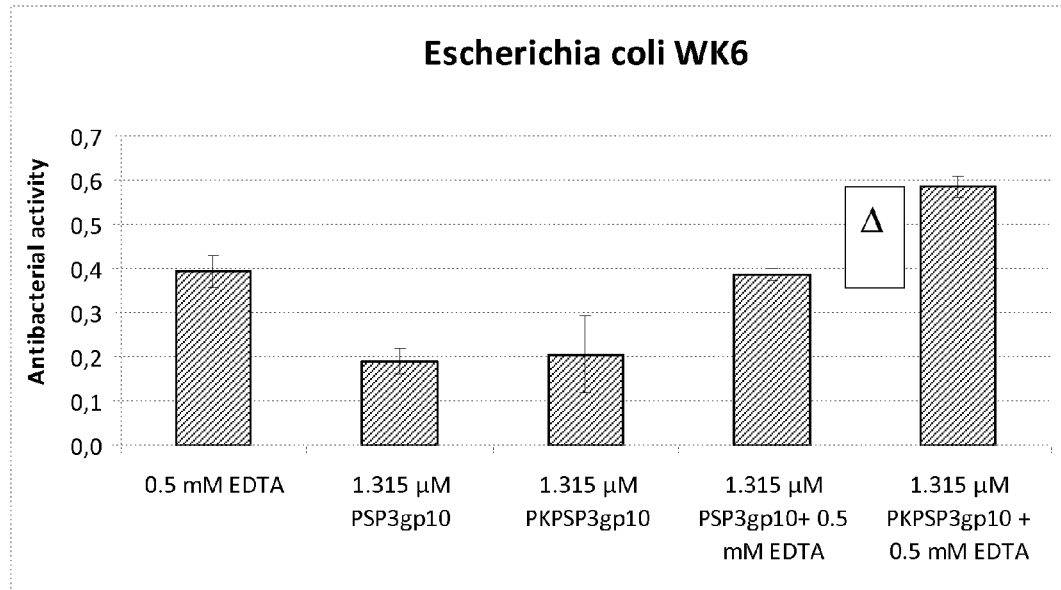
Figure 5:
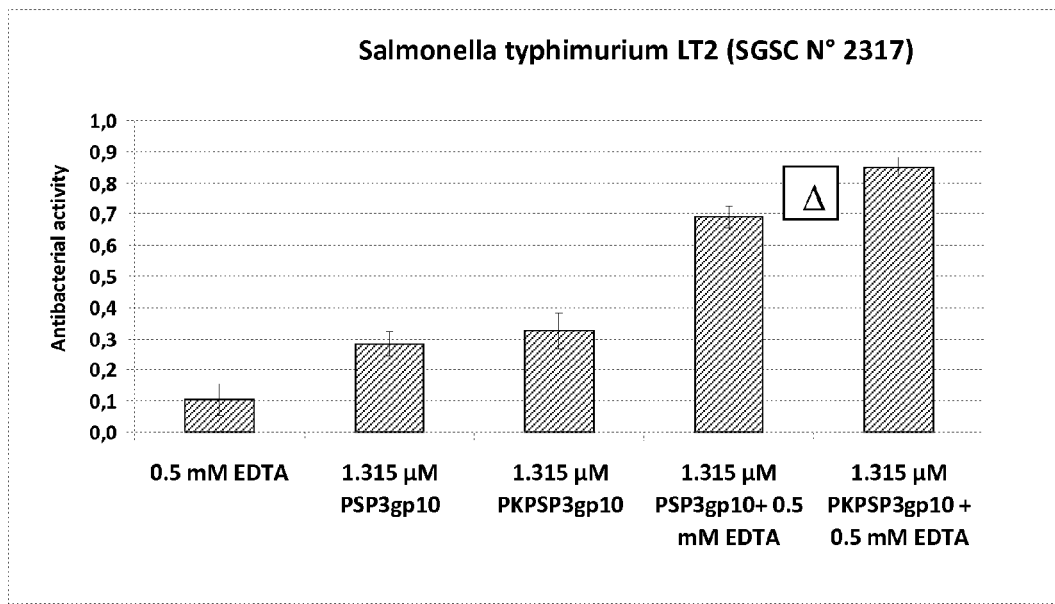

FIGS. 5 A to D show in a graphic representation the antibacterial activities of unmodified PSP3gp10 and the modified PKPSP3gp10 in different compositions on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified PSP3gp10 but no EDTA, with a composition comprising 1.315 µM modified PKPSP3gp10 but no EDTA, with a composition comprising 1.315 µM unmodified PSP3gp10 and 0.5 mM EDTA and with a composition comprising 1.315 µM modified PKPSP3gp10 and 0.5 mM EDTA. In FIG. 5 A the antibacterial activity on *P. aeruginosa* PAO1p cells is represented, in FIG. 5 B the antibacterial activity on *P. aeruginosa* Br667 cells, in FIG. 5 C the antibacterial activity on *E. coli* WK 6 cells and in FIG. 5 D the antibacterial activity on *Salmonella typhimurium* cells. "Δ" gives the difference of activity between the respective PSP3gp10 and PKPSP3gp10 samples. The error bars render the standard deviations of the mean.

Figure 6:
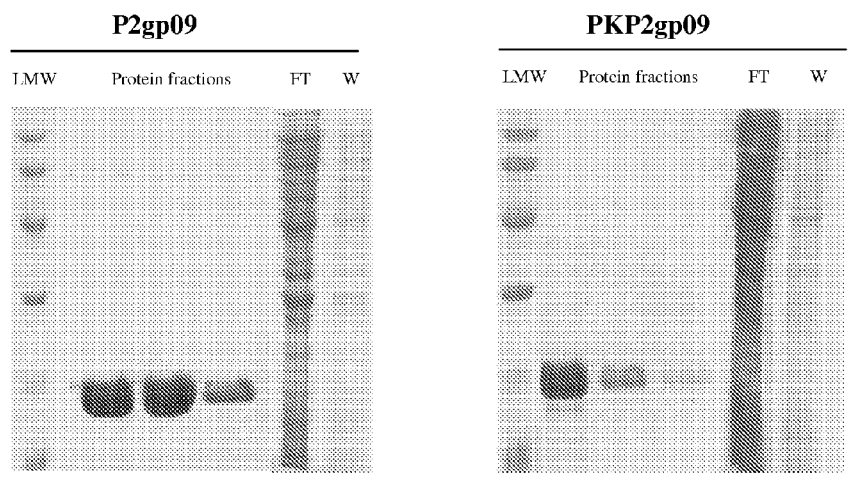

FIG. 6 shows a picture of a Coomassie-stained SDS-PAGE showing the results of the expression and purification of the unmodified endolysin P2gp09 and its modified endolysin variant PKP2gp09. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant protein (>95%).

Figure 7:
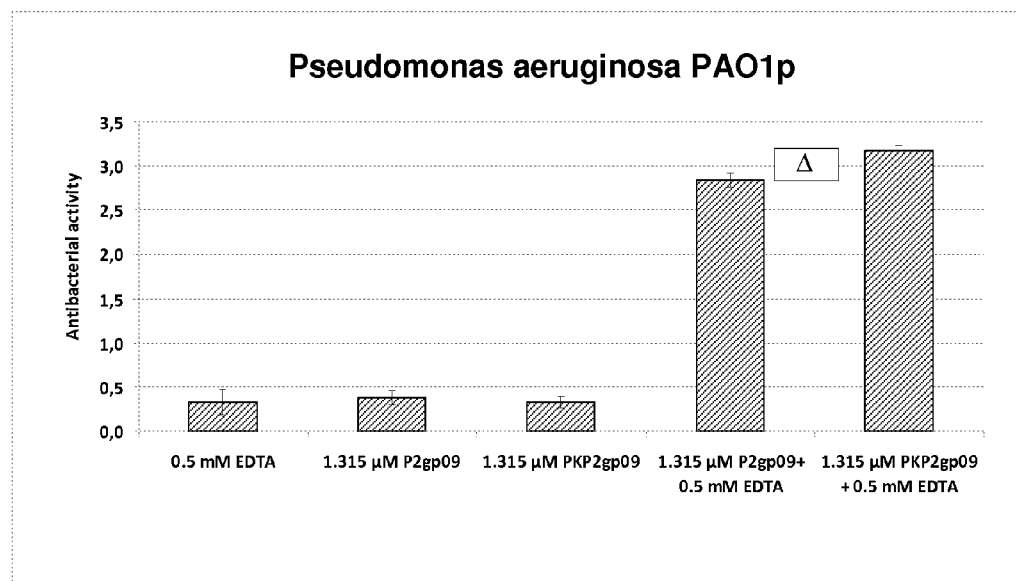
Figure 7:
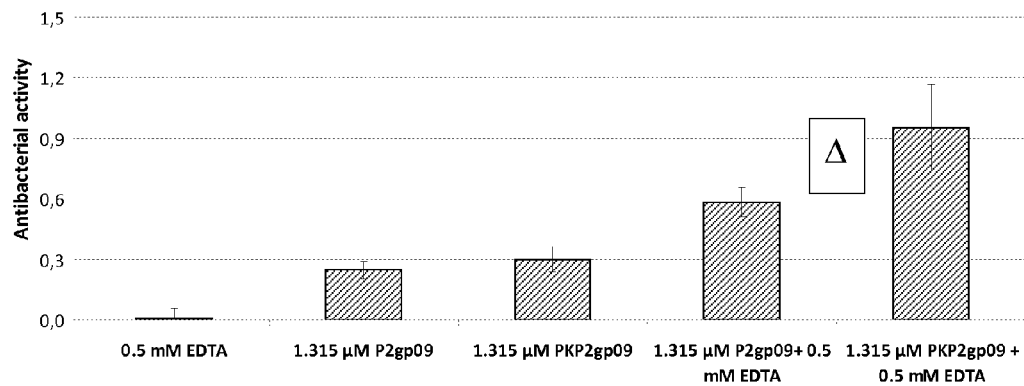
Figure 7:
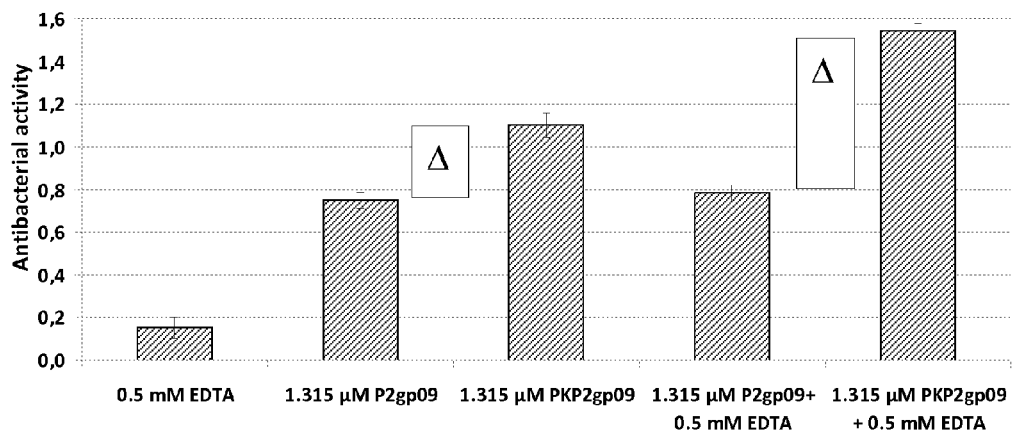
Figure 7:
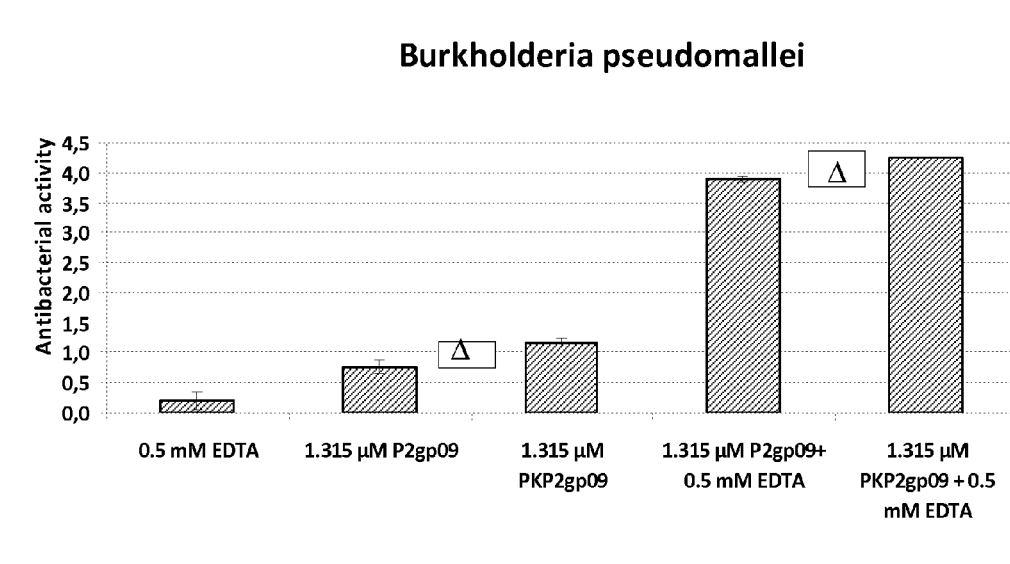
Figure 7:
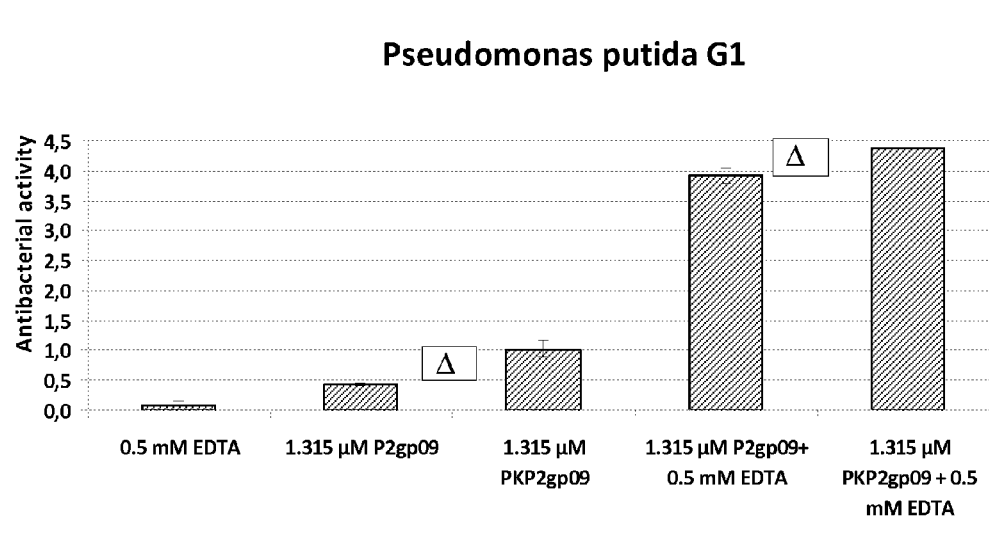
Figure 7:
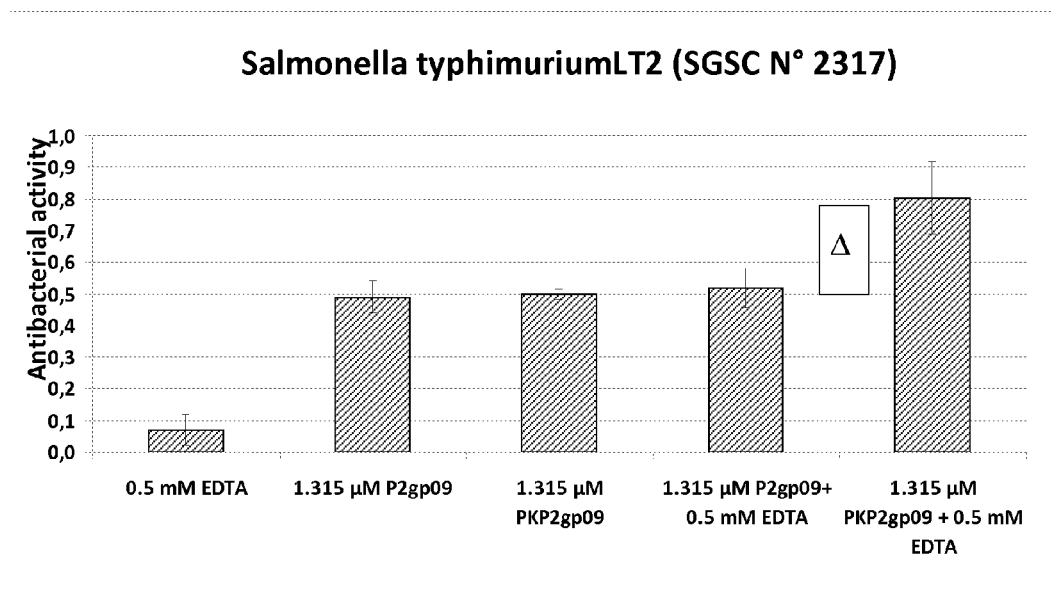

FIGS. 7 A to F show in a graphic representation the antibacterial activities of unmodified P2gp09 and the modified PKP2gp09 in different compositions on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified P2gp09 but no EDTA, with a composition comprising 1.315 µM modified PKP2gp09 but no EDTA, with a composition comprising 1.315 µM unmodified P2gp09 and 0.5 mM EDTA and with a composition comprising 1.315 µM modified PKP2gp09 and 0.5 mM EDTA. In FIG. 7 A the antibacterial activity on *P. aeruginosa* PAO1p cells is represented, in FIG. 7 B the antibacterial activity on *P. aeruginosa* Br667 cells, in FIG. 7 C the antibacterial activity on *E. coli* WK 6 cells, in FIG. 7 D the antibacterial activity on *Burkholderia pseudomallei* cells, in FIG. 7 E the antibacterial activity on *Pseudomonas putida* G1 cells and in FIG. 7 F the antibacterial activity on *Salmonella typhimurium* LT2 (SGSC No 2317) cells. "Δ" gives the difference of activity between the respective P2gp09 and PKP2gp09 samples. The error bars render the standard deviations of the mean.

Figure 8:
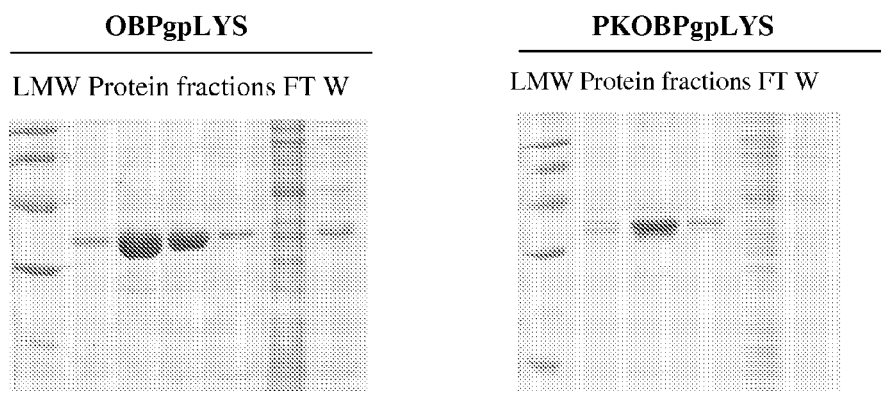

FIG. 8 shows a picture of a Coomassie-stained SDS-PAGE showing the results of the expression and purification of the unmodified endolysin OBPgpLYS and its modified endolysin variant PKOBPgpLYS. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant proteins (>90%).

Figure 9:
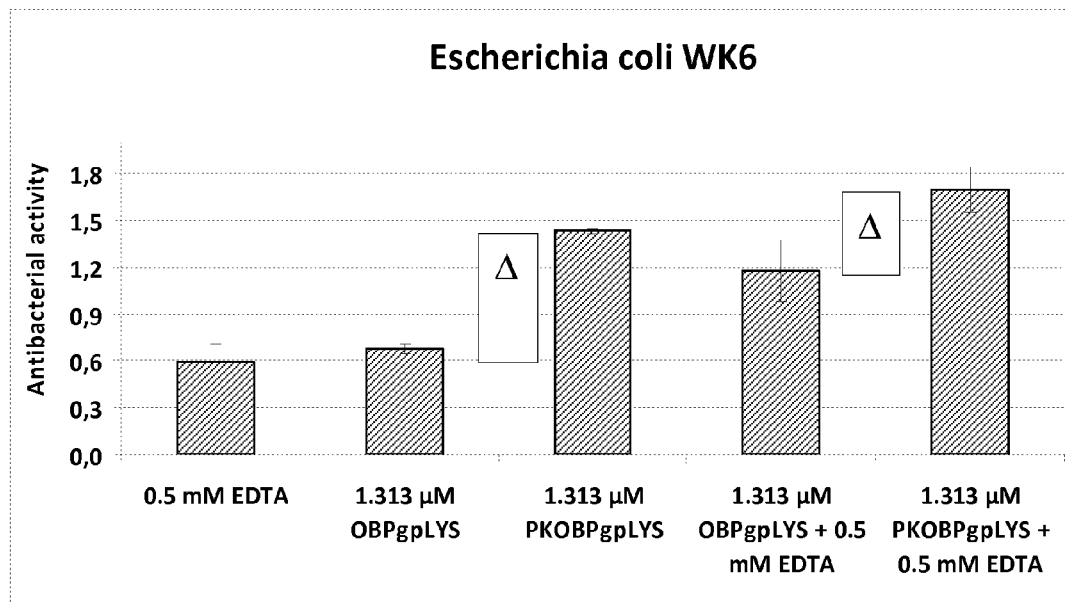
Figure 9:
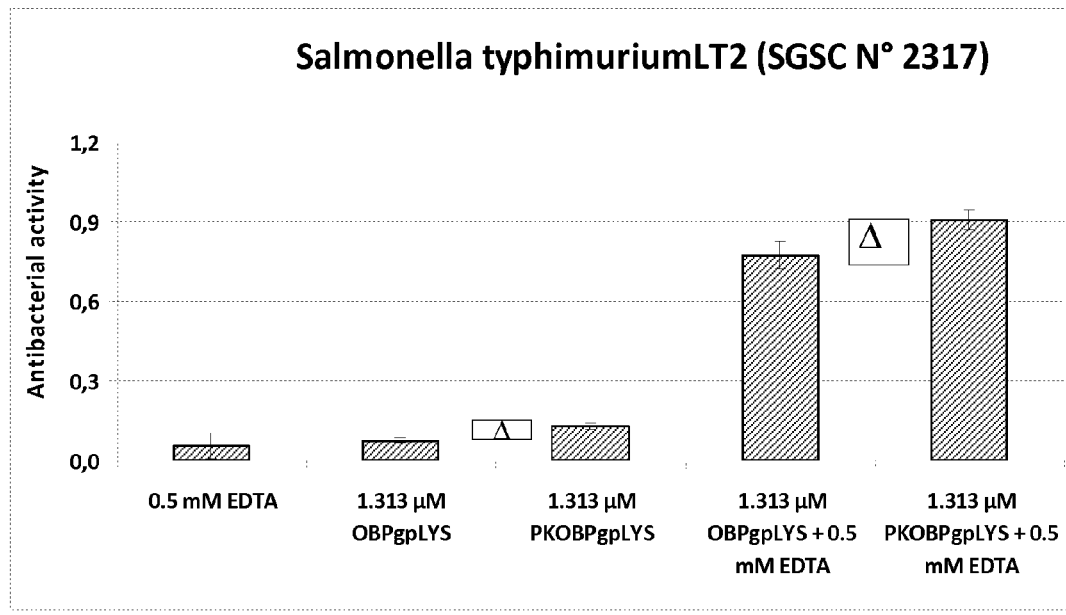
Figure 9:
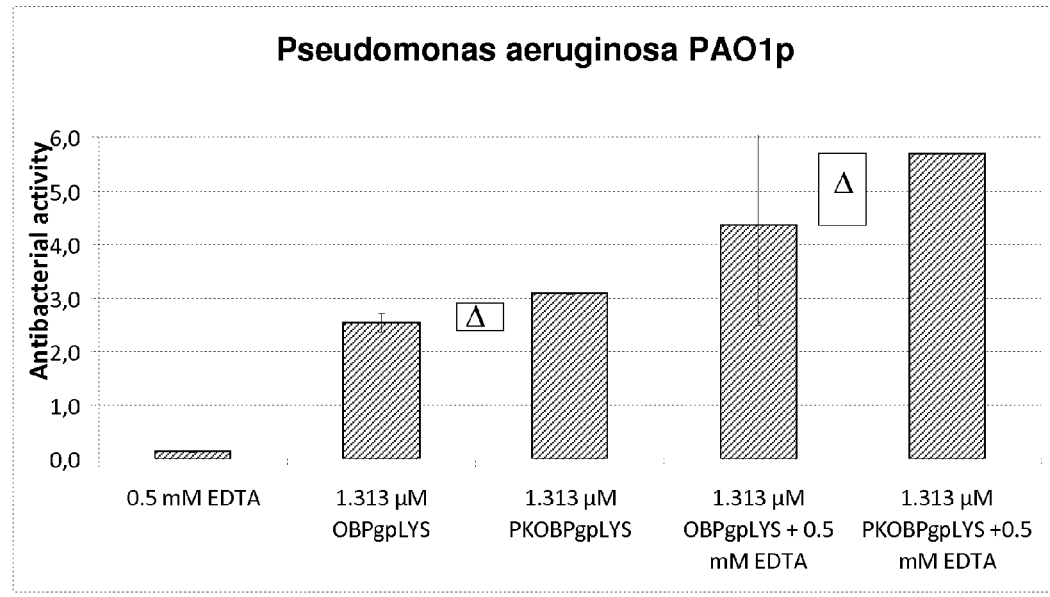
Figure 9:
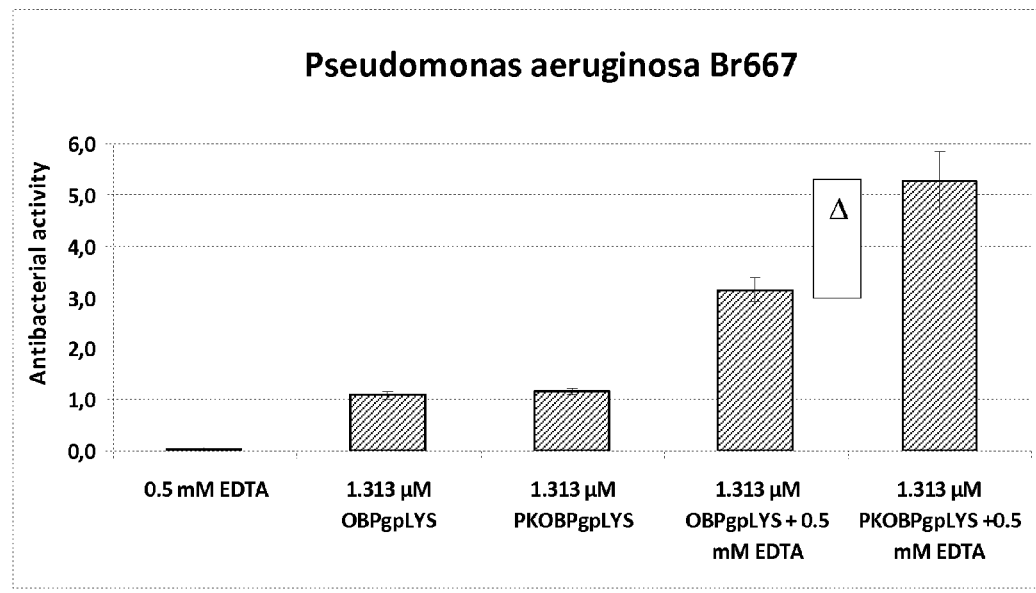
Figure 9:
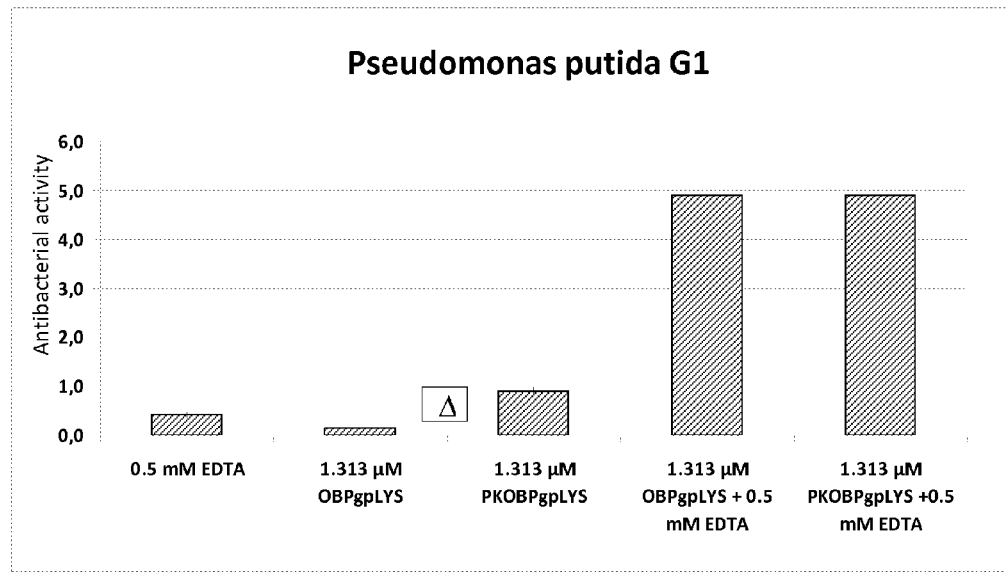
Figure 9:
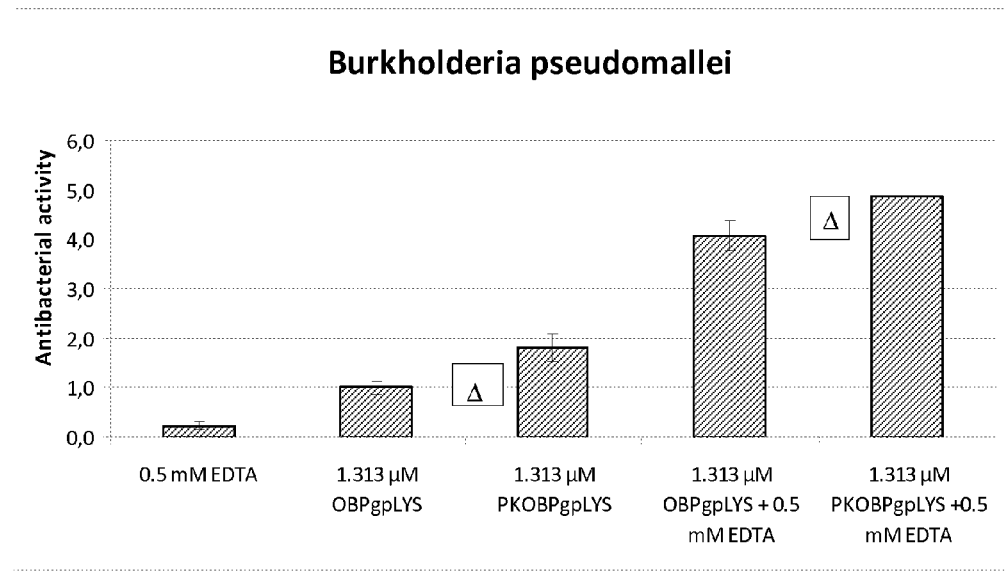

FIGS. 9 A to F show in a graphic representation the antibacterial activities of different compositions of unmodified OBPgpLYS and the modified PKOBPgpLYS on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified OBPgpLYS but no EDTA, with a composition comprising 1.315 µM modified PKOBPgpLYS but no EDTA, with a composition comprising 1.315 µM unmodified OBPgpLYS and 0.5 mM EDTA and with a composition comprising 1.315 µM modified PKOBPgpLYS and 0.5 mM EDTA. In FIG. 9 A the antibacterial activity on *Escherichia coli* WK6 cells is represented, in FIG. 9 B the antibacterial activity on *Salmonella typhimurium* LT2 (SGSC No 2317) cells, in FIG. 9 C the antibacterial activity on *Pseudomonas aeruginosa* PAO1p cells, in FIG. 9 D the antibacterial activity on *Pseudomonas aeruginosa* Br667 cells, in FIG. 9 E the antibacterial activity on *Pseudomonas putida* G1 cells and in FIG. 9 F the antibacterial activity on *Burkholderia pseudomallei* cells. "Δ" gives the difference of activity between the respective OBPgpLYS and PKOBPgpLYS samples. The error bars render the standard deviations of the mean.

Figure 10:
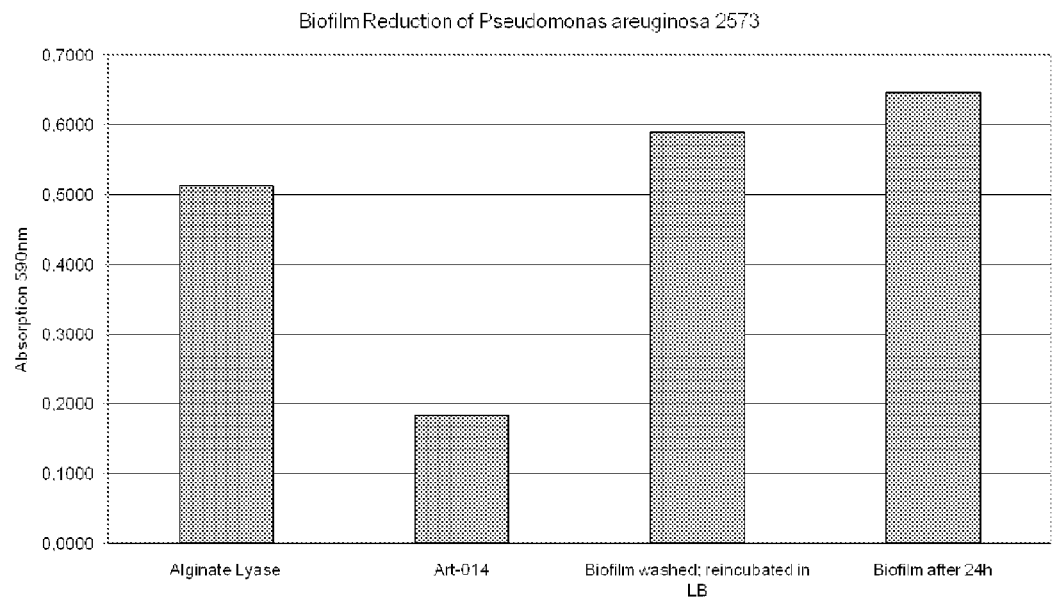
Figure 10:
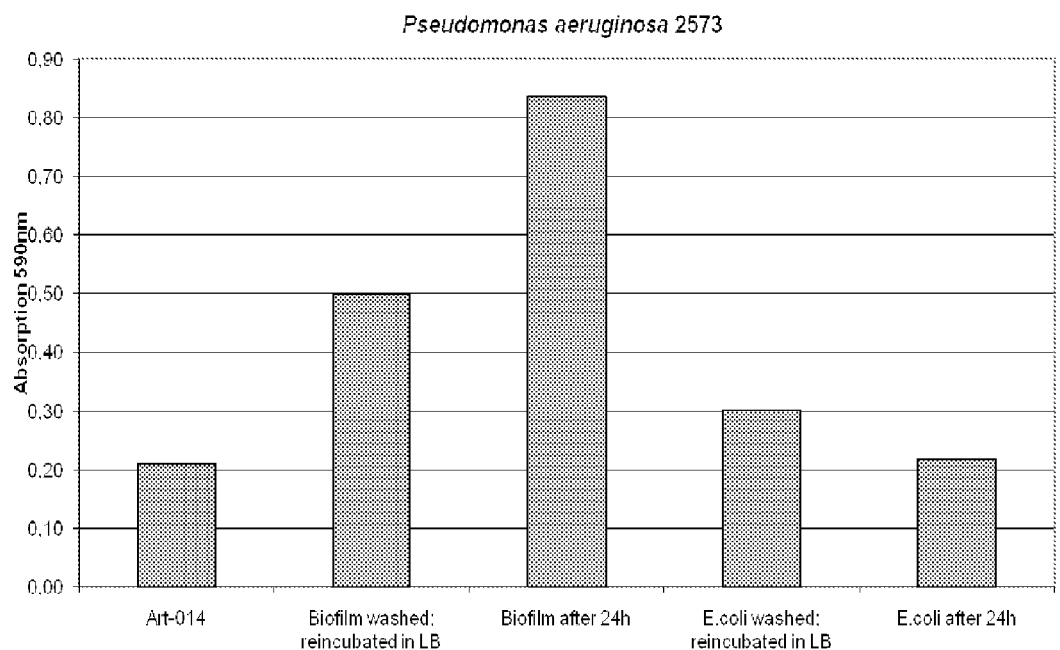

FIGS. 10 A and B show in a graphic representation the biofilm reducing activities of PolyKZ144 (Art-014) on a mucoid growing clinical isolate of *Pseudomonas aeruginosa* 2573 (Source Uniklinikum Regensburg, nicht näher definiert). *Pseudomonas aeruginosa* 2573 was grown at least 24 hours at 37° C. in a polystyrene microtiter plate to allow biofilm formation. To visualize the biofilm content crystal violet staining was performed. In FIG. 10 A, the biofilm was then incubated with either Alginate lyase (10 u/ml) or PolyKZ144 (50 µg/ml). The effect of both enzymes was compared to either biofilm untreated or biofilm washed and reincubated in LB-medium as controls. In FIG. 10 B the effect of PolyKZ144 was compared to either biofilm untreated or biofilm washed and reincubated in LB-medium as controls and a non mucoid growing *E. coli* lab strains to indicated unspecific background staining.

Figure 11:
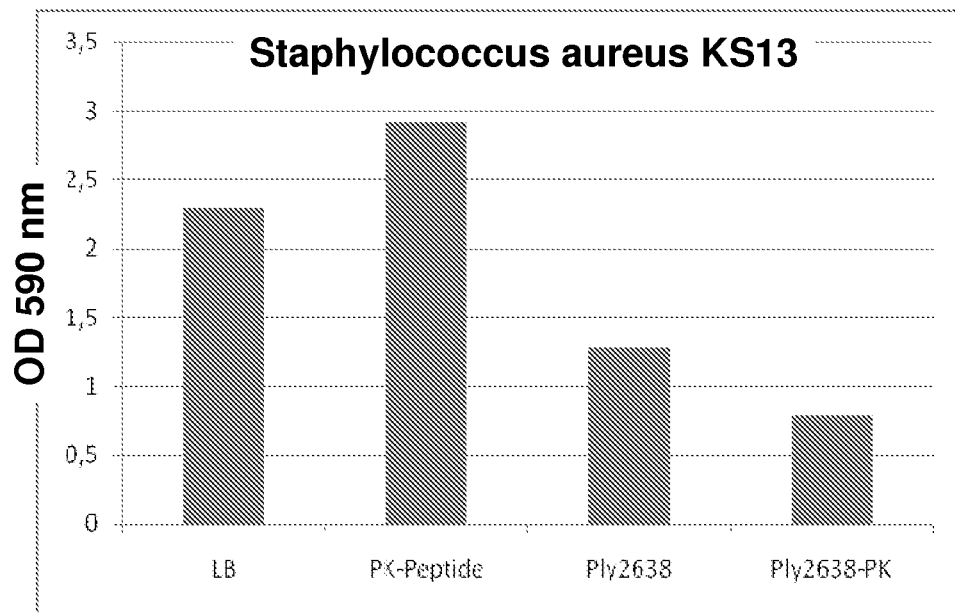
Figure 11:
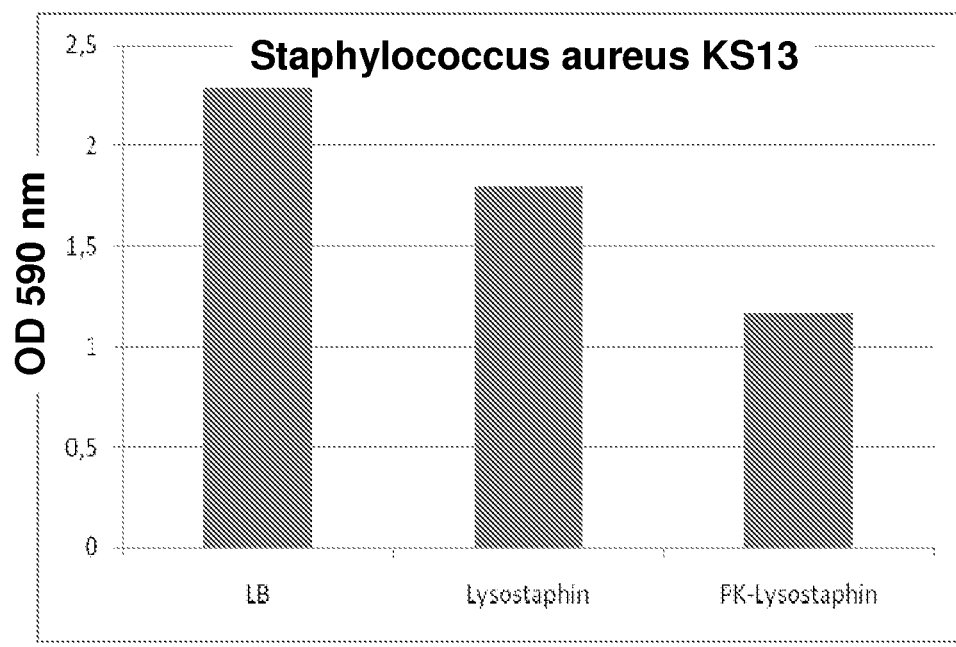
Figure 11:
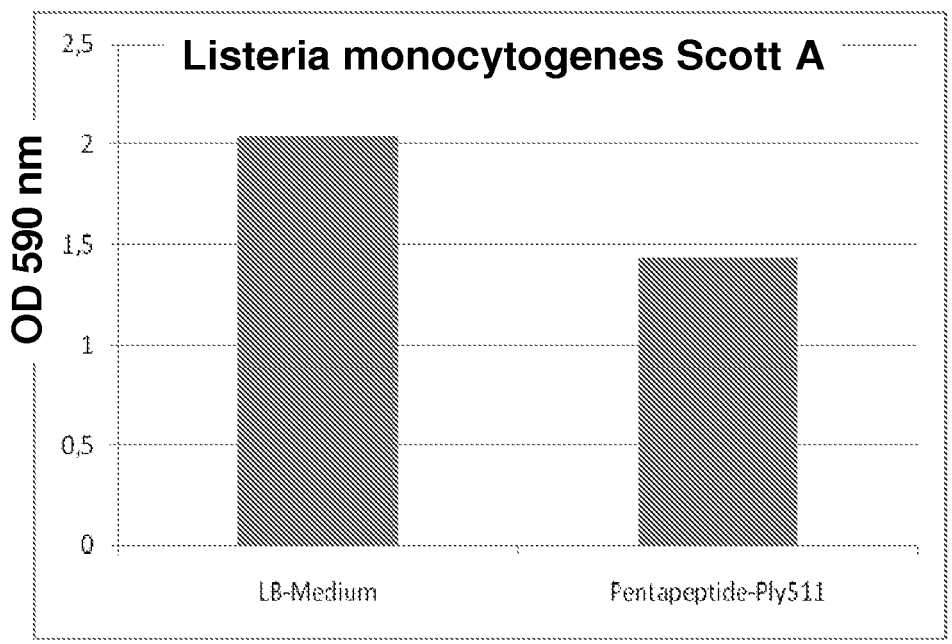
Figure 11:
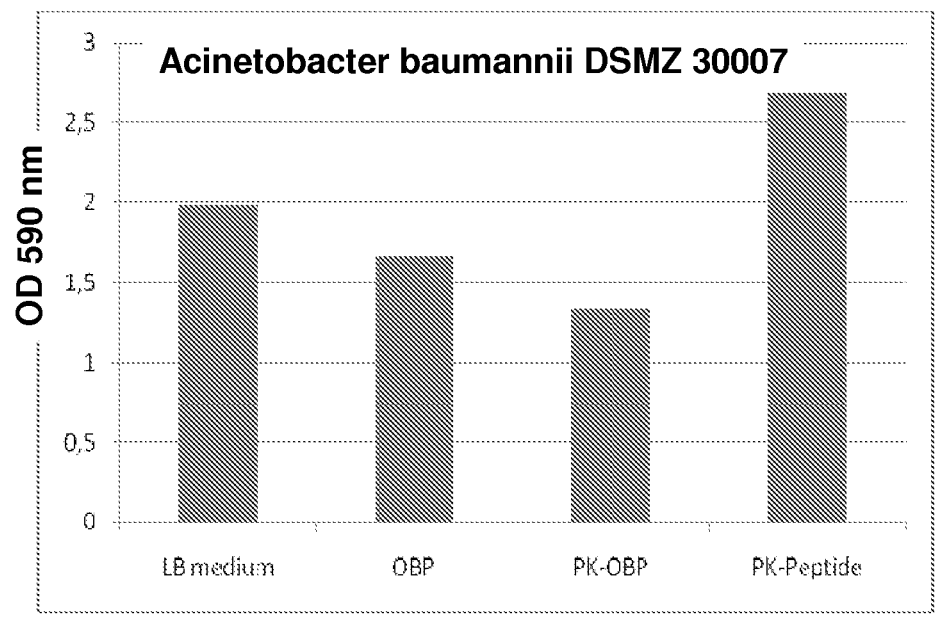
Figure 11:
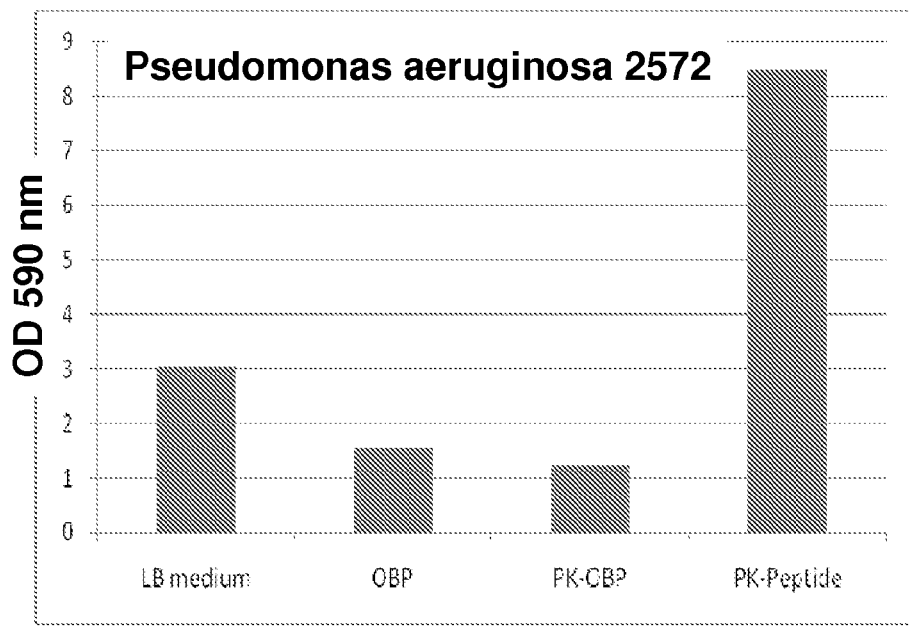
Figure 11:
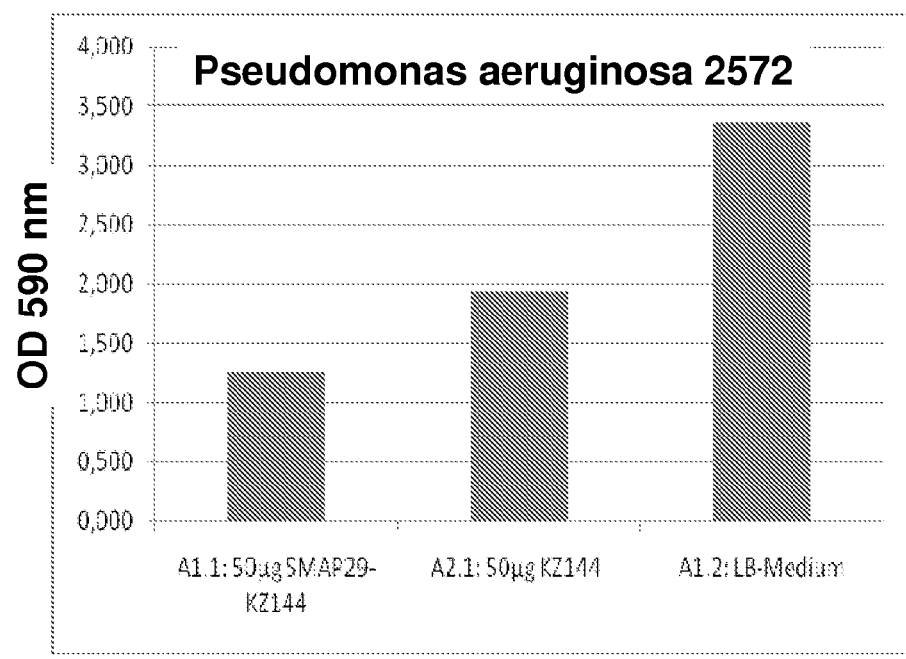
Figure 11:
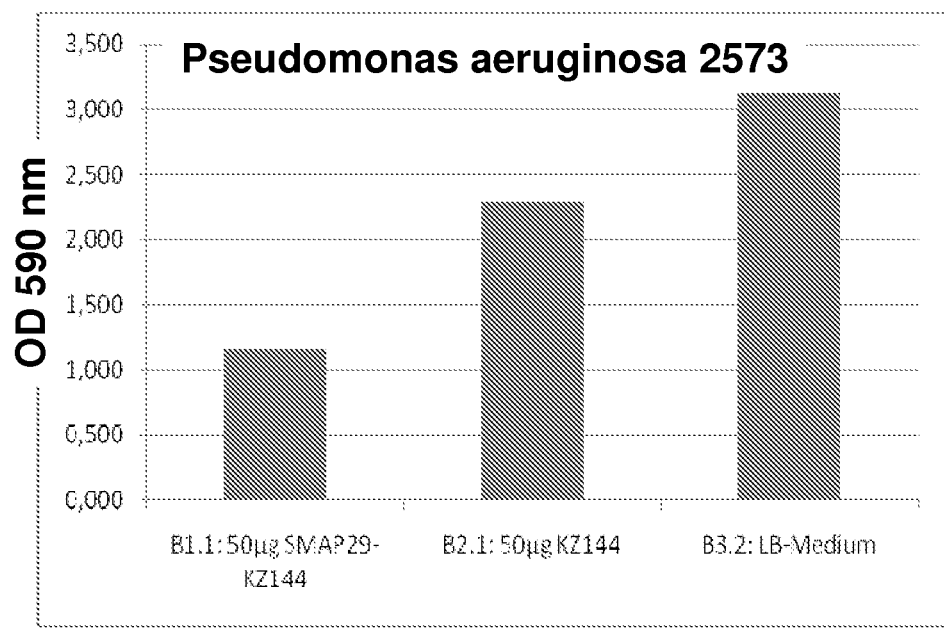

FIGS. 11 A to G show in a graphic representation the biofilm reducing activities of several fusion proteins on different Gram-positive and Gram-negative bacterial strains. *Staphylococcus aureus* KS13 (A and B), *Listeria monocytogenes* Scott A (C), *Acinetobacter baumannii* DSMZ30007 (D), *Pseudomonas aeruginosa* 2572 (E, F) and *Pseudomonas aeruginosa* 2573 (G) was grown at least 24 hours at 37° C. in a polystyrene microtiter plate to allow biofilm formation. To visualize the biofilm content crystal violet staining was performed. In FIG. 11 A, the biofilm was then incubated with either PK-Peptide (1.25 µg/well) or the endolysin Ply2638 (25 µg/well) or the fusion protein Ply2638-PK (25 µg/well). The effect of the peptide, the endolysin and the fusion protein was compared to biofilm untreated (one part protein buffer to one part 2×LB without NaCl) indicated by LB. In FIG. 11 B, the biofilm was then incubated with either the bacteriocin Lysostaphin (18 µg/well) or the bacteriocin variant PK-Lysostaphin (18 µg/well). The effect of the bacteriocin and the bacteriocin variant was compared to biofilm untreated (one part protein buffer to one part 2×LB without NaCl) indicated by LB. In FIG. 11 C, the biofilm was then incubated with the modified endolysin variant Pentapeptide-Ply511 (25 µg/well). The effect of the modified endolysin variant was compared to biofilm untreated (one part protein buffer to one part 2×LB without NaCl) indicated by LB. In FIGS. 11 D and E, the biofilm was then incubated with either PK-Peptide (1.25 µg/well) or the endolysin OBP (25 µg/well) or the modified endolysin variant PK-OBP (25 µg/well). The effect of the peptide, the endolysin and the modified endolysin variant was compared to biofilm untreated (one part protein buffer to one part 2×LB without NaCl) indicated by LB. In FIGS. 11 F and G, the biofilm was then incubated with either the endolysin KZ144 (50 µg/well) or the modified endolysin variant SMAP29-KZ144 (50 µg/well). The effect of the peptide, the endolysin and the modified endolysin variant was compared to biofilm untreated (one part protein buffer to one part 2×LB without NaCl) indicated by LB.

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the polypeptide chains, such as heme or lipid, giving rise to the conjugated proteins which are also comprised by the term "protein" as used herein. There are various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta. Moreover, the term "protein" refers to a complex, wherein the complex refers to a homomer.

The term "fusion protein" as used herein refers to an expression product resulting from the fusion of two nucleic acid sequences. Such a protein may be produced, e.g. in recombinant DNA expression systems or by chemical cross-linking. Moreover, the term "fusion protein" as used herein refers to a fusion of a first amino acid sequence, in particular an endolysin, an autolysin or a bacteriocin and/or other peptidoglycan hydrolase, with a second or further amino acid sequence. The second or further amino acid sequence is preferably a peptide, in particular a cationic, apolycationic, a hydrophobic, an amphiphatic and/or an antimicrobial peptide. Preferably, said second and/or further amino acid sequence is foreign to and not substantially homologous with any domain of the first amino acid sequence.

The term "modified endolysin variant" is used herein synonymously with the term "endolysin variant". Both terms refer to a fusion protein comprising an endolysin and a peptide, in particular a cationic, a polycationic, a hydrophobic, an amphiphatic and/or an antimicrobial peptide.

The term "modified bacteriocin variant" is used herein synonymously with the term "bacteriocin variant". Both terms refer to a fusion protein comprising a bacteriocin and a peptide, in particular a cationic, a polycationic, a hydrophobic, an amphiphatic and/or an antimicrobial peptide.

The term "modified autolysin variant" is used herein synonymously with the term "autolysin variant". Both terms refer to a fusion protein comprising an autolysin and a peptide, in particular a cationic, a polycationic, a hydrophobic, an amphiphatic and/or an antimicrobial peptide.

The term "peptide stretch" as used herein refers to any kind of peptide linked to a protein such as an endolysin, bacteriocin or autolysin. In particular the term "peptide stretch" as used herein refers to a cationic peptide, a polycationic peptide, an amphiphatic peptide, a hydrophobic peptide and/or an antimicrobial peptide. However, a peptide stretch in the meaning of the present invention does not refer to His-tags, preferably $His_5$-tags, $His_6$-tags, $His_7$-tags, $His_8$-tags, $His_9$-tags, $His_{10}$-tags, $His_{11}$-tags, $His_{12}$-tags, $His_{16}$-tags and $His_{20}$-tags, Strep-tags, Avi-tags, Myc-tags, Gst-tags, JS-tags, cystein-tags, FLAG-tags or other tags known in the art, thioredoxin or maltose binding proteins (MBP). The term "tag" in contrast to the term "peptide stretch" as used herein refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. However, the $His_6$-tag may, depending on the respective pH, also be positively charged, but is used as affinity purification tool as it binds to immobilized divalent cations and is not used as a peptide stretch according to the present invention.

The term "peptide" as used herein refers to short peptides consisting of from about 2 to about 100 amino acid residues, more preferably from about 4 to about 50 amino acid residues, more preferably to about 5 to 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Preferred synthetically produced peptides are e.g. cationic, polycationic, amphipathic or hydrophobic peptides. Preferred naturally occurring peptides are e.g. antimicrobial peptides.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides.

The term "polycationic peptide" as used herein refers to a synthetically designed and produced peptide composed of mostly positively charged amino acid residues, in particular lysine, arginine and/or histidine residues, more preferably lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers to any naturally occurring peptide that has microbicidal and/or microbistatic activity on for example bacteria, viruses, fungi, yeasts, mycoplasma and protozoa. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties, in particular sushi peptides and defensin. The antimicrobial peptide may be a member of the RNAse A super family, a defensin, cathelicidin, granulysin, histatin, psoriasin, dermicidine or hepcidin. The antimicrobial peptide may be naturally occurring in insects, fish, plants, arachnids, vertebrates or mammals.

Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring antimicrobial peptides.

The term "amphiphatic peptide" as used herein refers to synthetic peptides having both hydrophilic and hydrophobic functional groups. Preferably, the term "amphiphatic peptide" as used herein refers to a peptide having a defined arrangement of hydrophilic and hydrophobic groups e.g. amphiphatic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a nonaqueous environment. Examples of amino acid residues with hydrophobic side chains are valine, isoleucine, leucine, methionine, phenylalanine, tryptophan, cysteine, alanine, tyrosine, histidine, threonin, serine, proline and glycine residues.

The term "endolysin" as used herein refers to an enzyme which is suitable to hydrolyse bacterial cell walls. "Endolysins" comprise at least one "enzymatically active domain" (EAD) having at least one of the following activities: endopeptidase, N-acetyl-muramoyl-L-alanine-amidase (amidase), N-acetyl-muramidase, N-acetyl-glucosaminidase (lysozyme) or transglycosylases. In addition, the endolysins may contain also regions which are enzymatically inactive, and bind to the cell wall of the host bacteria, the so-called CBDs (cell wall binding domains). The endolysin may contain one, two or more CBDs. However, the term "endolysin" as used herein refers also to enzymes having at least one EAD but no CBDs. Generally, the cell wall binding domain is able to bind different components on the surface of bacteria. Preferably, the cell wall binding domain is a peptidoglycan binding domain and binds to the bacteria's peptidoglycan.

The term "cell wall" as used herein refers to all components that form the outer cell enclosure of the Gram-positive and Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "autolysins" as used herein refers to enzymes related to endolysins but encoded by bacteria and involved in e.g. cell division and cell wall metabolism. An overview of autolysins can be found in "Bacterial peptidoglycan (murein) hydrolases. Vollmer W, Joris B, Charlier P, Foster S. FEMS Microbiol Rev. 2008 March; 32(2):259-86".

The term "bacteriocin" as used herein refers to protein-like, polypeptide-like or peptide-like substances which are able to inhibit the growth of other bacteria. Some bacteriocins are capable of degrading bacterial cell walls like Lysostaphin (degrading *Staphylococcus* cell walls), Mutanolysin (degrading *Streptococcus* cell walls) and Enterolysin (degrading *Enterococcus* cell walls). Preferably said inhibition is specifically by means of absorption of said other bacteria to specific receptors of the bacteriocin. In general, bacteriocins are produced by microorganisms. However, the term "bacteriocin" as used herein refers both to an isolated form procuded by a microorganism or to a synthetically produced form, and refers also to variants which substantially retain the activities of their parent bacteriocins, but whose sequences have been altered by insertion or deletion of one or more amino acid residues.

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The term "biofilm" as used herein refers to an aggregate of bacterial microorganisms in which bacterial cells adhere to each other and/or to a surface. These adherent cells are often covered with a matrix of extracellular polymeric substance (EPS), which is produced by the cells. Biofilm EPS, is composed of extracellular DNA, proteins, and polysaccharides. These biofilms may form on any living or non-living surfaces, in particular on both on solid surfaces as colonies and on liquid surfaces as pellicles. Microbial cells growing in a biofilm are physiologically distinct from planktonic cells of the same organism.

The present invention relates to methods of eliminating, reducing or preventing of a bacterial biofilm comprising the steps of:
a) providing a fusion protein comprising an enzyme having the activity of degrading the cell wall of Gram-negative and/or Gram-positive bacteria to which a peptide with membrane or LPS disrupting activity is fused; and
b) contacting a material, liquid, surface or biological material with said fusion protein.

Preferably, the present invention relates to methods of eliminating, reducing or preventing of a bacterial biofilm comprising the steps of:
c) providing a fusion protein comprising an endolysin, autolysin or bacteriocin to which a peptide with membrane or LPS disrupting activity is fused; and
d) contacting a material, liquid, surface or biological material with said fusion protein.

The term "providing" a fusion protein according to the present invention refers either to the mere taking and using of the fusion protein according to the present invention or to the generating and purification of such fusion protein prior to the use according to the present invention.

Preferably, the material is a stone, rocks, soil, sediments, food, feed or cosmetics. Preferably, the liquid is water, such as drinking water, ground water or waste water, hot springs, seas, lakes, rivers, any kind of aequous systems, cleaning and storage solutions of contact lenses, dentures, implants, protheses, or braces.

Preferably, the biological material is any substance derived or obtained from a living organism, in particular plants and mammals, preferably humans, e.g. cells, tissues, organs, blood, blood components and body liquids. Preferably, cells are e.g. nucleated cells or anucleated cells. Cells can be derived from any organ in particular hepatocytes, smooth muscle cells, endothelial cells, keratinocytes, islet cells, stem cells (adult and neonatal, various tissues, or species origin), stem cell progenitor cells, cord blood cells, gametes (male and female), gamete progenitor cells, erythroblasts, leukoblasts, and chondroblasts. Tissues are e.g. mucous membranes, nerves, muscles, epithels, connective and supporting tissues, oral soft tissues and teeth. Organs are e.g. heart, heart valves, eye, ear, urinary tract, lungs, liver, kidney, biliary tract, prostate, nose, digestive tract, respiratory tract, gastrointestinal tract, brain and bone marrow. Preferred body liquids are urin, cerebrospinal fluid and lymph fluids.

Preferably, surfaces are solid biological or non-biotic surfaces. Preferred examples of surfaces are the surface of medical devices, in particular implants, protheses, cathethers, such as dental implants, urinary tract prostheses, peritoneal membrane and peritoneal dialysis catheters, indwelling catheters for hemodialysis and for chronic administration of chemotherapeutic agents (Hickman catheters), cardiac implants such as pacemakers, prosthetic heart valves, ventricular assist devices, synthetic vascular grafts and stents, internal fixation devices, percutaneous sutures and tracheal and ventilator tubing, as well as surfaces of industrial or potable water system piping and of natural aquatic systems.

Biofilms are formed by bacterial microorganisms in which bacterial cells adhere to each other and/or to a surface. Extracellular polymeric substances (EPS) excreted by the bacterial microorganisms of a biofilm form with water hydrogels, so that a slime-like matrix is formed. This matrix may also comprise gas bubbles and anorganic particles. Biofilm EPS, is composed of extracellular DNA, proteins, and polysaccharides. Besides the bacterial microorganisms other unicellular organisms may be integrated in the biofilm. Biofilms may occur by the settling of bacterial microorganisms to interfaces. Mostly, the biofilm is formed on water surfaces or on an interface to a solid phase. These biofilms may form on any living or non-living surfaces. In general all interfaces may be settled by biofilms. Biofilms are almost present everywhere, in soil and sediments, in ground water, on rocks, in desserts, in hot springs, on and in plants and animals, in particular on mucous membranes. Moreover, biofilms may occur on medical devices, such as implants, cathethers, endoscopes, protheses, instruments, and apparatus but also in cosmetics, food and feed. Biofilms may be also associated with infections, because in most cases the bacterial microorganisms form biofilm to be protected against the immune system. The formation of a biofilm ensures the long-term survival of the bacterial microorganisms. One example of an acute respiratory tract infection is the legionnaire's disease which is caused by swallowing or inhalation of clumps of *legionella*-biofilms detached from air or water pipes of heating or cooling systems. Also many food bacteria, like *E. coli* O157:H7, *Listeria monocytogenes*, *Yersinia enterocolitica*, *Salmonella* spp. and *Camphylobacter jejuni* may form on food and devices biofilms which are then highly resistant to biocides, drought, heat, antibiotics and cleaning reagents. The microorganisms responsible for infections of implants, catheters and other medical devices may be coagulase-negative staphylococci, *Staphylococcus aureus, Enterococcus faecalis, Streptococcus* spp., *Escherichia coli, Klebsiella pneumoniae, Acinetobacter* spp., *Proteus mirabilis, Pseudomonas aeruginsa* and *Candida* spp. which are also associated with a broad spectrum of nosocomial infections. Typical bacterial infections associated with biofilms in humans are: wound infections, in particular wounds associated with diabetes mellitus, tonsillitis, osteomyelitis, bacterial endocarditis, sinusitis, infections of the cornea, urinary tract infection, infection of the biliary tract, infectious kidney stones, urethritis, prostatitis, catheter infections, middle-ear infections, formation of dental plaque, gingivitis, periodontitis, cystic fibrosis, and infections of permanent indwelling devices such as joint prostheses and heart valves.

The presence of biofilms may be determined by various tests, such as by the Tissue culture plate method (TCP) described in Christensen et al., *J Clin Microbiol* 22:996-1006 (1985), or by the Tube method (TM) as previously described by Christensen et al., *Infect Immun* 37:318-26 (1982), or by the Congo red Agar method (CRA) described by Freeman et al., *J Clin Pathol* 42:872-4 (1989). The biofilm may be quantified by using crystal violet assay (Peeters et al., J Microbiol Methods 72: 157-165 (2008)).

The fusion protein according to the present invention may influence the interaction of the bacteria forming a biofilm so that the cells are transferred in single planktonic cells which where then lysed by said fusion protein, consequently the biofilm is then degraded in part or totally. The influence of the fusion protein according to the present invention on the bacteria may also directly lyse the bacteria associated in a biofilm and thus, the biofilm is degraded in part or totally. Moreover, the fusion protein according to the present invention may prevent the formation of bacterial biofilms by lysing bacteria which are able to form a biofilm with other bacteria.

The fusion proteins according to the present invention relate preferably to endolysin variants, bacteriocin variants and autolysin variants.

Preferred fusion proteins according to the present invention comprise an endolysin, an autolysin or a bacteriocin fused to a peptide with lipopolysachharide (LPS) or in general membrane disrupting activity. LPS is a major component of the outer membrane of Gram-negative bacteria. It increases the negative charge of the cell membrane and protects the membrane from certain kinds of chemical attack. To a certain degree said LPS protects the membrane of Gram-negative bacteria also from endolysins added from outside of the bacteria. However, the LPS can be disrupted by peptides having a LPS disrupting activity as e.g. positively charged peptides. Moreover, said peptides may be involved in the outer membrane protein transport mechanism, a destabilisation of structural outer membrane proteins and/or in lipid-dependent destabilisation. The inventors of the present invention have surprisingly found, that a peptide having LPS disrupting activity or in general membrane disrupting activity promotes the passage of an endolysin, an autolysin or a bacteriocin fused to said peptide through the outer membrane of Gram-negative bacteria. After the promoted pass of the endolysin, autolysin or bacteriocin through the outer membrane of bacteria, the cell wall of the bacterium can be more easily be disrupted or desintegrated by the endolysin due to degradation of the peptidoglycan layer followed by osmotic lysis when the internal cell pressure of the bacterium cannot longer be resisted. The Gram-positive bacteria have a much thicker peptidoglycan layer than Gram-negative bacteria. Here the membrane disrupting activity of the fusion protein supports the lysis of the bacteria, by acting on the cytoplasmic membrane.

Thus, the present invention refers to methods of eliminating, reducing or preventing bacterial biofilms by means of fusion proteins composed of an enzyme, preferably an endolysin, an autolysin or a bacteriocin, having the activity of degrading the cell wall of Gram-negative and/or Gram-positive bacteria and a peptide with membrane disrupting activity, wherein said peptide is fused to the enzyme at the N- and/or C-terminus. Said fusion proteins according to the present invention are also called modified endolysin variants or simply endolysin variants or modified endolysins, modified autolysin variants or autolysin variants, modified bacteriocins or bacteriocin variants.

The endolysin part of the fusion protein is preferably encoded by bacteriophages specific for Gram-negative bacteria such as Gram-negative bacteria of bacterial groups, families, genera or species comprising strains pathogenic for humans or animals like Enterobacteriaceae (*Escherichia*, especially *E. coli*, *Salmonella*, *Shigella*, *Citrobacter*, *Edwardsiella*, *Enterobacter*, *Hafnia*, *Klebsiella*, especially *K. pneumoniae*, *Morganella*, *Proteus*, *Providencia*, *Serratia*, *Yersinia*), Pseudomonadaceae (*Pseudomonas*, especially *P. aeruginosa*, *Burkholderia*, *Stenotrophomonas*, *Shewanella*, *Sphingomonas*, *Comamonas*), *Neisseria*, *Moraxella*, *Vibrio*, *Aeromonas*, *Brucella*, *Francisella*, *Bordetella*, *Legionella*, *Bartonella*, *Coxiella*, *Haemophilus*, *Pasteurella*, *Mannheimia*, *Actinobacillus*, *Gardnerella*, Spirochaetaceae (*Treponema* and *Borrelia*), Leptospiraceae, *Campylobacter*, *Helicobacter*, *Spirillum*, *Streptobacillus*, Bacteroidaceae (*Bacteroides*, *Fusobacterium*, *Prevotella*, *Porphyromonas*), *Acinetobacter*, especially *A. baumannii*.

In another preferred embodiment, the endolysin of the fusion protein is encoded by bacteriophages specific for Gram-positive bacteria such as Gram-positive bacteria of bacterial groups, families, genera or species comprising strains pathogenic for humans or animals, in particular of the phylum Actinobacteria, in particular of the class Actinobacteridae, in particular of the order Actinomycetales, in particular of the families Actinomycineae: Actinomycetaceae (Actinomyces, Mobiluncus), Corynebacterineae: Mycobacteriaceae (Mycobacterium), Nocardiaceae, Corynebacteriaceae, Frankineae: Frankiaceae, Micrococcineae: Brevibacteriaceae and Propionibacteriaceae (Propionibacterium) and of the order Bifidobacteriales, in particular of the families Bifidobacteriaceae (*Bifidobacterium*, *Falcivibrio*, *Gardnerella*) and other subclasses: Acidimicrobidae, Coriobacteridae, Rubrobacteridae, Sphaerobacteridae; and of the phylum Firmicutes, in particular of the class Bacilli, in particular of the order Bacillales, in particular of the families: Bacillaceae (*Bacillus*), Listeriaceae (*Listeria*), Staphylococcaceae (*Staphylococcus, Gemella, Jeotgalicoccus*) and of the order Lactobacillales, in particular of the families: Enterococcaceae (*Enterococcus*), Lactobacillaceae (*Lactobacillus, Pediococcus*), Leuconostocaceae (*Leuconostoc*), Streptococcaceae (*Lactococcus, Streptococcus*) and of the class Clostridia, in particular of the order: Clostridiales (*Clostridium, Peptostreptococcus, Selenomonas*), Halanaerobiales and Thermoanaerobacterales, and of the class Tenericutes/Mollicutes, in particular of the order: Mycoplasmatales (*Mycoplasma, Ureaplasma*), Entomoplasmatales (*Spiroplasma*), Anaeroplasmatales (*Erysipelothrix*), Acholeplasmatales (*Acholeplasma*), Haloplasmatales (*Haloplasma*).

In another preferred embodiment, the autolysin or the bacteriocin of the fusion protein is encoded by Gram-negative or Gram-positive bacteria such as Gram-negative or Gram-positive bacteria of bacterial groups, families, genera or species comprising strains pathogenic for humans or animals as listed above.

Preferably, the endolysin part derives from a phage or a wild type endolysin as depicted in the following table 1:

| phage | publication | Wild type endolysin | predicted function of the endolysin |
|---|---|---|---|
| ϕV10 | Perry, L. L. and Applegate, B. M. | PhiV10p30 | chitinase |
| FELS-1 | McClelland, M. and Wilson, R. K. | STM0907.Fels0 | chitinase |
| ε15 | Kropinksi, A. M. and McConnel, M. R. | epsilon15p25 | chitinase |
| YUA | Ceyssens. P. (Laboratory for Gene technology) | YuA20 | lytic transglycosylase (C)/1 transmembranair domain (N) |
| B3 | Braid, M. D. and Kitts, C. L. | ORF23 | lytic transglycosylase (C)/2 transmembranair domains (N) |
| BCEPμ | Summer, E. J. and Young, R. | BcepMu22 | lytic transglycosylase (M)/1 transmembranair domain (N) |
| F116 | Byrne, M. and Kropinski, A. M. | F116p62 | muraminidase (T4-like) |
| FELS-2 | McClelland, M. and Wilson, R. K. | STM2715.S.Fels2 | muraminidase (T4-like) |
| ES18 | Casjens, S. R. and Hendrix, R. W. | gp76 | muraminidase (T4-like) |
| SETP3 | De Lappe, N and Cormican, M. | SPSV3_gp23 | muraminidase (T4-like) |
| ϕECO32 | Savalia, D and Severinov, K | phi32_17 | muraminidase (T4-like) |
| HK022 | Juhala, R and Hendrix, R. W. | HK022p54 | muraminidase (lambdalike) |
| HK97 | Juhala, R and Hendrix, R. W. | HK97p58 | muraminidase (lambdalike) |
| HK620 | Clark, A. J. and Dhillon, T. S. | HK620p36 | muraminidase (lambdalike) |
| E1 | Pickard, D. and Dougan, G | VIP0007 | muraminidase (lambdalike) |
| SF6 | Casjens, S and Clark, A. J. | Sf6p62 | muraminidase (lambdalike) |
| SFV | Allison, G. E. and Verma, N. K. | R (SfVp40) | muraminidase (lambdalike) |
| BCEPC6B | Summer, E J and Young, R. | gp22 | muraminidase (lambdalike) |
| BCEPNAZGUL | Summer, E J and Young, R. | Nazgul38 | muraminidase (lambdalike) |
| P2 | Christie, G. E. and Calender, R. | K (P2p09) | muraminidase (lambdalike) |
| Wϕ | Christie, G. E. and Esposito, D. | K (Wphi09) | muraminidase (lambdalike) |
| RV5 | Kropinski, A. M. and Johnson | rv5_gp085 | muraminidase (lambdalike) |
| JS98 | Zuber, S and Denou, E. | EpJS98_gp116 | muraminidase (T4-like) |
| 13A | Savalia, D and Molineux, I. | gp3.5 | muramoyl-L-alanine amidase |
| BA14 | Savalia, D and Molineux, I. | gp3.5 | muramoyl-L-alanine amidase |
| ECODS1 | Savalia, D and Molineux, I. | gp3.5 | muramoyl-L-alanine amidase |
| K1F | Scholl, D and Merril, C | CKV1F_gp16 | muramoyl-L-alanine amidase |
| T3 | Pajunen, M. I. and Mollineux, I. J. | T3p18 | muramoyl-L-alanine amidase |
| GH-1 | Kropinski, A. M. and Kovalyova, I. V. | gh-1p12 | muramoyl-L-alanine amidase |
| K11 | Molineux, I. and Savalia, D. | gp3.5 | muramoyl-L-alanine amidase |
| BIP-1 | Liu, M and Miller, J. F. | bip-1p02 | lysozyme (N)/PG-binding domain (C) |
| BMP-1 | Liu, M and Miller, J. F. | bmp-1pO2 | lysozyme (N)/PG-binding domain (C) |
| BPP-1 | Liu, M and Miller, J. F. | bpp2 | lysozyme (N)/PG-binding domain (C) |
| ϕCTX | Nakayama, K and Hayashi, T. | ORF12 | PG-binding domain (N)/muramidase (C) |
| BCEP43 | Summer, E J and Young, R. | Bcep43-27 | PG-binding domain (N)/muramidase (C) |
| BCEP781 | Summer, E J and Young, R. | Bcep781-27 | PG-binding domain (N)/muramidase (C) |
| BCEP1 | Summer, E J and Young, R. | Bcep1-28 | PG-binding domain (N)/muramidase (C) |
| BCEPNY3 | Summer, E J and Young, R. | BcepNY3gene26 | PG-binding domain (N)/muramidase (C) |
| ϕE12-2 | DeShazer, D and Nierman, W. C. | gp45 | PG-binding domain (N)/muramidase (C) |
| ϕ52237 | DeShazer, D and Nierman, W. C. | gp28 | PG-binding domain (N)/muramidase (C) |
| ϕP27 | Recktenwald, J and Schmidt, H. | P27p30 | endopeptidase |
| RB49 | Monod, C and Krisch, H. M. | RB49p102 | endopeptidase |
| ϕ1 | Arbiol, C. and Comeau, A. M. | phi1-p102 | endopeptidase |
| T5 | Pankova, N. V. and Ksenzenko, V. N. | lys (T5.040) | endopeptidase |
| 201phi2-1 | Thomas et al., 2008 | | PG-binding domain (N)/unknown catalytic domain (C) |
| Aeh1 | Monod, C and Krisch, H. M. | Aeh1p339 | muraminidase (T4-like) |
| YYZ-2008 | Kropinski, A. M. | YYZgp45 | muraminidase (lambda-like) |

Also preferred is the endolysin part deriving from endolysins of the *Pseudomonas aeruginosa* phages ΦKZ and EL, of the *Pseudomonas putida* phage OBP, of the phage LUZ24, or from T4 lysozyme, gp61 muramidase, PSP3 endolysin, of the *Salmonella* phage, of the *Acinetobacter baumannii* phage, of the *E. coli* Phage P2, of the *E. coli* phage N4 and K1F and of the *Salmonella typhimurium* phage.

Further preferred endolysins of the fusion protein are *Listeria* phage endolysins PlyA118, PlyA500, PlyPSA, PlyA511, PlyP35, PlyP40, Staphylococcal phage Phi 11 endolysin, Phi MR11 endolysin, LysK, Ply 2638, *Clostridium perfringens* PlyS6, Ply3626, *Clostridium difficile*: CD27L endolysin, *Streptococcus*: B30 endolysin, phage Dp-1 Pal amidase, C1 endolysin, Cpl-1 endolysin, PlyGBS, *Enterococccus*: PlyV12, *Bacillus anthracis*: Phage gamma endolysin PlyG, *Propionibacterium* phage endolysin PA6-gp20.

Preferred autolysins of the fusion protein are described in: Bacterial peptidoglycan (murein) hydrolases. Vollmer W, Joris B, Charlier P, Foster S. FEMS Microbiol Rev. 2008 March; 32(2):259-86. Epub 2008 Feb. 11. Review. An example of a preferred autolysin is the AtlA Autolysine.

Preferred bacteriocins are Lysostaphin (degrading *Staphylococcus* cell walls), Mutanolysin (degrading *Streptococcus* cell walls) and Enterolysin (degrading *Enterococcus* cell walls). More preferably, the bacteriocin of the fusion protein according to the present invention comprises an amino acid sequence according to SEQ ID NO: 87.

Further examples for the endolysin part of the fusion protein is selected from the group consisting of Cpl-1 according to SEQ ID NO: 84, Ply511 according to SEQ ID NO: 85, LysK according to SEQ ID NO: 86, PA6-gp20 according to SEQ ID NO: 88, phiKZgp144 according to SEQ ID NO: 1, ELgp188 according to SEQ ID NO: 2, *Salmonella* endolysin according to SEQ ID NO: 3, *Enterobacteria* phage T4 endolysin according to SEQ ID NO: 4, *Acinetobacter baumannii* endolysin according to SEQ ID NO: 5, *E. coli* Phage K1F endolysin according to SEQ ID NO: 6, OBPgpLYS according to SEQ ID NO: 7, PSP3 *Salmonella* endolysin (PSP3gp10) according to SEQ ID NO: 8, *E. coli* Phage P2 endolysin (P2gp09) according to SEQ ID NO: 9, *Salmonella typhimurium* phage muramidase STM0016 according to SEQ ID NO: 89, *E. coli* Phage N4 muramidase N4-gp61 according to SEQ ID NO: 90, N4-gp61 trunc. according to SEQ ID NO:91 and Ply 2638 according to SEQ ID NO: 92.

In another preferred embodiment of the present invention methods of eliminating, reducing or preventing bacterial biofilms by means of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, PEGylation, chemical changes of the amino-, SH- or carboxyl-groups. Said modified and/or altered endolysins exhibit the lytic activity of the respective wild type endolysin. However, said activity can be higher or lower as the activity of the respective wild type endolysin. Said activity can be about 10, 20, 30, 40, 50, 60, 70, 80, 90, 100, 110, 120, 130, 140, 150, 160, 170, 180, 190 or about 200% of the activity of the respective wild-type endolysin or even more. The activity can be measured by assays well known in the art by a person skilled in the art as e.g. the plate lysis assay or the liquid lysis assay which are e.g. described in Briers et al., *J. Biochem. Biophys Methods* 70: 531-533, (2007).

The peptide of the fusion protein according to the present invention may be linked to the enzyme, preferably to the endolysin, autolysin or bacteriocin by additional amino acid residues e.g. due to cloning reasons. Preferably, said additional amino acid residues may be not recognized and/or cleaved by proteases. Preferably said peptide may be linked to the enzyme by at least 1, 2, 3, 4, 5, 6, 7, 8, 9 or 10 additional amino acid residues. Preferably, the peptide fused on the N-terminus of the enzyme, preferably to the endolysin, autolysin or bacteriocin, of the fusion protein according to the invention further comprises additional amino acids on its N-terminus. Preferably the peptide comprises the amino acid methionine (Met), or methionine, glycine and serine (Met-Gly-Ser) or alanine, methionine and glycine (Ala-Met-Gly). In another preferred embodiment the peptide is linked to the N-terminus of the enzyme, preferably to the endolysin, autolysin or bacteriocin, by the additional amino acid residues, in particular glycine and serine (Gly-Ser). In another preferred embodiment the peptide is linked to the C-terminus of the enzyme by the additional amino acid residues, in particular glycine and serine (Gly-Ser).

In one aspect of the present invention the peptide with membrane and/or LPS disrupting activity comprises a positively charged peptide, which comprises one or more of the positively charged amino acids being lysine, arginine and/or histidine. Preferably, more than 80%, preferably more than 90%, preferably 100% of the amino acids in said peptide are positively charged amino acids. Advantageously, the cationic peptide is positioned at the N-terminal and/or the C-terminal end of the fusion protein, thus enhancing the cationicity of the latter proteins. In another embodiment of the invention, the cationic peptide fused to the enzyme, preferably to the endolysin, autolysin or bacteriocin is at least 5, more preferably at least 9 amino acids long.

In a preferred embodiment said peptide comprises about 3 to about 50, more preferably about 5 to about 20, for instance about 5 to about 15 amino acid residues and at least 20, 30, 40, 50, 60 or 70%, more preferably at least 80%, for instance at least 90% of the said amino acid residues are either arginine or lysine residues. In another preferred embodiment said peptide comprises about 3 to about 50, more preferably about 5 to about 20, for instance about 5 to about 15 amino acid residues and said amino acid residues are either arginine or lysine residues.

Preferably, the peptide of the fusion protein is fused to the N-terminus and/or to the C-terminus of the enzyme, preferably of the endolysin, autolysin or bacteriocin. In a particular preferred embodiment said peptide is only fused to the N-terminus of the enzyme, preferably the endolysin, autolysin or bacteriocin. However, also preferred are fusion proteins having a peptide both on the N-terminus and on the C-terminus. Said peptides on the N-terminus and on the C-terminus can be the same or distinct peptides.

The peptide of the fusion protein is preferably covalently bound to the enzyme. Preferably, said peptide consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide comprising about 5 to about 100 amino acid residues, about 5 to about 50 or about 5 to about 30 amino acid residues. More preferred is a peptide comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In one aspect of the present invention the peptide is selected from the group of cationic peptides, polycationic peptides, hydrophobic peptides, antimicrobial peptides and amphiphatic peptides.

In one aspect of the present invention the peptide is a cationic and/or polycationic peptide, which comprises one or more of the positively charged amino acid residues of lysine, arginine and/or histidine, in particular of lysine and/or arginine. Preferably, more than about 20, 30, 40, 50, 60, 70, 75, 80, 85, 90, 95 or 99% of the amino acid residues in said peptide are positively charged amino acid residues, in particular lysine and/or arginine residues. Especially preferred are peptides consisting of about 100% positively charged amino acid residues, in particular arginine and/or lysine residues, wherein preferably about 60% to about 70% of said positively charged amino acid residues are lysine residues and about 30% to about 40% of said positively charged amino acid residues are arginine residues. More preferred is a peptide consisting of about 100% positively charged amino acid residues, in particular arginine and/or lysine residues, wherein preferably about 64% to about 68% of said positively charged amino acid residues are lysine and about 32% to about 36% of said positively charged amino acid residues are arginine. Peptides consisting of either only arginine or only lysine are also preferred.

Especially preferred are cationic and/or polycationic peptides of the fusion protein comprising at least one motive according to SEQ ID NO: 10 (KRKKRK). In particular cationic peptides comprising at least 2, 3, 4, 5, 6, 7, 8, 9, 10, 11, 12, 13, 14, 15, 16 or 17 motives according to SEQ ID NO: 10 (KRKKRK) are preferred. More preferred are cationic peptides comprising at least one KRK motive (lysarg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the peptide is a cationic peptide comprising beside the positively charged amino acid residues, in particular lysine and/or arginine residues, neutrally charged amino acid residues, in particular glycine and/or serine residues. Preferred are cationic peptides consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are peptides consisting of about 4% to about 8% serine residues, of about 33% to about 36% arginine residues and of about 56% to about 63% lysine residues. Especially preferred are peptides comprising at least one motive according to SEQ ID NO: 32 (KRXKR), wherein X is any other amino acid than lysine, arginine and histidine. Especially preferred are peptides comprising at least one motive according to SEQ ID NO: 33 (KRSKR). More preferred are cationic peptides comprising at least about 2, 3, 4, 5, 6, 7, 8, 9, 10, 11, 12, 13, 14, 15, 16, 17, 18, 19 or about 20 motives according to SEQ ID NO: 32 (KRXKR) or SEQ ID NO: 33 (KRSKR).

Also preferred are peptides of the fusion protein consisting of about 9 to about 16% glycine residues, of about 4 to about 11% serine residues, of about 26 to about 32% arginine residues and of about 47 to about 55% lysine residues. Especially preferred are peptides comprising at least one motive according to SEQ ID NO: 34 (KRGSG). More preferred are cationic peptides comprising at least about 2, 3, 4, 5, 6, 7, 8, 9, 10, 11, 12, 13, 14, 15, 16, 17, 18, 19 or about 20 motives according to SEQ ID NO: 34 (KRGSG).

In another preferred embodiment of the present invention the cationic peptide comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. Preferred are cationic peptides of the fusion protein consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues.

Especially preferred are peptides of the fusion protein selected from the group consisting of the following sequences presented in Table 2.

TABLE 2

| Peptide | length | SEQ ID NO: |
|---|---|---|
| KRKKRK | 6 | SEQ ID NO: 10 |
| KRKKRKKRK | 9 | SEQ ID NO: 11 |
| RRRRRRRRR | 9 | SEQ ID NO: 12 |
| KKKKKKKK | 8 | SEQ ID NO: 13 |
| KRKKRKKRKK | 10 | SEQ ID NO: 14 |
| KRKKRKKRKKRK | 12 | SEQ ID NO: 15 |
| KRKKRKKRKKRKKR | 14 | SEQ ID NO: 16 |
| KKKKKKKKKKKKKKKK | 16 | SEQ ID NO: 17 |
| KRKKRKKRKKRKKRKKRKK | 19 | SEQ ID NO: 18 |
| RRRRRRRRRRRRRRRRRRR | 19 | SEQ ID NO: 19 |
| KKKKKKKKKKKKKKKKKKK | 19 | SEQ ID NO: 20 |
| KRKKRKKRKRSKRKKRKKRK | 20 | SEQ ID NO: 21 |
| KRKKRKKRKRSKRKKRKKRKK | 21 | SEQ ID NO: 22 |
| KRKKRKKRKRKKRKKRKKRK | 21 | SEQ ID NO: 23 |
| KRKKRKKRKRGSGKRKKRKKRK | 22 | SEQ ID NO: 24 |
| KRKKRKKRKRGSGSGKRKKRKKRK | 24 | SEQ ID NO: 25 |
| KRKKRKKRKRKKRKKRKKRKKRKK | 25 | SEQ ID NO: 26 |
| KRKKRKKRKRSKRKKRKKRKRSKRKKRKKRK | 31 | SEQ ID NO: 27 |
| KRKKRKKRKRGSGSGKRKKRKKRKRGSGSGKRKKRKKRK | 38 | SEQ ID NO: 28 |

TABLE 2-continued

| Peptide | length | SEQ ID NO: |
|---|---|---|
| KRKKRKKRKKRKKRKKRKKRKKRKKRKKRKKRKKRKKRK | 39 | SEQ ID NO: 29 |
| KRKKRKKRKRSKRKKRKKRKRSKRKKRKKRKRSKRKKRKKRK | 42 | SEQ ID NO: 30 |

Preferably, the peptide of the fusion protein is no tag such as a His-tag, Strep-tag, Avi-tag, Myc-tag, Gst-tag, JS-tag, cystein-tag, FLAG-tag or other tags known in the art and no thioredoxin or maltose binding proteins (MBP). However, the fusion protein according to the present invention may comprise in addition such tag or tags.

Preferably, the peptide of the fusion protein has the function to lead the fusion protein according to the present invention through the outer membrane of bacteria but has no or only low activity when administered without being fused to the endolysin, autolysin or bacteriocin. The function to lead the fusion protein through the outer membrane of Gram-negative and/or Gram-positive bacteria is caused by the potential of the outer membrane or LPS disrupting or permeabilising or destabilizing activity of said peptide. Such outer membrane or LPS disrupting or permeabilising or destabilizing activity of the peptide may be determined in a method as follows: The bacteria cells to be treated are cultured in liquid medium or on agar plates. Then the bacteria cell concentration in the liquid medium is determined photometrically at OD600nm or the colonies on the agar plates are counted, respectively. Now, the bacteria cells in liquid medium or on the plates are treated with a fusion protein according to the invention. After incubation the bacteria cell concentration in the liquid medium is determined photometrically at OD600nm or the colonies on the agar plates are counted again. If the fusion protein exhibits such outer membrane or LPS disrupting or permeabilising or destabilizing activity, the bacteria cells are lysed due to the treatment with the fusion protein and thus, the bacteria cell concentration in the liquid medium or the number of the bacteria colonies on the agar plate is reduced. Thus, the reduction in bacteria cell concentration or in the number of bacteria colonies after treatment with fusion protein is indicative for an outer membrane or LPS disrupting or permeabilising or destabilizing activity of the fusion protein.

In a further embodiment of the present invention the peptide is an antimicrobial peptide comprising a positive net charge and around 50% hydrophobic amino acids. The antimicrobial peptides are amphiphatic, with a length of about 12 to about 50 amino acid residues. The antimicrobial peptides are naturally occurring in insects, fish, plants, arachnids, vertebrates or mammals. Preferably the antimicrobial peptide may be naturally occurring in radish, silk moth, wolf spider, frog, preferably in *Xenopus laevis*, *Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

In another preferred embodiment the antimicrobial peptide of the fusion protein consists of about 0% to about 5%, or about 0% to about 35%, or about 10% to about 35% or about 15% to about 45%, or about 20% to about 45% positively charged amino acid residues, in particular lysine and/or arginine residues and of about 50% to about 80%, or about 60% to about 80%, or about 55% to about 75%, or about 70% to about 90% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues.

In another preferred embodiment of the present invention the antimicrobial peptide of the fusion protein consists of about 4% to about 58% positively charged amino acid residues, in particular lysine and/or arginine residues and of about 33% to about 89% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. Examples for antimicrobial peptides of the fusion protein according to the present invention are listed in the following table.

TABLE 3

| Peptide | Amino acid sequence | SEQ ID NO |
|---|---|---|
| LL-37 | LLGDFFRKSKEKIGKEFKRIVQRIKDFLRNLVPRTES | SEQ ID NO: 93 |
| SMAP-29 | RGLRRLGRKIAHGVKKYGPTVLRIIRIAG | SEQ ID NO: 94 |
| Indolicidin | ILPWKWPWWPWRR | SEQ ID NO: 95 |
| Protegrin | RGGRLCYCRRRFCVCVGR | SEQ ID NO: 96 |
| Cecropin P1 | SWLSKTAKKLENSAKKRISEGIAIAIQGGPR | SEQ ID NO: 97 |
| Magainin | GIGKFLHSAKKFGKAFVGEIMNS | SEQ ID NO: 98 |
| Pleurocidin | GWGSFFKKAAHVGKHVGKAALTHYL | SEQ ID NO: 99 |
| Cecropin A (A. aegypti) | GGLKKLGKKLEGAGKRVFNAAEKALPVVAGAKALRK | SEQ ID NO: 100 |

TABLE 3-continued

| Peptide | Amino acid sequence | SEQ ID NO |
|---|---|---|
| Cecropin A (*D. melanogaster*) | GWLKKIGKKIERVGQHTRDATIQGLGIPQQAANVAATARG | SEQ ID NO: 101 |
| Buforin II | TRSSRAGLQFPVGRVHRLLRK | SEQ ID NO: 102 |
| Sarcotoxin IA | GWLKKIGKKIERVGQHTRDATIQGLGIAQQAANVAATAR | SEQ ID NO: 103 |
| Apidaecin | ANRPVYIPPPRPPHPRL | SEQ ID NO: 104 |
| Ascaphine 5 | GIKDWIKGAAKKLIKTVASHIANQ | SEQ ID NO: 105 |
| Nigrocine 2 | GLLSKVLGVGKKVLCGVSGLVC | SEQ ID NO: 106 |
| Pseudin 1 | GLNTLKKVFQGLHEAIKLINNHVQ | SEQ ID NO: 107 |
| Ranalexin | FLGGLIVPAMICAVTKKC | SEQ ID NO: 108 |
| Melittin | GIGAVLKVLTTGLPALISWIKRKRQQ | SEQ ID NO: 109 |
| Lycotoxin 1 | IWLTALKFLGKHAAKKLAKQQLSKL | SEQ ID NO: 110 |
| Parasin 1 | KGRGKQGGKVRAKAKTRSS | SEQ ID NO: 111 |
| Buforin I | AGRGKQGGKVRAKAKTRSSRAGLQFPVGRVHRLLRKGNY | SEQ ID NO: 112 |
| Dermaseptin 1 | ALWKTMLKKLGTMALHAGKAALGAAADTISQGTQ | SEQ ID NO: 113 |
| Bactenecin 1 | RLCRIVVIRVCR | SEQ ID NO: 114 |
| Thanatin | GSKKPVPIIYCNRRTGKCQRM | SEQ ID NO: 115 |
| Brevinin 1T | VNPIILGVLPKVCLITKKC | SEQ ID NO: 116 |
| Ranateurin 1 | SMLSVLKNLGKVGLGFVACKINIKQC | SEQ ID NO: 117 |
| Esculentin 1 | GIFSKLGRKKIKNLLISGLKNVGKEVGMDVVRTGIKIAGCKIKGEC | SEQ ID NO: 118 |
| Tachyplesin | RWCFRVCYRGICYRKCR | SEQ ID NO: 119 |
| Androctonin | RSVCRQIKICRRRGGCYYKCTNRPY | SEQ ID NO: 120 |
| alpha-defensin | DCYCRIPACIAGERRYGTCIYQGRLWAFCC | SEQ ID NO: 121 |
| beta-defensin | NPVSCVRNKGICVPIRCPGSMKQIGTCVGRAVKCCRKK | SEQ ID NO: 122 |
| theta-defensin | GFCRCLCRRGVCRCICTR | SEQ ID NO: 123 |
| defensin (sapecin A) | ATCDLLSGTGINHSACAAHCLLRGNRGGYCNGKAVCVCRN | SEQ ID NO: 124 |
| Thionin (crambin) | TTCCPSIVARSNFNVCRIPGTPEAICATYTGCIIIPGATCPGDYAN | SEQ ID NO: 125 |
| defensin from radish | QKLCQRPSGTWSGVCGNNNACKNQCIRLEKARHGSCNYVFPAHCICYFPC | SEQ ID NO: 126 |
| Drosomycin | DCLSGRYKGPCAVWDNETCRRVCKEEGRSSGHCSPSLKCWCEGC | SEQ ID NO: 127 |
| Hepcidin | DTHFPICIFCCGCCHRSKCGMCCKT | SEQ ID NO: 128 |
| Bac 5 | RFRPPIRRPPIRPPFYPPFRPPIRPPIFPPIRPPFRPPLGRPFP | SEQ ID NO: 129 |
| PR 39 | RRRPRPPYLPRPRPPPFFPPRLPPRIPPGFPPRFPPRFP | SEQ ID NO: 130 |
| Pyrrhocoricin | VDKGSYLPRPTPPRPIYNRN | SEQ ID NO: 131 |
| Histatin 5 | DSHAKRHHGYKRKFHEKHHSHRGY | SEQ ID NO: 132 |

In a further embodiment of the present invention the peptide is a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 133.

Preferred sushi peptides of the fusion protein are sushi peptides Sib 1 and Sib 3 and multiples thereof; FASEB J. 2000 September ; 14(12):1801-13.

In a further embodiment of the present invention the peptide is a hydrophobic peptide, which comprises at least 90% of the hydrophobic amino acid residues of valine, isoleucine, leucine, methionine, phenylalanine, tryptophan, cysteine, alanine, tyrosine, histidine, threonin, serine, proline and/or glycine. In another preferred embodiment the hydrophobic peptide of the fusion protein consist of about 90% to about 95%, or of about 90 to about 100%, or of about 95% to about 100% of the hydrophobic amino acid residues of valine, isoleucine, leucine, methionine, phenylalanine, tryptophan, cysteine, alanine, tyrosine, histidine, threonin, serine, proline and/or glycine.

Preferred hydrophobic peptides of the fusion protein are Walmagh1 having the amino acid sequence according to SEQ ID NO: 134 and the hydrophobic peptide of the fusion protein having the amino acid sequence Phe-Phe-Val-Ala-Pro (SEQ ID NO: 135).

In a further embodiment of the present invention the peptide is an amphiphatic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, histidine, threonin, serine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphiphatic peptide is fused at the N-terminal and/or the C-terminal end of the enzyme having cell wall degrading activity, thus enhancing the amphiphaticity of the latter proteins.

In another embodiment of the present invention the peptide is an amphiphatic peptide consisting of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. In a preferred embodiment at least about 30, 40, 50, 60 or 70% of the said amino acid residues of the amphiphatic peptide are either arginine or lysine residues and/or at least about 30, 40, 50, 60 or 70% of the said amino acid residues of the amphiphatic peptide are of the hydrophobic amino acids valine, isoleucine, leucine, methionine, phenylalanine, tryptophan, cysteine, alanine, tyrosine, histidine, threonin, serine, proline and/or glycine.

In another preferred embodiment of the present invention the peptide is an amphiphatic peptide comprising beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. Preferred are amphiphatic peptides consisting of about 10% to about 50%, or about 20% to about 50%, or about 30% to about 45% or about 5% to about 30% positively charged amino acid residues, in particular lysine and/or arginine residues and of about 50% to about 85%, or about 50% to about 90%, or about 55% to about 90%, or about 60% to about 90%, or about 65% to about 90% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. In another preferred embodiment amphiphatic peptides consisting of 12% to about 50% positively charged amino acid residues, in particular lysine and/or arginine residues and of about 50% to about 85% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues.

Preferred amphiphatic peptides of the fusion protein are, α4-helix of T4 lysozyme according to SEQ ID NO: 136 and WLBU2-Variant having the amino acid sequence according to SEQ ID NO: 137 and Walmagh 2 according to SEQ ID NO: 138.

In a preferred embodiment of the present invention the fusion protein consists of a peptide according to SEQ ID NO: 10 to 30, 32 to 34 and 93 to 138 and an endolysin according to SEQ ID NO: 1 to 9, 84 to 86 and 88 to 92 or a bacteriocin according to SEQ ID NO: 87. In a preferred embodiment the fusion protein comprises a peptide selected from the group of peptides according to SEQ ID NO: 10 to 30, 32 to 34 and 93 to 138 and an endolysin selected from the group of endolysins according to SEQ ID NO: 1 to 9, 84 to 86 and 88 to 92 or a bacteriocin according to SEQ ID NO: 87.

Especially preferred are fusion proteins selected from the group consisting of the following fusion proteins presented in the Table 4.

TABLE 4

| Fusion protein | SEQ ID NO: (fusion protein) | Endolysin/Bacteriocin part | Peptide (N-terminal unless otherwise indicated) |
|---|---|---|---|
| POLY-gp144 | SEQ ID NO: 35 | SEQ ID NO: 1 | SEQ ID NO: 11 |
| (POLY)$^2$-gp144 | SEQ ID NO: 36 | SEQ ID NO: 1 | SEQ ID NO: 21 |
| (POLY)$^3$-gp144 | SEQ ID NO: 37 | SEQ ID NO: 1 | SEQ ID NO: 27 |
| (POLY)$^4$-gp144 | SEQ ID NO: 38 | SEQ ID NO: 1 | SEQ ID NO: 30 |
| POLY-gp188 | SEQ ID NO: 39 | SEQ ID NO: 2 | SEQ ID NO: 11 |

TABLE 4-continued

| Fusion protein | SEQ ID NO: (fusion protein) | Endolysin/Bacteriocin part | Peptide (N-terminal unless otherwise indicated) |
|---|---|---|---|
| (POLY)²-gp188 | SEQ ID NO: 40 | SEQ ID NO: 2 | SEQ ID NO: 21 |
| (POLY)³-gp188 | SEQ ID NO: 41 | SEQ ID NO: 2 | SEQ ID NO: 27 |
| (POLY)⁴-gp188 | SEQ ID NO: 42 | SEQ ID NO: 2 | SEQ ID NO: 30 |
| pKKZ144pET32b | SEQ ID NO: 43 | SEQ ID NO: 1 | SEQ ID NO: 14 |
| KRK_6_pET32b | SEQ ID NO: 44 | SEQ ID NO: 1 | SEQ ID NO: 10 |
| KRK_12_pET32b | SEQ ID NO: 45 | SEQ ID NO: 1 | SEQ ID NO: 15 |
| KRK_14_pET32b | SEQ ID NO: 46 | SEQ ID NO: 1 | SEQ ID NO: 16 |
| R9_pET32b | SEQ ID NO: 47 | SEQ ID NO: 1 | SEQ ID NO: 12 |
| K8_pET32b | SEQ ID NO: 48 | SEQ ID NO: 1 | SEQ ID NO: 13 |
| pK2KZ144_pET32b_mod3 | SEQ ID NO: 49 | SEQ ID NO: 1 | SEQ ID NO: 28 |
| PKPSP3gp10 | SEQ ID NO: 53 | SEQ ID NO: 8 | SEQ ID NO: 11 |
| PKP2gp09 | SEQ ID NO: 57 | SEQ ID NO: 9 | SEQ ID NO: 11 |
| PKOBPgpLYS | SEQ ID NO: 61 | SEQ ID NO: 7 | SEQ ID NO: 11 |
| pK2KZ144pET32b | SEQ ID NO: 62 | SEQ ID NO: 1 | SEQ ID NO: 22 |
| pK3KZ144pET32b | SEQ ID NO: 63 | SEQ ID NO: 1 | SEQ ID NO: 27 |
| pK4KZ144pET32b | SEQ ID NO: 64 | SEQ ID NO: 1 | SEQ ID NO: 30 |
| KRK_19_pET32b | SEQ ID NO: 66 | SEQ ID NO: 1 | SEQ ID NO: 18 |
| KRK_21_pET32b | SEQ ID NO: 67 | SEQ ID NO: 1 | SEQ ID NO: 23 |
| KRK_25_pET32b | SEQ ID NO: 68 | SEQ ID NO: 1 | SEQ ID NO: 26 |
| KRK_39_pET32b | SEQ ID NO: 69 | SEQ ID NO: 1 | SEQ ID NO: 29 |
| K19_pET32b | SEQ ID NO: 70 | SEQ ID NO: 1 | SEQ ID NO: 20 |
| K16_pET32b | SEQ ID NO: 71 | SEQ ID NO: 1 | SEQ ID NO: 17 |
| pKKZ-144_K2_pET32b | SEQ ID NO: 72 | SEQ ID NO: 1 | N-terminal: SEQ ID NO: 11 C-terminal: SEQ ID NO: 21 |
| pK2KZ144_pET32b_mod1 | SEQ ID NO: 73 | SEQ ID NO: 1 | SEQ ID NO: 24 |
| pK2KZ144_pET32b_mod2 | SEQ ID NO: 74 | SEQ ID NO: 1 | SEQ ID NO: 25 |
| smi01_KRK9 | SEQ ID NO: 75 | SEQ ID NO: 5 | SEQ ID NO: 11 |
| smi02_KRK9 | SEQ ID NO: 76 | SEQ ID NO: 4 | SEQ ID NO: 11 |
| smi03_KRK9 | SEQ ID NO: 77 | SEQ ID NO: 6 | SEQ ID NO: 11 |
| smi04_KRK9 | SEQ ID NO: 78 | SEQ ID NO: 3 | SEQ ID NO: 11 |
| SMAP-29-KZ144 | SEQ ID NO: 139 | SEQ ID NO: 1 | SEQ ID NO: 94 |
| Ply2638-PK | SEQ ID NO: 140 | SEQ ID NO: 92 | SEQ ID NO: 11 |
| Pentapeptid-Ply511 | SEQ ID NO: 141 | SEQ ID NO: 85 | SEQ ID NO: 135 |
| PK-Lysostaphin | SEQ ID NO: 142 | SEQ ID NO: 87 | SEQ ID NO: 11 |

The fusion proteins according to the present invention, and thus in particular the especially preferred fusion proteins according to SEQ ID NO: 35 to 49, 53, 57, 61 to 64, 66 to 78 and 139 to 142 may additional comprise a methionine on the N-terminus.

The fusion proteins according to the present invention, and thus in particular the especially preferred fusion proteins according to SEQ ID NO: 35 to 49, 53, 57, 61 to 64, 66 to 78 and 139 to 142 may additional comprise a tag e.g. for purification. Preferred is a $His_6$-tag, preferably at the C-terminus of the fusion protein. Said tag can be linked to the fusion protein by additional amino acid residues e.g. due to cloning reasons. Preferably said tag can be linked to the fusion protein by at least 1, 2, 3, 4, 5, 6, 7, 8, 9 or 10 additional amino acid residues. In a preferred embodiment the fusion protein comprises a $His_6$-tag at its C-terminus linked to the fusion protein by the additional amino acid residues lysine and glycine (Lys-Gly) or leucine and glutamic acid (Leu-Glu). Preferably, said additional amino acid residues may be not recognized or cleaved by proteases. In another preferred embodiment the fusion protein comprises a $His_6$-tag at its N-terminus linked to the fusion protein by the additional amino acid residues lysine and glycine (Lys-Gly) or leucine and glutamic acid (Leu-Glu). In another preferred embodiment the fusion protein comprises a $His_6$-tag at its N- and C-terminus linked to the enzyme, preferably to the endolysin, autolysin or bacteriocin by the additional amino acid residues lysine and glycine (Lys-Gly) or leucine and glutamic acid (Leu-Glu).

In particular, the fusion proteins as used in the examples as described below are preferred. The fusion proteins according to SEQ ID NO: 35 to 42, 53, 57 and 61 as used in the examples comprise a $His_6$-tag at the C-terminus linked to the fusion protein by the additional amino acid residues lysine and glycine (Lys-Gly). The fusion protein according to SEQ ID NO: 43 to 49, 75, 139, 141 and 142 as used in the examples comprise a $His_6$-tag at the C-terminus linked to the respective fusion protein by the additional amino acid residues leucine and glutamic acid (Leu-Glu).

Fusion proteins are constructed by linking at least two nucleic acid sequences using standard cloning techniques as described e.g. by Sambrook et al. 2001, Molecular Cloning: A Laboratory Manual. Such a protein may be produced, e.g., in recombinant DNA expression systems. Such fusion proteins according to the present invention can be obtained by fusing the nucleic acids for endolysin, autolysin or bacteriocin and the respective peptide.

As some fusion proteins may either be toxic upon expression in bacteria, or not homogenous due to protein degradation, the strategy might be to express these fusion proteins fused or linked to other additional proteins. Example for these other additional protein is Thioredoxin, which was shown to mediate expression of toxic antimicrobial peptides in *E. coli* (TrxA mediating fusion expression of antimicrobial peptide CM4 from multiple joined genes in *Escherichia coli*. Zhou L, Zhao Z, Li B, Cai Y, Zhang S. Protein Expr Purif. 2009 April; 64(2):225-230).

For antimicrobial function of the fusion proteins it may be necessary to remove the additional fusion protein by proteolytic cleavage. Commercially available kits like the pET32 expression system (Novagen), may need to modify e.g. the N-terminus of the fusion depending on the protease used, like from MGS to AMGS (SEQ ID NO: 31), were the remaining alanine residue results from an introduced Enterokinase cleavage site.

In another preferred embodiment of the present invention the peptides of the fusion proteins according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, PEGylation, chemical changes of the amino-, SH- or carboxyl-groups.

The present invention further relates to methods of eliminating, reducing or preventing bacterial biofilms by means of an isolated nucleic acid molecule encoding the fusion protein according to the present invention. The present invention further relates to a vector comprising the nucleic acid molecule according to the present invention. Said vector may provide for the constitutive or inducible expression of said fusion protein according to the present invention.

The fusion proteins may be obtained from a microorganism, such as a genetically modified suitable host cell which expresses said fusion proteins. Said host cell may be a micro-organism such as bacteria or yeast or fungi or an animal cell as e.g. a mammalian cell, in particular a human cell. In one embodiment of the present invention the yeast cell is a *Pichia pastoris* cell. The host may be selected due to mere biotechnological reasons, e.g. yield, solubility, costs, etc. but may be also selected from a medical point of view, e.g. a non-pathological bacteria or yeast, human cells.

In a further aspect the present invention relates to methods of eliminating, reducing or preventing bacterial biofilms by means of a composition, preferably a pharmaceutical composition, comprising a fusion protein according to the present invention and/or a host transformed with a nucleic acid molecule or a vector comprising a nucleotide sequence encoding a fusion protein according to the present invention.

In a preferred embodiment of the present invention the methods of eliminating, reducing or preventing bacterial biofilms by means of the composition comprises additionally agents permeabilizing the outer membrane of Gram-negative bacteria such metal chelators as e.g. EDTA, TRIS, lactic acid, lactoferrin, polymyxin, citric acid and/or other substances as described e.g. by Vaara (Agents that increase the permeability of the outer membrane. Vaara M. Microbiol Rev. 1992 September; 56(3):395-441). Also preferred are compositions comprising combinations of the above mentioned permeabilizing agents. Especially preferred is a composition comprising about 10 µM to about 100 mM EDTA, more preferably about 50 µM to about 10 mM EDTA, more preferably about 0.5 mM to about 10 mM EDTA, more preferably about 0.5 mM to about 2 mM EDTA, more preferably about 0.5 mM to 1 mM EDTA. However, also compositions comprising about 10 µM to about 0.5 mM EDTA are preferred. Also preferred is a composition comprising about 0.5 mM to about 2 mM EDTA, more preferably about 1 mM EDTA and additionally about 10 to about 100 mM TRIS.

The present invention also relates to methods of eliminating, reducing or preventing bacterial biofilms by means of a fusion protein according to the present invention and/or a host transformed with a nucleic acid comprising a nucleotide sequence encoding a fusion protein according to the present invention for use as a medicament.

In a further aspect the present invention relates to the use of a fusion protein according to the present invention and/or a host transformed with a vector comprising a nucleic acid molecule comprising a nucleotide sequence encoding a fusion protein according to the present invention for eliminating, reducing and preventing bacterial biofilms. Preferred is the use wherein the bacteria generating the biofilm cause a disorder, disease or condition detrimental to plants, animals and/or human beings. Preferred is the use wherein the bacteria generating the biofilm may be Gram-negative bacteria of bacterial groups, families, genera or species comprising strains pathogenic for humans or animals like Enterobacteriaceae (Escherichia, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella, Spirochaetaceae* (*Treponema* and *Borrelia*), Leptospiraceae, *Campylobacter, Helicobacter, Spirillum, Streptobacillus, Bacteroidaceae* (*Bacteroides, Fusobacterium, Prevotella, Porphyromonas*), *Acinetobacter*, especially *A. baumannii*. Preferably, said disorder, disease or condition may be caused by *Pseudomonas*, in particular *Pseudomonas aeruginosa* and/or *Pseudomonas putida, Burkholderia*, in particular *Burkholderia pseudomallei* and/or *Burkholderia solanacearum, Salmonella*, in particular *Salmonella typhimurium* and/or *Salmonella Enteritidis*, *Acinetobacter*, in particular *Acinetobacter baumannii, Escherichia coli* and/or *Klebsiella*, in particular *Klebsiella pneumoniae*. In particular the treatment and/or prevention of the disorder, disease or condition may be caused by Gram-positive bacteria of bacterial groups, families, genera or species comprising strains pathogenic for humans or animals like *Listeria monocytogenes, Staphylococcus aureus, Enterococcus faecalis, Enterococcus faecium, Streptococcus pneumoniae, Streptococcus pyogenes, Streptococcus mutans, Streptococcus equi, Clostridium difficile, Clostridium botulinum, Clostridium tetani, Clostridium perfringens, Bacillus anthracis, Bacillus cereus, Propionibacterium acnes, Mycobacterium avium, Mycobacterium tuberculosis, Corynebacterium diphteriae, Mycoplasma pneumoniae, Actinomyces*.

In a preferred embodiment, the fusion protein, preferably the endolysin variant, autolysin variant or bacteriocin variant In a further aspect the present invention relates to a method of treating a disorder, disease or condition associated with bacterial biofilm in a subject in need of treatment and/or prevention, which method comprises administering to said subject an effective amount of a fusion protein according to the present invention and/or an effective amount of a host transformed with a nucleic acid comprising a nucleotide sequence encoding a fusion protein according to the present invention or a composition according to the present invention. The subject may be a human or an animal.

Preferably said method of treatment may be for the treatment and/or prevention of infections caused by Gram-negative and/or Gram-positive bacteria associated with bacterial biofilm, in particular by the Gram-negative and Gram-positive bacteria as listed above. In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-negative and/or Gram-positive bacteria associated with bacterial biofilm, in particular by the Gram-negative and Gram-positive bacteria as listed above.

The dosage and route of administration used in a method of treatment or prophylaxis according to the present invention depends on the specific disease/site of infection to be treated. The route of administration may be for example oral, topical, nasopharyngeal, parenteral, inhalational, intravenous, intramuscular, intrathecal, intraspinal, endobronchial, intrapulmonal, intraosseous, intracardial, intraarticular, rectal, vaginal or any other route of administration. In a preferred embodiment the fusion protein is applied topical to the biological material, preferably the skin, in particular of mammals, preferably of human. In a preferred embodiment the fusion protein is applied systemic to the biological material, preferably the blood, in particular of mammals, preferably of human.

For application of a fusion protein according to the present invention and/or an effective amount of a host transformed with a nucleic acid comprising a nucleotide sequence encoding a fusion protein according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, powder, suppository, emulsion, suspension, gel, lotion, cream, salve, injectable solution, syrup, spray, inhalant or any other medical reasonable galenic formulation. Preferably, the galenic formulation may comprise suitable carriers, stabilizers, flavourings, buffers or other suitable reagents. For example, for topical application the formulation may be a lotion, cream, gel, salve or plaster, for nasopharyngeal application the formulation may be saline solution to be applied via a spray to the nose. For oral administration in case of the treatment and/or prevention of a specific infection site e.g. in the intestine, it can be necessary to protect a fusion protein according to the present invention from the harsh digestive environment of the gastrointestinal tract until the site of infection is reached. Thus, bacteria as carrier, which survive the initial steps of digestion in the stomach and which secret later on a fusion protein according to the present invention into the intestinal environment can be used.

In a specific embodiment the present invention relates to the use of a fusion protein according to the present invention and/or a host transformed with a vector comprising a nucleic acid molecule comprising a nucleotide sequence encoding a fusion protein according to the present invention in the manufacture of a medicament for the treatment and/or prevention of a disorder, disease or condition caused by Gram-negative and/or Gram-positive bacterial infections associated with bacterial biofilm. A preferred embodiment relates to the use of a fusion protein according to the present invention in the manufacture of a medicament for the treatment and/or prevention of a disorder, disease or condition caused by Gram-negative and/or Gram-positive bacterial infections associated with bacterial biofilm in combination or addition to antibiotics.

In a specific embodiment the present invention relates to the use of a fusion protein according to the present invention and/or a host transformed with a vector comprising a nucleic acid molecule comprising a nucleotide sequence encoding a fusion protein according to the present invention in the manufacture of a medicament for the treatment and/or prevention of a disorder, disease or condition caused by *Pseudomonas* associated with bacterial biofilm, particularly by *Pseudomonas aeruginosa* in particular intestinal affections, in particular in infants, infections of the meninges, e.g. meningitis haemorrhagica, infections of the middle ear, the skin (*Eethyma gangraenosum*), in particular burns, the urinary tract, rhinitis, bacteremic pneumonia, in particular wherein the patient is suffering from cystic fibrosis or hematologic malignancies such as leukemia, or with neutropenia from immunosuppressive therapy, septicemia, in particular because of long-term intravenous or urinary catheterization, invasive surgical procedures and severe burns, endocarditis, in particular wherein the patient is a intravenous drug user or a patient with complications from open heart surgery, highly destructive ocular infections, in particular after the use of contaminated ophthalmologic solutions or severe facial burns, osteochondritis, in particular as a result of severe trauma or puncture wounds through contaminated clothing.

In another specific embodiment of the present invention the disorder, disease or condition is caused by *Burkholderia pseudomallei* associated with bacterial biofilm, in particular Whitmore's Disease, chronic pneumonia, septicemia, in particular wherein the patient has a traumatized skin lesion. In another specific embodiment of the present invention the disorder, disease or condition is caused by *Salmonella thyphimurium* and *Salmonella enteritidis* associated with bacterial biofilm, in particular acute gastroenteritis and local purulent processes, particularly osteomyelitis, endocarditis, cholecystitis and especially caused by *Salmonella thyphimurium* meningitis, in particular wherein the patient is less than two years old. In another specific embodiment of the present invention the disorder, disease or condition is caused by *Salmonella typhi*, in particular typus. In another specific embodiment of the present invention the disorder, disease or condition is caused by *Salmonell paratyphi*, in particular paratyphus. In another specific embodiment of the present invention the disorder, disease or condition is caused by *Acinetobacter baumannii* associated with bacterial biofilm, in particular bronchitis, pneumonia, wound infections and septicemia, in particular as a result of intravenous catheterization. In another specific embodiment of the present invention the disorder, disease or condition is caused by *Escherichia coli* associated with bacterial biofilm, in particular extra intestinal infections, particularly appendicitis, purulent cholecystitis, peritonitis, purulent meningitis and infection of the urinary tract, intraintestinal *E. coli* infections, particularly epidemic enteritis, and infectious disease similar to dysentery, septicemia, enterotoxemia, mastitis and dysentery. In another specific embodiment of the present invention the disorder, disease or condition is caused by *Klebsiella pneumoniae* associated with bacterial biofilm, in particular pneumonia, bacteremia, meningitis and infections of the urinary tract. In a specific embodiment the present invention relates to the use of a fusion protein according to the present invention and/or a host transformed with a vector comprising a nucleic acid molecule comprising a nucleotide sequence encoding a fusion protein according to the present invention in the manufacture of a medicament for the treatment and/or prevention of a disorder, disease or condition caused by *Listeria monocytogenes*, in particular Granulomatosis infantiseptica (listeriosis of newborns), mononucleosis, conjunctivitis, meningitis, granulomatosis septica and the listeriosis of pregnant women. In another specific embodiment of the present invention the disorder, disease or condition is caused by *Staphylococcus aureus*, in particular infections of the skin like pyoderma, particularly folliculitis, furuncle, carbuncle, abscesses of the sweat glands and pemphigus, and like scaled skin syndrome. The scaled skin syndrome can appear in three clinical pictures: dermatitis exfoliativa, impetigo bullosa and scarlatiniform erythroderma. Moreover the disorder, disease or condition caused by *Staphylococcus aureus* is *Staphylococcus* pneumonia, hospitalism, in particular surgical wound infections, mastitis puerperalis and enterokolitis, and food poisonings. In another specific embodiment of the present invention the disorder, disease or condition is caused by *Streptococcus pyogenes*, in particular tonsillitis, pharyngitis, scarlet, erysipelas, rheumatic fever and acute glomerulonephritis. In another specific embodiment of the present invention the disorder, disease or condition is caused by *Streptococcus pneumoniae*, in particular pneumonia, ulcus serpens corneae, otitis media, meningitis, peritonitis, mastoiditis and osteomyelitis.

In another specific embodiment of the present invention the disorder, disease or condition is caused by *Clostridium perfringens*, in particular gas gangrene, enteritis necroticans ulcerosa and food poisonings. In another specific embodiment of the present invention the disorder, disease or condition is caused by *Clostridium botulinum*, in particular botulism. In another specific embodiment of the present invention the disorder, disease or condition is caused by *Clostridium difficile*, in particular pseudomembranoes enterokolitis. In another specific embodiment of the present invention the disorder, disease or condition is caused by *Bacillus anthracis*, in particular cutaneous anthrax, inhalation anthrax, and gastrointestinal anthrax. In another specific embodiment of the present invention the disorder, disease or condition is caused by *Enterococcus faecalis* or *E. faecium*, like nosocomial infections, and endokarditis. In another specific embodiment of the present invention the disorder, disease or condition is caused by *Bacillus cereus*, in particular food poisonings, bronchial pneumonia, septicaemia and meningitis. In another specific embodiment of the present invention the disorder, disease or condition is caused by *Mycobacterium avium, Mycobacterium paratuberculosis* and *Mycobacterium tuberculosis*, in particular tuberculosis. In another specific embodiment of the present invention the disorder, disease or condition is caused by *Mycoplasma pneumoniae*, in particular pneumonia, diseases of the upper respiratory tract and inflammations of the ear drum. In another specific embodiment of the present invention the disorder, disease or condition is caused by *Actinomyces*, in particular actinomycosis in human, cattle, cat and dog. In another specific embodiment of the present invention the disorder, disease or condition is caused by *Corynebacterium diphteriae*, in particular localized diphtheria of the tonsils, the nose, the nasopharynx or the middle ear, progressive diphtheria of the larynx, the trachea and the bronchi, toxic or maligne diphtheria, skin and wound diphtheria.

The methods of eliminating, reducing or preventing bacterial biofilms by means of fusion proteins according to the present invention provide a possibility to invade into the bacterial biofilm and eliminate, reduce and prevent the bacterial biofilm.

The methods of eliminating, reducing or preventing bacterial biofilms by means of fusion proteins according to the present invention may be for the treatment and/or prevention of the following infections: wound infections, in particular wounds associated with diabetes mellitus, tonsillitis, osteomyelitis, bacterial endocarditis, sinusitis, infections of the cornea, urinary tract infection, infection of the biliary tract, infectious kidney stones, urethritis, prostatitis, catheter infections, middle-ear infections, formation of dental plaque, gingivitis, periodontitis, cystic fibrosis, and infections of permanent indwelling devices such as joint prostheses and heart valves.

In another preferred embodiment of eliminating, reducing and preventing bacterial biofilms by means of fusion proteins according to the present invention may be for the treatment and/or prevention of infections associated with foreign matter, like contamination and colonisation of catheters, implants and medical devices, in particular instruments, apparatus, endoscopes, dental devices, dialysis equipment, like peritoneal dialysis catheter, pacemaker, endotracheal tubes, voice prothesis, cerebrospinal fluid shunts, venous catheter, artificial heart valves and joint prothesis.

In another preferred embodiment of eliminating, reducing and preventing bacterial biofilms by means of fusion proteins according to the present invention the bacterial biofilm is formed by *Staphylococcus epidermidis, Staphylococcus aureus, Pseudomonas aeruginosa, Escherichia coli* and *Candida albicans*.

In another preferred embodiment of eliminating, reducing and preventing bacterial biofilms by means of fusion proteins according to the present invention may be for the prevention or removal of contaminations in health care, agriculture, and industrial settings, in particular in water pipes of hospitals, in water, plumbing, ventilation, building heating, air conditioning, oil wells, cosmetics and medicaments.

In another preferred embodiment of eliminating, reducing and preventing bacterial biofilms by means of fusion proteins according to the present invention may be for the prevention of biocorrision, in particular in cooling circuits, water treatment plants, domestic hot water systems, power plants, production systems and machineries for automobiles, computers, colours, oil and gas.

In another preferred embodiment of eliminating, reducing and preventing bacterial biofilms by means of fusion proteins according to the present invention may be for the prevention of biofouling, in particular on submarine objects, ships, platforms, buoys, sensor systems for scientific or surveillance purposes in the maritime field.

In a preferred embodiment of the present invention a fusion protein according to the present invention is used for medical treatment, if the infection to be treated or prevented is caused by multiresistant bacterial strains associated with bacterial biofilm, in particular by strains resistant against one or more of the following antibiotics: streptomycin, tetracycline, cephalothin, gentamicin, cefotaxime, cephalosporin, ceftazidime or imipenem.

Furthermore, in the methods or the use of the present invention the fusion protein, preferably the endolysin variant, the autolysin variant or bacteriocin variant can be used, added or administered in combination or in addition with conventional antibacterial agents, such as antibiotics, lantibiotics, bacteriocins or endolysins. In another preferred embodiment, the antibiotics are added, used or administered in the methods and the use according to the present invention simoultaneous with the fusion protein, after or before the administration or addition of fusion protein.

In a preferred embodiment of the present invention the fusion protein can be used or administered in combination with at least one of the following antibiotics: β-lactams, aminoglycosides, fluoroquinolones, macrolides, novobiocin, rifampicin, oxazolidinones, fusidic acid, mupirocin, pleuromutilins, daptomycin, vancomycin, tetracyclines, sulfonamides, chloramphenicol, trimetoprim, fosfomycin, cycloserine and polymyxin.

In another preferred embodiment of the present invention the fusion protein can be used in methods of eliminating, reducing or preventing bacterial biofilms of *Staphylococcus aureus* by administering it in combination with at least one of the following antibiotics: β-lactams, aminoglycosides, fluoroquinolones, macrolides, novobiocin, rifampicin, oxazolidinones, fusidic acid, mupirocin, pleuromutilins, daptomycin, vancomycin, tetracyclines, sulfonamides, chloramphenicol, trimetoprim, fosfomycin and cycloserine.

In another preferred embodiment of the present invention a fusion protein can be used in methods of eliminating, reducing or preventing bacterial biofilms of *Escherichia coli* by administering it in combination with at least one of the following antibiotics: β-lactams, aminoglycosides, fluoroquinolones, tetracyclines, sulfonamides, chloramphenicol, trimetoprim, fosfomycin, cycloserine and polymyxin.

In another preferred embodiment of the present invention a fusion protein can be used in methods of eliminating, reducing or preventing bacterial biofilms of *Pseudomonas aeruginosa* by administering it in combination with at least one of the following antibiotics: β-lactams, aminoglycosides, fluoroquinolones and polymyxin.

The present invention also relates to a pharmaceutical pack for use of eliminating, reducing and preventing bacterial biofilm comprising one or more compartments, wherein at least one compartment comprises one or more fusion protein according to the present invention and/or one or more hosts transformed with a nucleic acid comprising a nucleotide sequence encoding a fusion protein according to the present invention or a composition according to the present invention.

In another aspect the present invention relates to a process of preparation of a pharmaceutical composition for use of eliminating, reducing and preventing bacterial biofilm, said process comprising admixing one or more fusion protein according to the present invention and/or one or more hosts transformed with a nucleic acid comprising a nucleotide sequence encoding a fusion protein according to the present invention with a pharmaceutically acceptable diluent, excipient or carrier.

In an even further aspect the composition according to the present invention is a cosmetic composition for use of eliminating, reducing and preventing bacterial biofilm. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the fusion protein according to the present invention in order to degrade already existing or freshly settling pathogenic Gram-negative and/or Gram-positive bacteria.

In a further aspect the present invention relates to the fusion protein according to the present invention for use as diagnostic means in medicinal, food or feed or environmental diagnostics, in particular as a diagnostic means for the diagnostic of bacteria infection caused in particular by Gram-negative and/or Gram-positive bacteria associated with bacterial biofilm. In this respect the fusion protein according to the present invention may be used as a tool to specifically degrade pathogenic bacteria associated with bacterial biofilm, in particular Gram-negative and/or Gram-positive pathogenic bacteria. The degradation of the bacterial cells by the fusion protein according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the fusion protein according to the present invention for the removal, reduction and/or prevention of Gram-negative and/or Gram-positive bacterial contamination associated with bacterial biofilm of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a fusion protein of the present invention may be used in methods of eliminating, reducing or preventing bacterial biofilms prophylactically as sanitizing agent. Said sanitizing agent may be used before or after surgery, or for example during hemodialysis. Moreover, premature infants and immunocompromised persons, or those subjects with need for prosthetic devices may be treated with a fusion protein according to the present invention. Said treatment may be either prophylactically or during acute infection. In the same context, nosocomial infections, especially by antibiotic resistant strains like Pseudomonas aeruginosa (FQRP), Acinetobacter species and Enterobacteriaceae such as E. coli, Salmonella, Shigella, Citrobacter, Edwardsiella, Enterobacter, Hafnia, Klebsiella, Morganella, Proteus, Providencia, Serratia and Yersinia species; Methicillin-resistant Staphylococcus aureus, Vancomycin-resistant Enterococcus faecalis, Vancomycin-resistant Enterococcus faecium, Streptococcus pneumoniae, Propionibacterium acnes, multidrug-resistant Mycobacterium tuberculosis, may be treated prophylactically or during acute phase with a fusion protein of the present invention. Therefore, a fusion protein according to the present invention may be used as a disinfectant to eliminate, reduce and prevent bacterial biofilms also in combination with other ingredients useful in a disinfecting solution like detergents, tensids, solvents, antibiotics, lantibiotics, or bacteriocins.

For the use of the fusion protein according to the present invention for eliminating, reducing or preventing bacterial biofilms as a disinfectant e.g. in hospital, dental surgery, veterinary, kitchen or bathroom, the fusion protein can be prepared in a composition in form of e.g. a fluid, a powder, a gel, or an ingredient of a wet wipe or a disinfection sheet product. Said composition may additionally comprise suitable carrier, additives, diluting agents and/or excipients for its respective use and form, respectively, —but also agents that support the antimicrobial activity like EDTA or agents enhance the antimicrobial activity of the fusion proteins. The fusion protein may also be used with common disinfectant agents like, Alcohols, Aldehydes, Oxidizing agents, Phenolics, Quaternary ammonium compounds or UV-light. For disinfecting for example surfaces, objects and/or devices the fusion protein can be applied on said surfaces, objects and/or devices. The application may occur for instance by wetting the disinfecting composition with any means such as a cloth or rag, by spraying, pouring. The fusion proteins may be used in varying concentration depending on the respective application and the "reaction time" intended to obtain full antimicrobial activity.

In a further aspect the present invention relates to the use of the fusion protein according to the present invention as a food additive.

Further scope of applicability of the present invention will become apparent from the detailed description given hereinafter, however, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1

Cloning, Expression and Purification of Modified phiKZgp144 and ELgpgp188 Endolysin Variants phiKZgp144 as depicted in SEQ ID NO: 1 and ELgp188 as depicted in SEQ ID NO: 2 are modular endolysins originating from Pseudomonas aeruginosa phages φKZ and EL with an N-terminal peptidoglycan binding and C-terminal catalytic domain (Briers et al., 2007).

For the amplification of the open reading frame (ORF) of phiKZgp144 and ELgp188 PCR a standard 5' primer (for phiKZgp144: 5' ATGAAAGTATTACGCAAA 3' (SEQ ID NO: 83); for ELgp188 5' ATGAACTTCCGGACGAAG 3' (SEQ ID NO: 65)) and the standard 3' primers according to SEQ ID NO: 81 and 82 were applied (for phiKZgp144: TTTTCTATGTGCTGCAAC (SEQ ID NO: 81); for ELgp188: ATACGAAAT AACGTGACGA (SEQ ID NO: 82)) was used. To extend the 5' end of the open reading frame encoding phiKZgp144 or ELgp188 with a gene fragment encoding nine positively charged residues (Lys-Arg-Lys-Lys-Arg-Lys-Lys-Arg-Lys—SEQ ID NO: 11) a tail PCR with an extended 5' primer (for phiKZgp144: 5' ATGGGATCCAAACGCAAGAAACGTAAGAAA CGCAAAAAAGTATTACGCAAAG 3' (SEQ ID NO 79); for ELgp188: 5' ATGGGATCCAAACGCAAGAAACG-TAAGAAA CGCAAAAACTTCCGGACGAAG 3' (SEQ ID NO: 80)) and the standard 3' primers according to SEQ ID NO: 81 and 82 were applied. The PCR product was cloned in the pEXPSCT/TOPO® expression vector (Invitrogen, Carlsbad, Calif., USA) according to the protocol of the manufacturer. Arginine triplets were incorporated besides lysine triplets to avoid tRNA depletion and reduce the risk of frameshifts (the only two available triplets for lysine are AAA and AAG, leading to long A-stretches). Insertion of additional polycationic cassettes into the designed BamHI restriction site lengthens the tail with extra cationic residues. This insertion creates an arginine and serine triplet at each junction site (FIG. 1). Up to four polycationic peptides were fused to both phiKZgp144 and ELgp188, designated (POLY)"-gp144 or (POLY)"-gp188 (n=1, 2, 3, 4), comprising respectively 9, 19, 29 and 39 positively charged amino acid residues in the N-terminus. Accordingly, the following constructs were expressed in E. coli BL21 (DE3) pLysS cells (exponentially growing cells at 37° C., induction using 1 mM IPTG, expression for 4 h at 37° C.):

| Fusion protein | SEQ ID NO: | Number of positively charged amino acid residues |
| --- | --- | --- |
| POLY-gp144 | SEQ ID NO: 35 | 9 |
| (POLY)²-gp144 | SEQ ID NO: 36 | 19 |
| (POLY)³-gp144 | SEQ ID NO: 37 | 29 |
| (POLY)⁴-gp144 | SEQ ID NO: 38 | 39 |
| POLY-gp188 | SEQ ID NO: 39 | 9 |
| (POLY)²-gp188 | SEQ ID NO: 40 | 19 |
| (POLY)³-gp188 | SEQ ID NO: 41 | 29 |
| (POLY)⁴-gp188 | SEQ ID NO: 42 | 39 |

The modified endolysin variants POLY-gp144 (SEQ ID NO: 35), (POLY)²-gp144 (SEQ ID NO: 36), POLY-gp188 (SEQ ID NO: 39) and (POLY)²-gp188 (SEQ ID NO: 40) have been used for further investigations. Said proteins were purified by $Ni^{2+}$ affinity chromatography using the C-terminal 6×His-tag (Akta Fast Protein Liquid Chromatography using 1 ml His-trap Ni-NTA columns). The total yields per liter *E. coli* expression culture were determined by spectrophotometric measurement of the protein concentration and the total volume of the purified stock solution. The purification of gp188 derivatives was performed under more stringent conditions (65 mM imidazole) compared to gp144 derivatives (50 mM imidazole) to ensure high purity. The total yields per liter *E. coli* expression culture are shown in table 5.

TABLE 5

Yields of recombinant purification of endolysin derivatives per liter *E. coli* expression culture.

| | Endolysin | |
| --- | --- | --- |
| Fusion | phiKZgp144 | ELgp188 |
| POLY | 2 mg | 48 mg |
| (POLY)² | 0.5 mg | 0.06 mg |

Purified stock solutions were ~90% pure. Mass spectrometric analysis of purified solutions of POLY-derivatives revealed traces of the *E. coli* SOS ribosomal subunit protein L2 and 16S rRNA uridine-516 pseudo-uridylate synthase. All phiKZgp144 derivatives showed multimer formation which could be converted to monomers by addition of β-mercaptoethanol, indicating that interdisulfide bonds cause multimerization.

EXAMPLE 2

Antibacterial Activity of Modified phiKZgp144 and ELgp188 Variants

Exponential (~10⁶/ml) *P. aeruginosa* PAO1p cells (Pirnay J P et al. (2003), *J Clin Microbiol.*, 41(3):1192-1202) were 100× diluted (final density was ~10⁶/ml) and incubated at room temperature with each 10 μg undialyzed protein (unmodified endolysins phiKZgp144 (SEQ ID NO: 1) and ELpg188 (SEQ ID NO: 2) and modified endolysin variants POLY-gp144 (SEQ ID NO:35), (POLY)²-gp144 (SEQ ID NO: 36), POLY-gp188 (SEQ ID NO: 39) and (POLY)²-gp188 (SEQ ID NO: 40) at a final concentration of 100 μg/ml in buffer (20 mM $NaH_2PO_4$-NaOH pH7.4; 0.5 M NaCl; 0.5 M imidazole). After 1 hour cell suspensions were diluted in PBS buffer (10e-5, 10e-4 and 10e-3) and plated (standard LB-medium, incubated overnight at 37° C.). Additionally, a negative control containing cells in PBS buffer was plated. The residual colonies were counted after an overnight incubation. Based on the counted cell numbers the antibacterial activity as the relative inactivation (%) (=100−($N_i$/$N_0$)*100 with $N_0$=number of untreated cells and $N_i$=number of treated cells) and in logarithmic units (=$\log_{10}$ $N_0$/$N_i$) was calculated (Table 6). All samples were replicated in six fold. Averages/standard deviations are represented. Statistical analysis was performed using a student's t-test.

Unmodified endolysins phiKZgp144 and ELgp188 do not reduce cell numbers significantly compared to the negative control. This observation illustrates the efficacy of the outer membrane as a barrier for the endolysin to degrade the cell wall of the Gram-negative bacteria. In contrast as shown in Table 6 the incubation with the modified endolysins POLY-gp144, (POLY)²-gp144, POLY-gp188 and (POLY)²-gp188 causes a significant reduction (α=0.05) of the bacterial cell number (99.85±0.09% for POLY-gp144 and 98.0±0.2% for POLY-gp188). An increase of the length of the polycationic peptide further tends to strengthen the antibacterial activity, especially in case of phiKZgp144 (a reduction up to 99.98±0.02% or 3.7±0.3 log units is achieved within 1 hour for (POLY)²-gp144). Moreover, the experiments demonstrated that the modified endolysins of phiKZgp144 have a higher antibacterial activity than the modified endolysins of ELgp188.

TABLE 6

Antibacterial effect of endolysins unmodified and modified phiKZgp144 and ELgp188 variants.

| | Endolysins | | | |
| --- | --- | --- | --- | --- |
| Exponentially | phiKZgp144 | | ELgp188 | |
| growing cells | % | log | % | log |
| unmodified endolysin | 0 ± 15 | 0.00 ± 0.06 | 10 ± 13 | 0.05 ± 0.06 |
| POLY | 99.85 ± 0.09 | 2.9 ± 0.3 | 98.0 ± 0.2 | 1.7 ± 0.1 |
| (POLY)² | 99.98 ± 0.02 | 3.7 ± 0.3 | 98.9 ± 0.4 | 2.0 ± 0.2 |

Thus, the example demonstrated that the addition of a short peptide of nine cationic residues N-terminally to phiKZgp144 (SEQ ID NO: 1) is already sufficient to kill almost 99.9% of the cells within 1 hour. Poly-L-Lysine has intrinsic antibacterial activity as well, although this property is so far only ascribed to polymers of at least 20 residues (Vaara and Vaara, 1983a, 1983b). However, the concerted action of the polycationic peptide and the endolysin kills the cells.

In a further experiment the modified endolysin POLY-gp144 was dialyzed to 50 mM $KH_2PO_4$/$K_2HPO_4$ pH 7 and used instead of undialyzed protein solution as described above. Thereby, the inactivation level was additionally increased from 2.9±0.3 log units to 3.9±0.2 log units.

EXAMPLE 3

Expression of Modified phiKZgp144 and ELgp188 Variants in *Pichia pastoris* as a Host for Non-Toxic Recombinant Production The open reading frame encoding POLY-gp144 (SEQ ID NO: 35) was cloned in the pPICZαA shuttle vector (Invitrogen), which was subsequently integrated in the *P. pastoris* genome by homologous recombination (as indicated by the manufacturer; *P. pastoris* X33 cells, Invitrogen). Gene expression was induced with methanol (1%) in BMMY-medium and the supernatant was analyzed for the presence of enzymatic activity after 1, 3 and 4 days. Therefore, an amount of 30 µl supernatant of the *P. pastoris* expression culture was added to 270 µl chloroform-permeabilized *P. aeruginosa* PAO1p cells (Pirnay J P et al. (2003), *J Clin Microbiol.*, 41(3):1192-1202) after 1, 3 and 4 days (buffer condition: KH$_2$PO$_4$/K$_2$HPO$_4$ I=120 mM pH 6.2). Subsequently, the optical density was spectrophotometrically recorded (FIG. 2). A drop in optical density indicates the secretion of a muralytic enzyme by *P. pastoris*. As a negative control, *P. pastoris* X33 without expression plasmid was included. Thus, the lysis of the substrate upon addition of the supernatants sample is a measure for successful recombinant production and secretion of POLY-gp144 (SEQ ID NO: 35) by *P. pastoris*. After 1 day, a limited enzymatic activity could be detected. The maximum activity was observed after 3 days since no significant increase of activity in the supernatants was observed at the fourth day. No toxic effect on the cell density of *P. pastoris* was observed.

During expression by *P. pastoris* the α-secretion signal of the vector causes secretion of the recombinant protein to the surrounding media, which allows a simplify purification since only a limited number of other proteins is secreted. A BamHI restriction site in the 5' end of the open reading frames enables the addition of more cassettes encoding additional polycationic peptides.

EXAMPLE 4

Further Modified Endolysin phiKZgp144 Variants with Different Polycationic Peptides To test and to compare the potential of polycationic peptides variants of phiKZgp144 and other endolysin encoding genes were synthesised having different polycationic peptides at the N-terminal end of the protein. Peptide variation concerns length, composition and insertion of linker sequences. On the one hand further polycationic peptides having N-terminal multiples of the KRK motive were produced. On the other hand polycationic peptides consisting only of arginine (R) or lysine (K) were produced.

Moreover, to enhance the translation of long polycationic peptides, polycationic peptides comprising a linker sequence were produced.

The different products were cloned in the pET32b expression vector (Novagen, Darmstadt, Germany). pET32b was used to reduce potential toxicity of the polycationic peptide against the *E. coli* host. A vector-encoded fusion protein (thioredoxin) masks the polycationic peptide and can be eliminated during the purification process.

Accordingly, the following modified endolysin variants were expressed in *E. coli* BL21 (DE3) cells at 37° C. until an optical density of OD600nm=0.6 was reached. Then protein expression was induced with 1 mM IPTG (final concentration) and expression was preformed for four hours. Then *E. coli* cells were harvested by centrifugation for 20 min at 6000 g and cell disruption and protein purification was performed according the S-tag purification kit (Novagen, Darmstadt, Germany):

| Modified endolysin variant | peptide length | Sequence of the peptide |
|---|---|---|
| phiKZgp144 (SEQ ID NO: 1) | 0 | — |
| pKKZ144pET32b (SEQ ID NO: 43) | 10 | KRKKRKKRKK (SEQ ID NO: 14) |
| KRK_6_pET32b (SEQ ID NO: 44) | 6 | KRKKRK (SEQ ID NO: 10) |
| KRK_12_pET32b (SEQ ID NO: 45) | 12 | KRKKRKKRKKRK (SEQ ID NO: 15) |
| KRK_14_pET32b (SEQ ID NO: 46) | 14 | KRKKRKKRKKRKKR (SEQ ID NO: 16) |
| R9_pET32b (SEQ ID NO: 47) | 9 | RRRRRRRRR (SEQ ID NO: 12) |
| K8_pET32b (SEQ ID NO: 48) | 8 | KKKKKKKK (SEQ ID NO: 13) |
| pK2KZ144_pET32b_mod3 (SEQ ID NO: 49) | 38 | KRKKRKKRKRGSGSGKRKKRKKRKRKGSGSGKRKKRKKRK (SEQ ID NO: 28) |

All proteins were purified using the S-Tag™ rEK Purification Kit (Novagen, Darmstadt, Germany). Using the pET32b vector, the expressed proteins were not toxic to the host resulting in high yields of produced protein. Purified stock solutions showed high purity.

Exponential (~10$^6$/ml) *P. aeruginosa* PAO1p cells (Burn wound isolate, Queen Astrid Hospital, Brussels; Pirnay J P et al. (2003), *J Clin Microbiol.*, 41(3):1192-1202) were 100× diluted (final density was ~10$^6$/ml) incubated at room temperature with each 10 µg undialyzed protein as listed above at a final concentration of 100 µg/ml in buffer (20 mM NaH$_2$PO$_4$-NaOH pH7.4; 0.5 M NaCl; 0.5 M imidazole). After 1 hour cell suspensions were diluted 1:100 and plated on LB. Additionally, a negative control was plated using buffer (20 mM NaH$_2$PO$_4$-NaOH pH7.4; 0.5 M NaCl; 0.5 M imidazole). The residual colonies were counted after an overnight incubation at 37° C. Based on the counted cell numbers the antibacterial activity as the relative inactivation (%) (=100−(N$_i$/No)*100 with N$_o$=number of untreated cells and N$_i$=number of treated cells) was calculated (Table 7). All samples were replicated at least in four fold.

TABLE 7

Antibacterial effect of endolysins unmodified and modified phiKZgp144 and ELgp188

| Modified endolysin variant | Sequence of the peptide | Reduction [%] |
|---|---|---|
| phiKZgp144 (SEQ ID NO: 1) | | 0 |
| pKKZ144pET32b (SEQ ID NO: 43) | KRKKRKKRKK (SEQ ID NO: 14) | 99-99.9 |
| KRK_6_pET32b (SEQ ID NO: 44) | KRKKRK (SEQ ID NO: 10) | 99.9 |
| KRK_12_pET32B (SEQ ID NO: 45) | KRKKRKKRKKRK (SEQ ID NO: 15) | 99-99.9 |
| KRK_14_pET32b (SEQ ID NO: 46) | KRKKRKKRKKRKKR (SEQ ID NO: 16) | 99.9 |
| R9_pET32b (SEQ ID NO: 47) | RRRRRRRRR (SEQ ID NO: 12) | 99 |
| K8_pET32b (SEQ ID NO: 48) | KKKKKKKK (SEQ ID NO: 13) | 99 |
| pK2KZ144_pET32b_mod3 (SEQ ID NO: 49) | KRKKRKKRKRGSGSGKRKKRKKRKGSGSGKRKKRKKRK (SEQ ID NO: 28) | 99.9 |

Unmodified phiKZgp144 does not reduce cell numbers significantly compared to the negative control. Beyond that, modified phiKZgp144 variants wearing a polycationic peptide of N-terminal multiples of the KRK motive enhance the antimicrobial effect immensely. However, also variants having a homomer peptide of lysine or arginine show significant reduction of cells compared with unmodified phiKZgp144 as measured. Moreover, also the variant having a polycationic peptide of 38 amino acid residues and comprising a linker sequence enhance the antimicrobial effect immensely.

EXAMPLE 5

Modified Endolysin Variants of *Salmonella typhimurium* Phage PSP3

PSP3gp10 according to SEQ ID NO: 8 is a globular endolysin with 165 amino acid residues originating from *Salmonella typhimurium* phage PSP3 with a catalytic lambda-like muramidase domain. As predicted by BLASTp and Pfam analysis the PSP3gp10 endolysin comprises its catalytic domain in the range of about amino acid residue 34 to about amino acid residue 152.

Purified genomic DNA of phage PSP3 was used as a template for the amplification of the open reading frame (ORF) of PSP3gp10 in a Hot Start Taq polymerase PCR reaction (Qiagen, Germany) using the following PCR parameters:

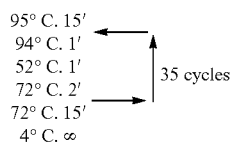

For said PCR a standard 5' primer (5' ATGGGATCCCCG-GTCATTAATACTCACCAG 3'(SEQ ID NO: 50)) and a standard 3' primer (5' TGCCATCACCCCGCCAGCCGTG 3' (SEQ ID NO: 51)) was used. To extend the 5' end of the ORF which encodes PSP3gp10 with a gene fragment encoding the polycationic 9-mer peptide Lys-Arg-Lys-Lys-Arg-Lys-Lys-Arg-Lys (SEQ ID NO: 11) a tail PCR (Hot Start Taq polymerase PCR with same parameters) with an extended 5' primer (5' ATGGGATCCAAACGCAAGAAACGTAA GAAACGCAAACCGGTCATTAATACTCACCAG 3' (SEQ ID NO: 52)) and the standard 3' primer according to SEQ ID NO: 51 was applied. Both the original unmodified PSP3gp10 PCR fragment and the PK-extended fragment were ligated in the pEXPSCT/TOPO® expression vector (Invitrogen, Carlsbad, Calif., USA) by following the TA-cloning protocol of the manufacturer.

Recombinant expression of PSP3gp10 according to SEQ ID NO: 8 and PKPSP3gp10 according to SEQ ID NO: 53 is performed in exponentially growing *E. coli* BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6xHis-tag, encoded by the pEXPSCT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.

4. Elution of bounded endolysin from the column with 10 column volumes of Elution Buffer (500 mM imidazole, 5 mM NaCl and 20 mM NaH$_2$PO$_4$-NaOH on pH 7.4) at a flow rate of 0.5 ml/min The total yields of both purified recombinant proteins per liter E. coli expression culture shown in Table 8. The values were determined by spectrophotometric measurement of the protein concentration and the total volume of the purified stock solution at a wavelength of 280 nm. Purified stock solutions consisting of PSP3gp10 and PKPSP3gp10, respectively, in Elution Buffer (20 mM NaH$_2$PO$_4$-NaOH pH7.4; 0.5 M NaCl; 500 mM imidazole) were at least 90% pure as determined visually on SDS-PAGE gels.

TABLE 8

Yields of purified recombinant PSP3gp10 endolysin and its modified variant PKPSP3gp10 per liter E. coli expression culture.

| Endolysins | Expression yield |
| --- | --- |
| PSP3gp10 (SEQ ID NO: 8) | 2.15 mg |
| PKPSP3gp10 (SEQ ID NO: 53) | 5.56 mg |

TABLE 9

List of used Gram-negative strains

| Gram-negative strain | Source | Reference |
| --- | --- | --- |
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Escherichia coli WK6 | Standard laboratory expression strain | Prof. C. Michiels |
| Salmonella typhimurium LT2 | SGSC N° 2317 | Prof. C. Michiels |

*Pirnay JP et al. (2003). Molecular epidemiology of Pseudomonas aeruginosa colonization in a burn unit: persistence of a multidrug-resistant clone and a silver sulfadiazine-resistant clone. J Clin Microbiol., 41(3): 1192-1202.

After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$\log_{10} N_0/N_i$ with $N_0$=number of untreated cells and $N_i$=number of treated cells) was calculated (Table 10).

TABLE 10

Antibacterial activity of unmodified endolysin (PSP3gp10) and its modified endolysin variant (PKPSP3gp10) with and without EDTA-Na$_2$ on different exponential growing Gram-negative species.

| | 0.5 mM EDTA | 1.315 µM PSP3gp10 | 1.315 µM PKPSP3gp10 | 1.315 µM PSP3gp10 + 0.5 mM EDTA | 1.315 µM PKPSP3gp10 + 0.5 mM EDTA |
| --- | --- | --- | --- | --- | --- |
| P. aeruginosa PAO1p | 0.146 +/− 0.002 | 0.383 +/− 0.015 | 0.344 +/− 0.163 | 3.552 +/− 0.536 | >4.146 |
| P. aeruginosa Br667 | 0.223 +/− 0.038 | 0.375 +/− 0.056 | 0.353 +/− 0.086 | 0.571 +/− 0.035 | 0.891 +/− 0.118 |
| Salmonella typhimurium | 0.104 +/− 0.049 | 0.283 +/− 0.038 | 0.327 +/− 0.057 | 0.690 +/− 0.036 | 0.850 +/− 0.032 |
| Escherichia coli WK6 | 0.393 +/− 0.035 | 0.190 +/− 0.029 | 0.205 +/− 0.088 | 0.387 +/− 0.014 | 0.584 +/− 0.024 |

To determine the anti-Gram-negative spectrum of the PKPSP3gp10 endolysin according to SEQ ID NO: 53, a combination of 1.315 µM PKPSP3gp10 endolysin and 0.5 mM EDTA was tested on the clinical P. aeruginosa strains PAO1p and Br667, Escherichia coli WK6, and Salmonella typhimurium (see Table 9). Exponential growing bacterial cells (OD$_{600nm}$ of 0.6) were 100-fold diluted to a final density of about $10^6$/ml of each strain were incubated for 30 minutes at room temperature without shaking with unmodified endolysin PSP2gp10 (SEQ ID NO: 8) and modified endolysin PKPSP3gp10 (SEQ ID NO: 53) each in combination without and with 0.5 mM EDTA. For incubation, the endolysins were used each in buffer (20 mM NaH$_2$PO$_4$-NaOH pH7.4; 0.5 M NaCl; 0.5 M imidazole) and the incubation took place at a final concentration of endolysin of 1.315 µM. As a control each strain was also incubated for 30 minutes with 0.5 mM EDTA (in same buffer as outlined above) but no endolysin.

All samples were replicated in threefold. Averages +/− standard deviations are represented. The maximal reduction observed is dependent on the detection level of 10 cells/ml and the initial cell density. For PAO1p, EDTA works synergistically with both the unmodified PSP3gp10 endolysin and its modified variant PKPSP3gp10.

EXAMPLE 6

Modified Endolysin Variants of Escherichia coli Phage P2

P2gp09 according to SEQ ID NO: 9 is a globular endolysin of 165 amino acid residues originating from Escherichia coli phage P2 with a catalytic lambda-like muramidase domain. As predicted by BLASTp and Pfam analysis the P2gp09 endolysin comprises its catalytic domain in the range of about amino acid residue 34 to about amino acid residue 152.

Purified genomic DNA of phage P2 was used as a template for the amplification of the open reading frame (ORF) of P2gp09 in standard PCR reaction with Pfu polymerase (Fermentas) using the following PCR parameters:

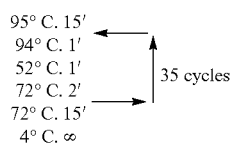

For said PCR a standard 5' primer (5' ATGGGATCCCCG-GTAATTAACACGCATC 3' (SEQ ID NO: 54)) and a standard 3' primer (5' AGCCGGTACGCCGCCAGCGGTACGC 3' (SEQ ID NO: 55)) was used. To extend the 5' end of the ORF which encodes P2gp09 with a gene fragment encoding the polycationic 9-mer peptide Lys-Arg-Lys-Lys-Arg-Lys-Lys-Arg-Lys (SEQ ID NO: 11) a tail PCR (with same parameters as standard PCR above) with an extended 5' primer (5' ATGGGATCCAAACGCAAGAAACG-TAAGAAACGC AAACCGGTAATTAACACGCATC 3' (SEQ ID NO: 56) and the standard 3' primer according to SEQ ID NO 55 was applied. Both the original unmodified P2gp09 PCR fragment and the extended fragment were ligated in the pEXPSCT/TOPO® expression vector (Invitrogen, Carlsbad, Calif., USA) by following the TA-cloning protocol of the manufacturer. Recombinant expression of P2gp09 according to SEQ ID NO: 9 and PKP2gp09 according to SEQ ID NO: 57 is performed in exponentially growing E. coli BL21 (λDE3) pLysS cells (Invitrogen) after induction with 1 mM IPTG (isopropylthiogalactoside) at 37° C. for a period of 4 hours. Both proteins were purified by Ni$^{2+}$ affinity chromatography (Akta FPLC, GE Healthcare) using the C-terminal 6xHis-tag, encoded by the pEXPSCT/TOPO® expression vector. The Ni$^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM NaH$_2$P0$_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 5 mM NaCl and 20 mM NaH$_2$P0$_4$-NaOH on pH 7.4) at a flow rate of 0.5 ml/min The total yields of both purified recombinant proteins per liter E. coli expression culture shown in Table 11. The values were determined by spectrophotometric measurement of the protein concentration and the total volume of the purified stock solution at a wavelength of 280 nm. Purified stock solutions consisting of P2gp09 and PKP2gp09, respectively, in Elution Buffer (20 mM NaH$_2$P0$_4$-NaOH pH7.4; 0.5 M NaCl; 500 mM imidazole) were at least 95% pure as determined visually on SDS-PAGE gels.

TABLE 11

Yields of purified recombinant P2gp09 endolysin and its PK-modified derivative PKP2gp09 per liter E. coli expression culture.

| Endolysins | Expression yield |
| --- | --- |
| P2gp09 (SEQ ID NO: 9) | 5.52 mg |
| PKP2gp09 (SEQ ID NO: 57) | 3.40 mg |

To determine the anti-Gram-negative spectrum of the PK2gp09 endolysin according to SEQ ID NO: 57, a combination of 1.315 µM PK2gp09 endolysin and 0.5 mM EDTA was tested on the clinical P. aeruginosa strains PAO1p and Br667, Burkholderia pseudomallei, Pseudomonas putida G1 and on Escherichia coli WK6 (see Table 13). Exponential growing bacterial cells (OD$_{600nm}$ of 0.6) were 100-fold diluted to a final density of about 10$^6$/ml of each strain was incubated for 30 minutes at room temperature without shaking with unmodified endolysin P2gp09 (SEQ ID NO: 9) and modified endolysin PKP2gp09 (SEQ ID NO: 57) each in combination without and with 0.5 mM EDTA. For incubation, the endolysins were used each in buffer (20 mM NaH$_2$P0$_4$-NaOH pH7.4; 0.5 M NaCl; 0.5 M imidazole) and the incubation took place at a final concentration of endolysin of 1.315 µM. As a control each strain was also incubated for 30 minutes with 0.5 mM EDTA (in same buffer as outlined above) but no endolysin. After incubation cell suspensions were diluted three times (respectively 10$^5$-10$^4$-10$^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=log$_{10}$ N$_0$/N$_i$ with N$_0$=number of untreated cells and N$_i$=number of treated cells, both counted after incubation) was calculated (Table 12).

TABLE 12

Antibacterial activity of unmodified endolysin (P2gp09) and its modified endolysin variant (P2gp09) with and without EDTA-Na$_2$ on different exponential growing Gram-negative species.

| | 0.5 mM EDTA | 1.315 µM P2gp09 | 1.315 µM PKP2gp09 | Δ | 1.315 µM P2gp09 + 0.5 mM EDTA | 1.315 µM PKP2gp09 + 0.5 mM EDTA | Δ |
| --- | --- | --- | --- | --- | --- | --- | --- |
| P. aeruginosa PAO1p | 0.330 +/− 0.146 | 0.374 +/− 0.084 | 0.326 +/− 0.069 | −0.038 | 2.840 +/− 0.079 | 3.172 +/− 0.056 | 0.332 |
| P. aeruginosa Br667 | 0.003 +/− 0.051 | 0.246 +/− 0.042 | 0.300 +/− 0.062 | 0.054 | 0.582 +/− 0.074 | 0.952 +/− 0.213 | 0.370 |
| P. putida G1 | 0.072 +/− 0.084 | 0.419 +/− 0.024 | 1.014 +/− 0.139 | 0.595 | 3.919 +/− 0.118 | >4.386 | >0.467 |
| Burkholderia pseudomallei | 0.206 +/− 0.151 | 0.769 +/− 0.110 | 1.163 +/− 0.073 | 0.394 | 3.890 +/− 0.056 | 4.255 +/− 0.001 | 0.365 |
| Escherichia coli WK6 | 0.153 +/− 0.046 | 0.751 +/− 0.053 | 1.104 +/− 0.039 | 0.353 | 0.784 +/− 0.071 | 1.545 +/− 0.102 | 0.749 |

All samples were replicated in threefold. Averages +/− standard deviations are represented. The maximal reduction observed is dependent on the detection level of 10 cells/ml and the initial cell density.

TABLE 13

List of used Gram-negative strains

| Gram-negative strain | Source | Reference |
|---|---|---|
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Burkholderia pseudomallei | Clinical isolate, UZ Gasthuisberg, Leuven | Prof J. Verhaegen |
| Escherichia coli WK6 | Standard laboratory expression strain | Prof C. Michiels |
| Pseudomonas putida G1 | Soil isolate, Moskow | Prof V. Krylov |

*Pirnay JP et al., (2003). Molecular epidemiology of *Pseudomonas aeruginosa* colonization in a burn unit: persistence of a multidrug-resistant clone and a silver sulfadiazine-resistant clone. *J Clin Microbiol.*, 41(3): 1192-1202.

EXAMPLE 7

Modified Endolysin Variants of *Pseudomonas putida* Phage OBP

OBPgpLYS according to SEQ ID NO: 7 is a modular endolysin of 328 amino acid residues originating from *Pseudomonas putida* phage OBP with a putative N-terminal peptidoglycan binding domains and a C-terminal catalytic chitinase domain. As predicted by BLASTp and Pfam analysis the OBPgpLYS endolysin comprises its catalytic domain in the range of about amino acid residue 126 to about amino acid residue 292 and the N-terminal peptidoglycan binding domain in the range of about amino acid residues 7 to 96.

Purified genomic DNA of phage OBP was used as a template for the amplification of the open reading frame (ORF) of OBPgpLYS in standard PCR reaction with Pfu polymerase (Fermentas, Ontario, Canada) using the following PCR parameters:

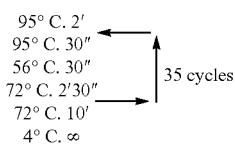

Therefore a standard 5' primer (5' ATGAAAAATAGC-GAGAAGAAT 3' (SEQ ID NO: 58)) and a standard 3' primer (5' AACTATTCCGAGTGCTTTCTTTGT 3' (SEQ ID NO: 59)) was used. To extend the 5' end of the ORF which encodes OBPgpLYS with a gene fragment encoding the polycationic 9-mer peptide Lys-Arg-Lys-Lys-Arg-Lys-Lys-Arg-Lys- (SEQ ID NO: 11) a tail PCR (with same parameters as standard PCR above) with an extended 5' primer (5' ATGGGATCCAAACGCAAGAAACG-TAAGAAACGCAAAAAAAATAGCGAG AAGAAT 3' (SEQ ID NO: 60)) and the standard 3' primer according to SEQ ID NO 59 was applied. Both the original unmodified OBPgpLYS PCR fragment and the extended fragment were ligated in the pEXPSCT/TOPO® expression vector (Invitrogen, Carlsbad, Calif., USA) by following the TA-cloning protocol of the manufacturer.

Recombinant expression of OBPgpLYS according to SEQ ID NO: 7 and PKOBPgpLYS according to SEQ ID NO: 61 is performed in exponentially growing *E. coli* BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6×His-tag, encoded by the pEXPSCT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 5 mM NaCl and 20 mM $NaH_2PO_4$-NaOH on pH 7.4) at a flow rate of 0.5 ml/min The total yields of both purified recombinant proteins per liter *E. coli* expression culture shown in Table 14. The values were determined by spectrophotometric measurement of the protein concentration and the total volume of the purified stock solution at a wavelength of 280 nm. Purified stock solutions consisting of OBPgpLYS and PKOBPgpLYS, respectively, in Elution Buffer (20 mM $NaH_2PO_4$-NaOH pH7.4; 0.5 M NaCl; 500 mM imidazole) were at least 90% pure as determined visually on SDS-PAGE gels.

TABLE 14

Yields of purified recombinant OBPgpLYS endolysin and its PK-modified derivative PKOBPgpLYS per liter *E. coli* expression culture.

| Endolysins | Expression yield |
|---|---|
| OBPgpLYS (SEQ ID NO: 7) | 3.3 mg |
| PKOBPgpLYS (SEQ ID NO: 61) | 4.7 mg |

To determine the anti-Gram-negative spectrum of the PKOBPgpLYS endolysin according to SEQ ID NO: 61, a combination of 1.313 μM PK OBPgpLYS endolysin and 0.5 mM EDTA was tested on the clinical multiresistant *P. aeruginosa* strain Br667, *Pseudomonas putida* G1 (host of phage OBP) and a range of other Gram-negative pathogens (*Escherichia coli* WK6, *Salmonella typhimurium* LT2 and *Burkholderia pseudomallei*) (see Table 16). Exponential growing bacterial cells ($OD_{600nm}$ of 0.6) were 100-fold diluted to a final density of about $10^6$/ml of each strain was incubated for 30 minutes at room temperature without shaking with unmodified endolysin OBPgpLYS (SEQ ID NO: 7) and modified endolysin PKOBPgpLYS (SEQ ID NO: 61) each in combination without and with 0.5 mM EDTA. For incubation, the endolysins were used each in buffer (20 mM $NaH_2PO_4$-NaOH pH7.4; 0.5 M NaCl; 0.5 M imidazole) and the incubation took place at a final concentration of endolysin of 1.313 μM. As a control each strain was also incubated for 30 minutes with 0.5 mM EDTA (in same buffer as outlined above) but no endolysin. After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$\log_{10}$ $N_0/N_i$ with $N_0$=number of untreated cells and $N_i$=number of treated cells, both counted after incubation) was calculated (Table 15). All samples were replicated in threefold. Averages +/− standard deviations are represented. The maximal reduction observed is dependent on the detection level of 10 cells/ml and the initial cell density.

TABLE 15

Antibacterial activity of unmodified endolysin (OBPgpLYS) and its modified endolysin variant (PKOBPgpLYS) with and without EDTA-Na$_2$ on different exponential growing Gram-negative species.

|  | 0.5 mM EDTA | 1.313 µM OBPgpLYS | 1.313 µM PKOBPgpLYS | 1.313 µM OBPgpLYS + 0.5 mM EDTA | 1.313 µM PKOBPgpLYS + 0.5 mM EDTA |
|---|---|---|---|---|---|
| *P. aeruginosa* PAO1p | 0.130 +/− 0.023 | 2.531 +/− 0.173 | 3.079 +/− 0.015 | 4.357 +/− 1.857 | >5.687 |
| *P. aeruginosa* Br667 | 0.031 +/− 0.023 | 1.082 +/− 0.083 | 1.163 +/− 0.063 | 3.144 +/− 0.223 | 5.272 +/− 0.573 |
| *P. putida* G1 | 0.412 +/− 0.055 | 0.141 +/− 0.027 | 0.904 +/− 0.079 | 4.891 +/− 0.000 | >4.891 |
| *Burkholderia pseudomallei* | 0.220 +/− 0.081 | 0.997 +/− 0.131 | 1.806 +/− 0.287 | 4.08 +/− 0.301 | >4.861 |
| *Escherichia coli* WK6 | 0.592 +/− 0.113 | 0.681 +/− 0.032 | 1.434 +/− 0.018 | 1.179 +/− 0.200 | 1.695 +/− 0.147 |
| *Salmonella typhimurium* | 0.054 +/− 0.048 | 0.076 +/− 0.011 | 0.127 +/− 0.013 | 0.774 +/− 0.052 | 0.908 +/− 0.037 |

TABLE 16

List of used Gram-negative strains

| Gram-negative strain | Source | Reference |
|---|---|---|
| *Pseudomonas aeruginosa* PAO1p | Burn wound isolate, Queen Astrid Hospital, Brussels | Pirnay et al., 2003* |
| *Pseudomonas aeruginosa* Br667 | Burn wound isolate, Queen Astrid Hospital, Brussels | Pirnay et al., 2003* |
| *Pseudomonas putida* G1 | Soil isolate, Moskow | Prof V. Krylov |
| *Burkholderia pseudomallei* | Clinical isolate, UZ Gasthuisberg, Leuven | Prof J. Verhaegen |
| *Escherichia coli* WK6 | Standard laboratory expression strain | Stratagene |
| *Salmonella typhimurium* LT2 | SGSC N° 2317 | Prof C. Michiels |

*Pirnay JP, De Vos D, Cochez C, Bilocq F, Pirson J, Struelens M, Duinslaeger L, Cornelis P, Zizi M, Vanderkelen A. (2003). Molecular epidemiology of *Pseudomonas aeruginosa* colonization in a burn unit: persistence of a multidrug-resistant clone and a silver sulfadiazine-resistant clone. *J Clin Microbiol.*, 41(3): 1192-1202.

While the global efficacy of the OBPgpLYS treatment is species dependent, the results in table 16 show an added effect of the PKOBPgpLYS compared to unmodified OBPgpLYS for all bacterial species tested, both in the absence as the presence of 0.5 mM EDTA. For *Pseudomonas* and *Burkholderia* species, a clear synergistic effect with EDTA is observed for the PKOBPgpLYS activity.

EXAMPLE 8

Effect of Different EDTA Concentration on the Antibacterial Activity of OBPgpLYS and PKOBPgpLYS To determine the influence of EDTA on the antibacterial activity of unmodified and modified endolysins the antibacterial activity of the unmodified OBPgpLYS endolysin (SEQ ID NO: 7) and the PKOBPgpLYS endolysin (SEQ ID NO: 61) was tested on *Pseudomonas aeruginosa* PAO1p cells (Pirnay J P et al. J Clin Microbiol., 41(3):1192-1202 (2003)) using different concentrations of EDTA and endolysins. Exponential growing bacterial cells ($OD_{600nm}$ of 0.6) were 100-fold diluted to a final density of about $10^6$/ml and incubated for 30 minutes at room temperature without shaking with unmodified endolysin OBPgpLYS (SEQ ID NO: 7) and modified endolysin PKOBPgpLYS (SEQ ID NO: 61). For incubation, the endolysins were used each in buffer (20 mM $NaH_2PO_4$-NaOH pH7.4; 0.5 M NaCl; 0.5 M imidazole) at final concentrations of endolysin of 0.013 µM, 0.131 µM and 1.315 µM. Thereby, the following different EDTA concentrations were used: 0 mM, 0.05 mM, 0.5 mM and 10 mM. As a control one sample was also incubated for 30 minutes with no endolysin, instead of there was buffer (20 mM $NaH_2PO_4$-NaOH pH7.4; 0.5 M NaCl; 0.5 M imidazole) added. After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$\log_{10} N_0/N_i$ with $N_0$=number of untreated cells and $N_i$=number of treated cells, both counted after incubation) was calculated (Table 17). All samples were replicated in threefold. Averages +/− standard deviations are represented. The maximal reduction observed (5.69 log units) is dependent on the detection level of 10 cells/ml and the initial cell density. "Δ" gives the difference of activity between the respective OBPgpLYS and PKOBPgpLYS samples.

TABLE 17

Antibacterial activity of unmodified endolysin (OBPgpLYS) and its modified endolysm variant (PKOBPgpLYS) in combination with different EDTA concentrations on exponential growing Pseudomonas aeruginosa PAO1p cells

| | Concentration of EDTA-Na$_2$ (in mM) | | | |
|---|---|---|---|---|
| | 0 | 0.05 | 0.5 | 10 |
| No endolysin | / | 0.028 +/− 0.008 | 0.130 +/− 0.023 | 1.827 +/− 0.052 |
| 0.013 µM OBPgpLYS | 0.956 +/− 0.110 | / | 4.626 +/− 0.287 | / |
| 0.013 µM PKOBPgpLYS | 0.992 +/− 0.181 | / | 5.204 +/− 0.000 | / |
| Δ | 0.036 | | 0.578 | |
| 0.131 µM OBPgpLYS | 2.158 +/− 0.027 | / | 4.599 +/− 0.275 | / |
| 0.131 µM PKOBPgpLYS | 2.529 +/− 0.184 | / | 5.671 +/− 0.000 | / |
| Δ | 0.371 | | 1.072 | |
| 1.315 µM OBPgpLYS | 2.531 +/− 0.173 | 2.762 +/− 0.091 | 4.357 +/− 1.857 | 4.888 +/− 0.275 |
| 1.315 µM PKOBPgpLYS | 3.079 +/− 0.015 | 4.145 +/− 0.015 | >5.687 | >5.687 |
| Δ | 0.548 | 1.383 | >1.330 | >0.799 |

As shown in Table 17 unmodified endolysin OBPgpLYS reduces cell numbers significantly with more than 2.5 log units for 1.315 µM and with +/−1 log unit for 0.013 µM, compared to the negative control. Modified endolysin PKOBPgpLYS results in an added 0.5 log units reduction for exponentially growing PAO1p cells. The observed antibacterial effect can be increased to more as 5.69 log units reduction (beneath the detection level) by combining PKOBPgpLYS with the outer membrane permeabilizer EDTA-Na$_2$ at a concentration of 0.5 and 10 mM EDTA. The difference in activity between the unmodified OBPgpLYS and the PK-modified OBPgpLYS increases by raising the amount of added endolysin (from 0.013-1.315 µM endolysin).

EXAMPLE 9

Antibacterial Activity of Modified phiKZgp144 Variants on Different Gram-Negative Bacteria To test and to compare the potential of polycationic peptides variants of phiKZgp144 and other endolysins, encoding genes were synthesised having polycationic peptides at the N-terminal end of the protein.

The different products were cloned in the pET32b expression vector (Novagen, Darmstadt, Germany). pET32b was used to reduce potential toxicity of the polycationic peptide against the E. coli host. A vector-encoded fusion protein (thioredoxin) masks the polycationic peptide and can be eliminated during the purification process.

The genes encoding smi01 (YP_001712536) and KRK9_smi01 (SEQ ID NO: 75) were fully synthesised (Entelechon, Regensburg, Germany) and cloned into pET32b.

Accordingly, the following modified endolysin variants were expressed in E. coli BL21 (DE3) cells at 37° C. until an optical density of OD600nm=0.6 was reached: smi01 (YP_001712536), KRK9_smi01 (SEQ ID NO: 75), phiKZgp144 (SEQ ID NO: 1), pKKZ144pET32b (SEQ ID NO: 43) and POLYKZ144 (SEQ ID NO: 35). Protein expression was induced with 1 mM IPTG (final concentration) and expression was preformed for four hours. Then E. coli cells were harvested by centrifugation for 20 min at 6000 g and cell disruption and protein purification was performed using the S-Tag™ rEK Purification Kit (Novagen, Darmstadt, Germany). Using the pET32b vector, the expressed proteins were not toxic to the host resulting in high yields of produced protein. Purified stock solutions showed high purity.

For testing and as reference for comparison phiKZgp144 and POLYgp144 were synthesized and purified as described in EXAMPLE 1.

Exponential (~10$^6$/ml) growing cells of P. aeruginosa PAO1p (Burn wound isolate, Queen Astrid Hospital, Brussels; Pirnay J P et al. (2003), J Clin Microbiol., 41(3):1192-1202), Acinetobacter baumannii (DSMZ 30007) or Burkholderia solanaceum (Isolate provided by Prof. C. Michiels) were 100× diluted (final density was ~10$^6$/ml) incubated at room temperature with each 10 µg undialyzed protein as listed above at a final concentration of 100 µg/ml in buffer (20 mM NaH$_2$PO$_4$-NaOH pH7.4; 0.5 M NaCl; 0.5 M imidazole). After 1 hour cell suspensions were diluted 1:100 and plated on LB. Additionally, a negative control was plated using buffer (20 mM NaH$_2$PO$_4$-NaOH pH7.4; 0.5 M NaCl; 0.5 M imidazole). The residual colonies were counted after an overnight incubation at 37° C. Based on the counted cell numbers the antibacterial activity as the relative inactivation (%) (=100−(N$_i$/No)*100 with N$_0$=number of untreated cells and N$_i$=number of treated cells) was calculated (Table 18). All samples were replicated at least in four fold.

TABLE 18

Antibacterial effect of different modified endolysin variants (NCBI numbers in brackets) on different bacterial species

| Protein | Bacterial species | Reduction [%] |
|---|---|---|
| smi01 (YP_001712536) | Acinetobacter baumannii DSMZ 30007 | 0 |
| KRK9_smi01 | Acinetobacter baumannii DSMZ 30007 | 50 |
| phiKZgp144 | Pseudomonas aeruginosa | 0 |
| pKKZ144pET32b | Pseudomonas aeruginosa | 99-99.9 |
| phiKZgp144 | Acinetobacter baumannii DSMZ 30007 | 0 |
| pKKZ144pET32b | Acinetobacter baumannii DSMZ 30007 | 99.9 |
| phiKZgp144 | Burkholderia solanacearum | 0 |
| POLYKZ144 | Burkholderia solanacearum | 99-99.9 |

Unmodified endolysins phiKZgp144 and smi01 (YP_001712536) do not reduce cell numbers significantly compared to the negative control. This observation again illustrates the efficacy of the outer membrane as a barrier for the endolysin to degrade the cell wall of the Gram-negative bacteria. In contrast as shown in Table 18 the incubation with the modified endolysins KRK9_smi01, pKKZ144pET32b and POLY-gp144 causes a significant reduction of the bacterial cell number on Acinetobacter baumannii (50% for KRK_smi01; 99.9% for pKKZ144pET32b), *Pseudomonas aeruginosa* (90-99.9% for pKKZ144pET32b) and *Burkholderia solanaceum* (90-99.9% for POLYKZ144).

These experiments demonstrate the applicability of the cationic/polycationic fusion approach for other endolysins. Moreover, the experiments demonstrated that the modified endolysins are active on a variety of bacteria.

EXAMPLE 10

Reduction of *Pseudomonas aeruginosa* Biofilm

In the present experiment the antimicrobial activity of the modified endolysin variants SMAP29-KZ144 and PK-OBP, of the endolysins OBP and KZ144 and of the peptide PK was tested against the biofilm of the *Pseudomonas aeruginosa* strains 2572 and 2573.

Biofilm reduction was quantified using crystal violet assay (Peeters et al., J Microbiol Methods 72: 157-165 (2008)).

Biofilm Formation:

Overnight liquid cultures of a mucoid strain of, *Pseudomonas aeruginosa* 2572 (patient isolate), *Pseudomonas aeruginosa* 2573 and a non-mucoid *E. coli* BL21(DE3) were diluted to OD600=0.1. A polystyrene 96-well plate was inoculated with 100 µl culture/well. After 4 h incubation at 37° C. supernatant was discarded and adherent bacteria were washed using 100 µl physiological saline (PS). Inoculated wells were filled with 100 µl liquid LB media and incubated for an additional 24 h period. After discarding the supernatant the developed biofilm was washed again with 100 µl PS.

Biofilm Treatment:

Biofilm was treated using 50 µg/well PKKZ144 or 20 u/well alginate lyase or 50 µg/well SMAP29-KZ144 and KZ144 or 25 µg/well PK-OBP and OBP or 1.25 µg PK-Peptide (all in buffer with 500 mM NaCl) diluted one part to one part 2×LB (without NaCl) media and incubated for 12 h. Untreated series were done as negative controls (one part protein buffer to one part 2×LB without NaCl). After discarding the supernatant the developed biofilm was washed again with 100 µl PS.

Biofilm Quantification:

The washed biofilm was fixed with 300 µl methanol (99%; 15 min) and air-dried. Staining was done using 100 µl 0.3% crystal violet. After 20 min wells were rinsed with tap water and 300 µl 33% acetic acid was used dissolving the bound crystal violet out of extracellular matrix of the biofilm. After 20 min 1:10 dilution was made and absorption (590 nm) was measured.

Statistical analysis showed a massive reduction of detected biofilm using PKKZ144 compared to alginate lyase-treated or untreated inoculates. Using PKKZ144 it was possible to reduce the biofilm to the level of a non-mucoid *E. coli* lab strain.

Also the modified endolysin variants SMAP29-KZ144 and PK-OBP showed massive reduction of the *Pseudomonas aeruginosa* biofilm compared to the endolysins OBP and KZ144. Contrarily, the PK-peptide seems to enhance the formation of the *Pseudomonas aeruginosa* biofilm.

EXAMPLE 11

Reduction of *Acinetobacter baumannii* Biofilm

In the present experiment the antimicrobial activity of the modified endolysin variant PK-OBP, of the endolysin OBP and of the peptide PK was tested against the biofilm of the *Acinetobacter* baumannii strain DSMZ30007.

Biofilm reduction was quantified using crystal violet assay (Peeters et al., J Microbiol Methods 72: 157-165 (2008)).

The biofilm formation, treatment and quantification were perfomed as described in Example 10.

The modified endolysin variant PK-OBP showed massive reduction of the *Acinetobacter baumannii* biofilm compared to the endolysin OBP. Contrarily, the PK-peptide seems to enhance the formation of the *Acinetobacter baumannii* biofilm.

EXAMPLE 12

Reduction of *Staphylococcus aureus* Biofilm

In the present experiment the antimicrobial activity of the fusion proteins Ply2638-PK and PK-Lysostaphin, of the enzymes Lysostaphin and Ply2638 and of the peptide PK was tested against the biofilm of the *Staphylococcus aureus* strain KS13.

Biofilm reduction was quantified using crystal violet assay (Peeters et al., J Microbiol Methods 72: 157-165 (2008)).

The biofilm formation, treatment and quantification were perfomed as described in Example 10. Except that for the biofilm treatment, 25 µg/well Ply2638A-PK and Ply2638A or 18 µg/well PK-Lysostaphin and Lysostaphin or 1.25 µg PK-Peptide was used The fusion proteins PK-Lysostaphin and PK-Ply2638 showed massive reduction of the *Staphylococcus aureus* biofilm compared to the enzymes Lysostaphin and Ply2638. Contrarily, the PK-peptide seems to enhance the formation of the *Staphylococcus aureus* biofilm.

EXAMPLE 13

Reduction of *Listeria monocytogenes* Biofilm

In the present experiment the antimicrobial activity of the modified endolysin variant Pentapeptide-Ply511 was tested against the biofilm of the *Listeria monocytogenes* strain ScottA.

Biofilm reduction was quantified using crystal violet assay (Peeters et al., J Microbiol Methods 72: 157-165 (2008)).

The biofilm formation, treatment and quantification were perfomed as described in Example 10. Except that for the biofilm treatment, 25 µg/well Pentapeptide-Ply511 was used.

The modified endolysin variant PK-Ply511 showed massive reduction of the *Listeria monocytogenes* biofilm.

The invention claimed is:

1. A method of eliminating or reducing an existing bacterial biofilm comprising:
   (a) providing a fusion protein comprising a phiKZgp 144 endolysin according to SEQ ID NO: 1, to which a peptide comprising the amino acid sequence of SEQ ID NO:94 is fused; and
   (b) contacting a material, liquid, surface or biological material containing the bacterial biofilm with said fusion protein to effect membrane or LPS disruption in said bacterial biofilm, thereby eliminating or reducing the bacterial biofilm.

2. The method according to claim 1, wherein said peptide is fused to the N- and/or the C-terminus of the endolysin.

3. A method of eliminating or reducing an existing bacterial biofilm comprising:
   (a) providing a fusion protein comprising the amino acid sequence of SEQ ID NO: 139; and
   (b) contacting a material, liquid, surface or biological material containing the bacterial biofilm with said fusion protein to effect membrane or LPS disruption in said bacterial biofilm, thereby eliminating or reducing the bacterial biofilm.

4. The method according to claim 1, wherein the material contacted with the fusion protein is a stone, rocks, soil, sediments, food, feed or cosmetics.

5. The method according to claim 1, wherein the liquid contacted with the fusion protein is water.

6. The method according to claim 5, wherein water is drinking water, ground water or waste water, hot spring, sea, lake, river, any kind of aqueous system, cleaning and storage solutions of contact lenses, dentures, implants, prothesis or braces.

7. The method according to claim 1, wherein the liquid contacted with the fusion protein is any substance derived or obtained from a living organism.

8. The method according to claim 1, wherein the liquid contacted with the fusion protein is surface of medical devices, of industrial or potable water system piping and of natural aquatic systems.

9. The method according to claim 1, wherein in combination or in addition to the fusion protein antibiotics can be added.

10. The method according to claim 3, wherein said peptide is fused to the N- and/or the C-terminus of the endolysin.

11. The method according to claim 3, wherein the material contacted with the fusion protein is a stone, rocks, soil, sediments, food, feed or cosmetics.

12. The method according to claim 3, wherein the liquid contacted with the fusion protein is water.

13. The method according to claim 12, wherein water is drinking water, ground water or waste water, hot spring, sea, lake, river, any kind of aqueous system, cleaning and storage solutions of contact lenses, dentures, implants, prothesis or braces.

14. The method according to claim 3, wherein the liquid contacted with the fusion protein is any substance derived or obtained from a living organism.

15. The method according to claim 3, wherein the liquid contacted with the fusion protein is surface of medical devices, of industrial or potable water system piping and of natural aquatic systems.

16. The method according to claim 3, wherein in combination or in addition to the fusion protein antibiotics can be added.

* * * * *

UNITED STATES PATENT AND TRADEMARK OFFICE
CERTIFICATE OF CORRECTION

PATENT NO.        : 9,534,223 B2
APPLICATION NO.   : 13/643900
DATED             : January 3, 2017
INVENTOR(S)       : Stefan Miller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this
Twenty-fifth Day of September, 2018

Andrei Iancu
*Director of the United States Patent and Trademark Office*